United States Patent
Kaneko et al.

(10) Patent No.: US 12,252,474 B2
(45) Date of Patent: Mar. 18, 2025

(54) ULTRAVIOLET ABSORBER HAVING EXCELLENT HEAT RESISTANCE AND LONG-WAVELENGTH ABSORPTION

(71) Applicant: MIYOSHI OIL & FAT CO., LTD., Tokyo (JP)

(72) Inventors: Nobuhiro Kaneko, Tokyo (JP); Daisuke Nakamura, Tokyo (JP); Kotaro Kaneko, Tokyo (JP); Koji Kawai, Tokyo (JP)

(73) Assignee: MIYOSHI OIL & FAT CO., LTD., Tokyo (JP)

( * ) Notice: Subject to any disclaimer, the term of this patent is extended or adjusted under 35 U.S.C. 154(b) by 0 days.

(21) Appl. No.: 17/439,716

(22) PCT Filed: Apr. 27, 2020

(86) PCT No.: PCT/JP2020/017965
§ 371 (c)(1),
(2) Date: Sep. 15, 2021

(87) PCT Pub. No.: WO2020/218619
PCT Pub. Date: Oct. 29, 2020

(65) Prior Publication Data
US 2022/0162174 A1 May 26, 2022

(30) Foreign Application Priority Data

Apr. 26, 2019 (JP) .................................. 2019-086472

(51) Int. Cl.
| | | |
|---|---|---|
| C07D 249/20 | (2006.01) | |
| C07D 403/04 | (2006.01) | |
| C07D 417/04 | (2006.01) | |
| C08K 5/00 | (2006.01) | |
| C08K 5/3475 | (2006.01) | |

(52) U.S. Cl.
CPC ......... *C07D 249/20* (2013.01); *C07D 403/04* (2013.01); *C07D 417/04* (2013.01); *C08K 5/005* (2013.01); *C08K 5/3475* (2013.01)

(58) Field of Classification Search
CPC ............................. C07D 249/20; C08K 5/3475
See application file for complete search history.

(56) References Cited

U.S. PATENT DOCUMENTS

| | | | | |
|---|---|---|---|---|
| 4,929,250 | A * | 5/1990 | Hung | D06P 1/6426 351/159.63 |
| 5,700,394 | A | 12/1997 | Isharani et al. | |
| 2001/0007886 | A1* | 7/2001 | Ravichandran | C07D 249/20 524/91 |
| 2001/0025198 | A1 | 9/2001 | Faubl | |
| 2002/0061381 | A1 | 5/2002 | Saito | |
| 2003/0098440 | A1 | 5/2003 | Musa et al. | |
| 2004/0192927 | A1* | 9/2004 | Pastor | C07D 403/04 548/257 |
| 2010/0163813 | A1 | 7/2010 | Fritzsche et al. | |
| 2015/0321453 | A1 | 11/2015 | Lellig et al. | |
| 2018/0134872 | A1 | 5/2018 | Shishino et al. | |
| 2019/0315722 | A1 | 10/2019 | Kawai et al. | |
| 2022/0363650 | A1* | 11/2022 | Kawaguchi | C07D 249/20 |

FOREIGN PATENT DOCUMENTS

| | | |
|---|---|---|
| CN | 102356076 A | 2/2012 |
| CN | 107089973 A | 8/2017 |
| CN | 108947920 A | 12/2018 |
| EP | 0292618 A1 | 11/1988 |

(Continued)

OTHER PUBLICATIONS

Machine translation of JP 2002040232 (2002, 15 pages).*

(Continued)

*Primary Examiner* — Brieann R Johnston
(74) *Attorney, Agent, or Firm* — Fox Rothschild LLP

(57) ABSTRACT

Provided is an ultraviolet absorber with a high molar extinction coefficient that is particularly superior in heat resistance, odor suppression at the time of thermal decomposition and long-wavelength absorption, as compared to a conventional ultraviolet absorber. The ultraviolet absorber is an ultraviolet absorber comprising a 2-phenylbenzotriazole derivative having a bonding group represented by the following formula (I) or (II):

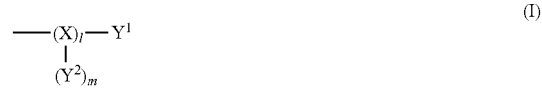

(I)

wherein X represents a nitrogen atom, an oxygen atom or a residue obtained by eliminating a hydrogen atom from an amide group; l represents an integer of 0 or 1; $Y^1$ represents a substituted or unsubstituted aromatic hydrocarbon group; m is 1 when X is a nitrogen atom or a residue obtained by eliminating a hydrogen atom from an amide group, or 0 when X is an oxygen atom; $Y^2$ represents a hydrogen atom, a substituted or unsubstituted aliphatic hydrocarbon group, or a substituted or unsubstituted aromatic hydrocarbon group,

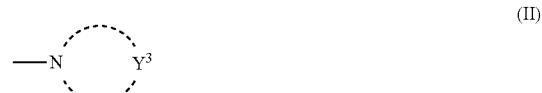
(II)

wherein $Y^3$ forms a substituted or unsubstituted hetero ring together with a nitrogen atom N.

9 Claims, 1 Drawing Sheet

(56) References Cited

FOREIGN PATENT DOCUMENTS

| JP | 49061068 A | * | 6/1974 | |
|---|---|---|---|---|
| JP | S61176640 A | | 8/1986 | |
| JP | H03-241069 A | | 10/1991 | |
| JP | 2000119260 A | | 4/2000 | |
| JP | 2002040232 A | * | 2/2002 | |
| JP | 2002-169020 A | | 6/2002 | |
| JP | 2008242179 A | | 10/2008 | |
| JP | 2016169181 A | | 9/2016 | |
| JP | 2019-56048 A | | 4/2019 | |
| WO | 02/12252 A1 | | 2/2002 | |
| WO | WO-2019069549 A1 | * | 4/2019 | ........... C07D 249/20 |

OTHER PUBLICATIONS

Abstract of JP 49061068 (1974, 2 pages).*
Machine translation of WO 2019069549 (2019, 21 pages).*
International Search Report mailed on Jul. 28, 2020 in PCT/JP2020/017965.
Bojinov et al.: "Synthesis and absorption properties of new yellow-green emitting benzo[de]isoquinoline-1,3-diones containing hindered amine and 2-hydroxyphenylbenzotriazole fragments", Dyes and Pigments, Elsevier Applied Science Publishers Barking, GB, vol. 74, No. 3, Mar. 7, 2007 (Mar. 7, 2007), pp. 551-560, XP005912529, ISSN: 0143-7208, DOI: 10.1016/J.DYEPIG.2006.03.016.
Bojinov Vladimir: "Synergistic efficiency of combined HALS-UV absorber polymerizable stabilizers", Journal of Applied Polymer Science, vol. 102, No. 3, Nov. 5, 2006 (Nov. 5, 2006), pp. 2408-2415, XP093003323, US ISSN: 0021-8995, DOI: 10.1002/app.24511.
Bojinov V B et al: "Synthesis of novel bifunctional polymer stabilizers—A combination of HALS and UV absorber", May 15, 2006 (May 15, 2006), Journal of Photochemistry, Elsevier, Amsterdam, NL, pp. 205-212, XP028008499, ISSN: 1010-6030 [retrieved on May 15, 2006].
Bojinov V B et al: "Novel functionalized 2-(2-hydroxyphenyl)-benzotriazole - benzo[de]isoquinoline-1,3-dione fluorescent UV absorbers", Journal of Photochemistry, Elsevier, Amsterdam, NL, vol. 172, No. 3, Jun. 5, 2005 (Jun. 5, 2005), pp. 308-315, XP027788653, ISSN: 1010-6030 [retrieved on Jun. 5, 2005].
Bojinov V et al: "Novel adducts of a 2-(2-hydroxyphenyl)-benzotriazole and a blue emitting benzo deisoquinoline-1,3-dione for "one-step" fluorescent brightening and stabilization of polymers", Polymer Degradation and Stability, Barking, GB, vol. 88, No. 3, Jun. 1, 2005 (Jun. 1, 2005), pp. 420-427, XP027766480, ISSN: 0141-3910 [retrieved on Jun. 1, 2005].
Extended European Search Report issued Dec. 9, 2022 for European Application No. 20796209.3.
Office Action mailed on Mar. 18, 2023 in CN 202080029473.8.

* cited by examiner

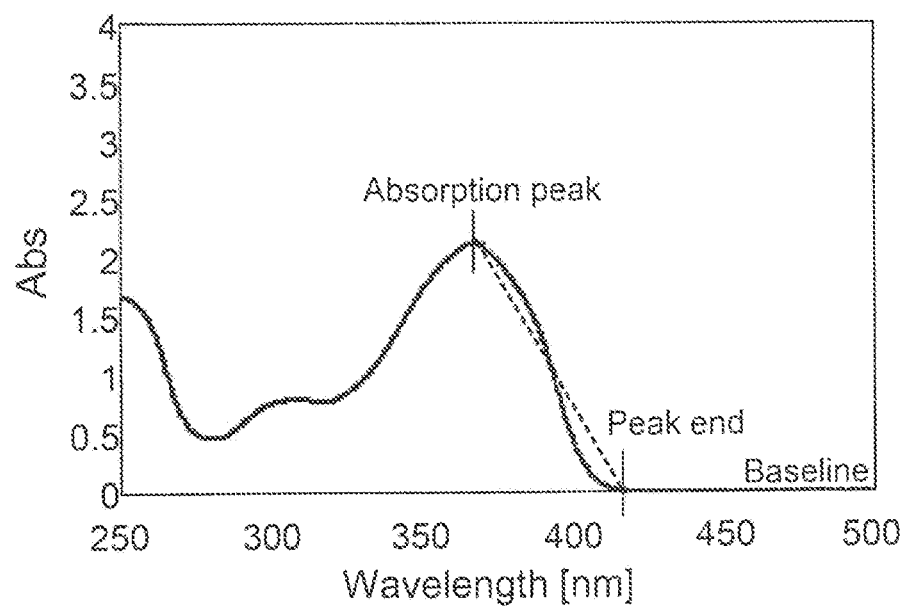

ULTRAVIOLET ABSORBER HAVING EXCELLENT HEAT RESISTANCE AND LONG-WAVELENGTH ABSORPTION

CROSS-REFERENCE TO RELATED APPLICATIONS

This application is a § 371 national phase entry of International Patent Application No. PCT/JP2020/017965, filed on Apr. 27, 2020, which claims priority to and the benefit of Japanese Patent Application No. 2019-086472, filed on Apr. 26, 2019, all of which are hereby incorporated herein by reference in their entireties.

TECHNICAL FIELD

The present invention relates to an ultraviolet absorber comprised of a benzotriazole compound.

BACKGROUND ART

Resin members deteriorate due to the action of ultraviolet rays, and cause quality deterioration such as discoloration and a decrease in mechanical strength, thereby inhibiting long-term use. An ultraviolet absorber is usually added to a resin member to avoid such quality deterioration, or control the wavelength of a transmitted light.

Conventionally, as an organic ultraviolet absorber, there are known, for example, benzotriazole-based, benzophenone-based, triazine-based, cyanoacrylate-based and salicylate-based ultraviolet absorbers.

The inventors of the present invention have proposed a 2-phenylbenzotriazole derivative having a sulfur-containing group, as an ultraviolet absorber capable of, in particular, efficiently and sufficiently absorbing harmful lights having a wavelength of 380 to 400 nm and suppressing the absorption of lights having a wavelength of not shorter than 400 nm which constitutes the cause of yellowing at early stages (Patent documents 1 and 2).

PRIOR ART DOCUMENTS

Patent Documents

Patent document 1: WO2016/021664
Patent document 2: WO2016/174788

SUMMARY OF THE INVENTION

Problems to be Solved by the Invention

An organic ultraviolet absorber is such that the ultraviolet absorber will undergo thermal decomposition when heating so as to mold and process a resin composition containing such ultraviolet absorber, thus causing the ultraviolet absorption capability of a resin member to deteriorate, the transparency thereof to be lost if the resin member is a transparent resin member, or even the inner region of a molding or processing device to be possibly contaminated; an organic ultraviolet absorber with a more excellent heat resistance is demanded. In Patent documents 1 and 2, as a sulfur-containing group of the 2-phenylbenzotriazole derivative, there is synthesized a sulfur-containing group with a hydrocarbon group composed of carbons and hydrogens, such as an aliphatic or aromatic hydrocarbon group, being bonded to sulfur at a base end; when used in a resin requiring a high processing temperature, there have been concerns that an ultraviolet absorption capability may deteriorate as the ultraviolet absorber decomposes, the transparency of a transparent resin member may be lost, a device may be contaminated at the time of processing, and odors may occur at the time of decomposition. For this reason, there is demanded an ultraviolet absorber that is superior in heat resistance, and is thus capable of being applied to a resin requiring an even higher processing temperature, preventing a device from being contaminated at the time of processing, and reducing the amount of odor which may occur.

Further, in recent years, it has been pointed out that in the sunlight, other than an ultraviolet light of a wavelength of 250 to 400 nm, lights in a visible light short-wavelength region of about 400 to 430 nm can also cause damages to organic substances and human body; a light absorber capable of absorbing even the lights in the visible light short-wavelength region is demanded. In Patent documents 1 and 2, as a sulfur-containing group of the 2-phenylbenzotriazole derivative, while there is synthesized a sulfur-containing group with a hydrocarbon group composed of carbons and hydrogens, such as an aliphatic or aromatic hydrocarbon group, being bonded to sulfur at a base end, absorption in the visible light short-wavelength region was insufficient. For this reason, there is demanded a light absorber capable of absorbing even lights in the visible light short-wavelength region, and efficiently absorbing a light having a target wavelength.

The present invention was made in view of the above circumstances: it is an object of the present invention to provide an ultraviolet absorber with a high molar extinction coefficient that is particularly superior in heat resistance odor suppression at the time of thermal decomposition and long-wavelength absorption, as compared to a conventional ultraviolet absorber.

Means to Solve the Problems

As a solution to the aforementioned problems, the ultraviolet absorber of the present invention is comprised of a 2-phenylbenzotriazole derivative having a bonding group represented by the following formula (I) or (II):

[Chemical formula 1]

wherein X represents a nitrogen atom, an oxygen atom or a residue obtained by eliminating a hydrogen atom from an amide group; l represents an integer of 0 or 1; $Y^1$ represents a substituted or unsubstituted aromatic hydrocarbon group; m is 1 when X is a nitrogen atom or a residue obtained by eliminating a hydrogen atom from an amide group, or 0 when X is an oxygen atom; $Y^2$ represents a hydrogen atom, a substituted or unsubstituted aliphatic hydrocarbon group, or a substituted or unsubstituted aromatic hydrocarbon group,

[Chemical formula 2]

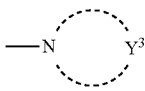

(II)

wherein $Y^3$ forms a substituted or unsubstituted hetero ring together with a nitrogen atom N.

Effects of the Invention

The ultraviolet absorber of the present invention has a high molar extinction coefficient, and is superior in heat resistance, odor suppression at the time of thermal decomposition and long-wavelength absorption, as a result of introducing into a benzotriazole skeleton a functional group having the bonding group represented by the formula (I) or (II).

BRIEF DESCRIPTION OF THE DRAWINGS

FIG. 1 is a reference diagram showing a gradient of an absorption peak on a long-wavelength side in a wavelength region of 350 to 430 nm of a UV-Vis absorption spectrum.

MODE FOR CARRYING OUT THE INVENTION

The present invention is described in detail hereunder.
[Substituent Group Etc.]

In the present invention, a substituent group includes groups capable of adjusting, for example, a heat resistance, absorption property, refractive index, melting point, light resistance and compatibility to resins, such as "a monovalent or divalent group(s) selected from a hydrocarbon group, unsaturated group, nitrogen-containing group, sulfur-containing group, oxygen-containing group, phosphorus-containing group and halogen atom." Examples of such substituent group are as follows.

As a hydrocarbon group, there may be listed, for example, an aliphatic hydrocarbon group, an alicyclic hydrocarbon group and an aromatic hydrocarbon group. The aliphatic hydrocarbon group may have hydrogen atoms therein substituted by, at least one of two ends thereof interrupted by, or carbon-carbon bonds therein interrupted by a monovalent or divalent group(s) selected from an alicyclic hydrocarbon group, aromatic hydrocarbon group, unsaturated group, nitrogen-containing group, sulfur-containing group, oxygen-containing group, phosphorus-containing group and halogen atom. Although not particularly limited, specific examples of the aliphatic hydrocarbon group include a methyl group, ethane-1-yl group, propane-1-yl group, 1-methylethane-1-yl group, butane-1-yl group, butane-2-yl group, 2-methylpropane-1-yl group, 2-methylpropane-2-yl group, pentane-1-yl group, pentane-2-yl group, 2-methylbutane-1-yl group, hexane-1-yl group, 2-methylpentane-1-yl group, 3-methylpentane-1-yl group, heptane-1-yl group, 3-ethylpentane-1-yl group, 2-methylhexane-yl group, 3-methylhexane-yl group, octane-1-yl group, 2-methylheptane-1-yl group, 3-methylheptane-1-yl group, 4-methylheptane-1-yl group, 2-ethylhexane-1-yl group, 3-ethylhexane-1-yl group, 1,1,3,3-tetramethylbutyl nonane-1-yl group, 3-ethylheptane-1-yl group, 4-ethylheptane-1-yl group, 2-methyloctane-1-yl group, 3-methyloctane-1-yl group, 4-methyloctane-1-yl group, decane-1-yl group, 4-propylheptane-1-yl group, 3-ethyloctane-1-yl group, 4-ethyloctane-1-yl group, undecane-1-yl group, dodecane-1-yl group, 2-methylundecane-1-yl group, 2-ethyldecane-1-yl group, tridecane-1-yl group, tetradecane-1-yl group, pentadecane-1-yl group, hexadecane-1-yl group, heptadecane-1-yl group and octadecane-1-yl group.

The alicyclic hydrocarbon group preferably has 3 to 10, more preferably 3 to 8 carbon atoms; and may have hydrogen atoms therein substituted by, at least one of two ends thereof interrupted by, or carbon-carbon bonds therein interrupted by a monovalent or divalent group(s) selected from an aliphatic hydrocarbon group, aromatic hydrocarbon group, unsaturated group, nitrogen-containing group, sulfur-containing group, oxygen-containing group, phosphorus-containing group and halogen atom. Although not particularly limited, examples of the alicyclic hydrocarbon group include a cyclopropyl group, cyclobutyl group, cyclopentyl group, cyclohexyl group, cycloheptyl group, cyclooctyl group, and groups containing these groups as skeletons.

The aromatic hydrocarbon group has an aromatic ring such as a benzene ring, naphthalene ring and anthracene ring; preferably has 6 to 18, more preferably 6 to 14 carbon atoms; and may have hydrogen atoms therein substituted by, at least one of two ends thereof interrupted by, or carbon-carbon bonds therein interrupted by a monovalent or divalent group(s) selected from an aliphatic hydrocarbon group, alicyclic hydrocarbon group, unsaturated group, nitrogen-containing group, sulfur-containing group, oxygen-containing group, phosphorus-containing group and halogen atom. Although not particularly limited, examples of a monovalent aromatic hydrocarbon group include a phenyl group, 2-methylphenyl group, 3-methylphenyl group, 4-methylphenyl group, 2,4-dimethylphenyl group, 2,5-dimethylphenyl group, 3,4-dimethylphenyl group, 3,5-dimethylphenyl group, 2,4,5-trimethylphenyl group, 2,4,6-trimethylphenyl group, 4-biphenyl group, 2-methoxyphenyl group, 3-methoxyphenyl group, 4-methoxyphenyl group, 2-ethoxyphenyl group, 3-ethoxyphenyl group, 4-ethoxyphenyl group, 2-chlorophenyl group, 2-fluorophenyl group, 4-fluorophenyl group, 2-trifluoromethylphenyl group, 4-trifluoromethylphenyl group, 1-naphthyl group, 2-naphthyl group, 1-anthracenyl group, 2-anthracenyl group and 9-anthracenyl group. Although not particularly limited, examples of a divalent aromatic hydrocarbon group include a 1,4-phenylene group, 1,3-phenylene group, 1,2-phenylene group, 1,8-naphthylene group, 2,7-naphthylene group, 2,6-naphthylene group, 1,4-naphthylene group, 1,3-naphthylene group, 9,10-anthracenylene group, 1,8-anthracenylene group, 2,7-anthracenylene group, 2,6-anthracenylene group, 1,4-anthracenylene group and 1,3-anthracenylene group.

The unsaturated group preferably has 1 to 10, more preferably 1 to 8 carbon atoms; and contains a carbon-carbon or carbon-hetero atom unsaturated bond(s) such as a carbon-carbon double bond, carbon-carbon triple bond, carbon-oxygen double bond (although not particularly limited, examples of which include a carbonyl group, aldehyde group, ester group, carboxy group, carbamate group, urea group, amide group, imide group, carbamoyl group and urethane group), carbon-nitrogen double bond (although not particularly limited, examples of which include an isocyanate group), and carbon-nitrogen triple bond (although not particularly limited, examples of which include a cyano group and cyanate group). Although not particularly limited, examples of the unsaturated group include an acryloyl group, methacryloyl group, maleic acid monoester group, styryl group, allyl group, vinyl group, alkenyl group, alkynyl group, carbonyl group, aldehyde group, ester group, carboxy group, carbamate group, urea group, amide group, imide group, carbamoyl group, cyano group, cyanate group, isocyanate group and urethane group.

The nitrogen-containing group preferably has 0 to 10 carbon atoms; and includes, for example, a cyano group, cyanate group, isocyanate group, nitro group, nitroalkyl group, amide group, urea, group, urethane group, imide group, carbodiimide group, azo group, pyridine group, imidazole group, amino group, primary amino group, secondary amino group, tertiary amino group, aminoalkyl group, 2-(2'-hydroxy-3'-tert-butyl-5'-methylphenyl)-5-aminobenzotriazole group, 3,4,5,6-tetrahydrophthalimidyl methyl group and 2-[6-(2H-benzotriazole-2-yl-)-4-(1,1,3,3-tetramethylbutyl) phenol-yl]-methyl group.

The sulfur-containing group preferably has 0 to 10 carbon atoms; and includes, for example, a thiophen group, thiazole group, thiol group, thioether group, thioalkoxy group, sulfo group, sulfide group, disulfide group, thioester group, thioamide group, sulfonyl group, sulfo group, thiocarbonyl group, thiourea group, thiocarbamate group or dithiocarbamate group.

The oxygen-containing group preferably has 6 to 12 carbon atoms, if the aromatic hydrocarbon group or alicyclic hydrocarbon group is contained; preferably has 0 to 18 carbon atoms, if the aromatic hydrocarbon group or alicyclic hydrocarbon group is not contained. Although not particularly limited, examples of the oxygen-containing group include a hydroxy group, alkoxy group, acetyl group, aldehyde group, carboxy group, ether group, carbonyl group, ester group, oxazole group, amide group, nitro group, morpholin group, carbamate group, carbamoyl group, polyoxyethylene group and oxo group.

The phosphorus-containing group includes a phosphine group, phosphite group, phosphonic acid group, phosphinic acid group, phosphoric acid group or phosphoric acid ester group. The phosphorus-containing group preferably has 6 to 22 carbon atoms, if the aromatic hydrocarbon group or alicyclic hydrocarbon group is contained; preferably has 0 to 6 carbon atoms, if the aromatic hydrocarbon group or alicyclic hydrocarbon group is not contained.

Examples of the halogen atom include a fluorine atom, chlorine atom, bromine atom and iodine atom.

In the present invention, a 2-phenylbenzotriazole derivative is, for example, represented by the following formula (A).

[Chemical formula 3]

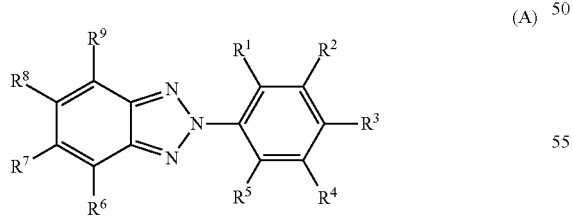

(A)

In the formula (A), each of $R^1$ to $R^9$ independently represents a monovalent or divalent group selected from the bonding group represented by the above formula (I) or (II), a hydrogen atom, a hydrocarbon group, an unsaturated group, a nitrogen-containing group, a sulfur-containing group, an oxygen-containing group, a phosphorus-containing group and a halogen atom. At least one of $R^1$ to $R^9$ is the bonding group represented by the above formula (I) or (11).

In the above formula (A), there are no particular restrictions on a substitution position(s) of the bonding group represented by the above formula (I) or (11). The substitution position(s) may be any one of $R^1$ to R; preferred are $R^6$ to $R^9$, and more preferred are $R^7$ and $R^8$. There are also no particular restrictions on a substitution number of the bonding group represented by the above formula (I) or (II); the substitution number may, for example, be 1 to 2, preferably 1.

As the above substituent group, there may be listed, for example, the monovalent or divalent groups described in the above section titled "[Substituent group etc.]." When the above substituent group is a divalent group, any two of (preferably any adjacent two of) $R^1$ to $R^9$ may together form a ring. These substituent groups may further have hydrogen atoms therein substituted by, at least one of two ends thereof interrupted by, or carbon-carbon bonds therein interrupted by a monovalent or divalent group(s) selected from the above-exemplified unsaturated group, nitrogen-containing group, sulfur-containing group, oxygen-containing group, phosphorus-containing group and halogen atom.

In the above formula (A), when the bonding group represented by the formula (I) or (II) is present at $R^7$ or $R^8$, it is preferred that the rest of $R^6$ to $R^9$ where the bonding group represented by the formula (I) or (II) is not present all represent hydrogen atoms. Further, preferable examples of combinations of $R^1$, $R^2$, $R^3$, $R^4$ and $R^5$ are as follows.

[1] Substituent group(s) selected from a hydrocarbon group that has 1 to 18 carbon atoms (including a hydrocarbon group that has 2 to 18 carbon atoms, such as an alkenyl group and alkynyl group); a hydroxy group, an aromatic hydrocarbon group that has 6 to 18 carbon atoms; an ether group that has 1 to 18 carbon atoms; an alkoxy group that has 1 to 18 carbon atoms; an ester group that has 1 to 18 carbon atoms; a (meth)acryloyloxy group; a polyoxyethylene group that has 1 to 20 carbon atoms and may have these substituent groups bonded thereto; or a hydrocarbon group that has 1 to 18 carbon atoms and may have hydrogen atoms therein substituted by, a base end(s) thereof interrupted by, or carbon-carbon bonds therein interrupted by these substituent groups, where if two or more of $R^1$, $R^2$, $R^3$, $R^4$ and $R^5$ are substituent groups, there are independently contained one or more of the above-listed types of substituent groups.

[2] In [1], the substituent group(s) is at least one selected from a hydrocarbon group having 1 to 10 carbon atoms and a hydroxy group.

[3] In [2], the substituent group(s) is at least one selected from a hydrocarbon group having 1 to 6 carbon atoms and a hydroxy group.

[4] In any one of [1] to [3], the hydrocarbon group as the substituent group(s) is a linear or branched alkyl group.

[5] In [4], the substituent group(s) is at least one selected from a methyl group, t-butyl group and hydroxy group.

[6] In [5], the substituent group(s) is at least one selected from a methyl group, t-butyl group and hydroxy group, where the number of the hydroxy groups is one or less.

[7] In [5], there is at least one methyl group as the substituent group(s).

[8] In any one of [1] to [7], the number of the substituent groups is 1 to 4, preferably 2 to 4.

[9] In any one of [1] to [8], the substituent group(s) is present at any one of the positions of $R^1$ to $R^4$, where the rest of $R^1$ to $R^5$ are hydrogen atoms.

[10] In any one of [1] to [9], the substituent group(s) is present at any one of the positions of $R^1$, $R^2$ and $R^4$, where the rest of $R^1$ to $R^5$ are hydrogen atoms.

[11] In [10], $R^1$ is a hydroxy group, $R^2$ is a t-butyl group, $R^4$ is a methyl group, and $R^3$ and $R^5$ are hydrogen atoms.

(Bonding Group Represented by the Above Formula (I) or (II))

In the bonding group represented by the above formula (I), X represents a nitrogen atom, an oxygen atom or a residue obtained by eliminating a hydrogen atom from an amide group; l represents an integer of 0 or 1. In the formula (I), when X is a residue obtained by eliminating a hydrogen atom from an amide group, it represents —C(=O)—N< or >N—C(=O)—. $Y^1$ represents a substituted or unsubstituted aromatic hydrocarbon group; m is 1 when X is a nitrogen atom or a residue obtained by eliminating a hydrogen atom from an amide group, or 0 when X is an oxygen atom. $Y^2$ represents a hydrogen atom, a substituted or unsubstituted aliphatic hydrocarbon group, or a substituted or unsubstituted aromatic hydrocarbon group.

The aromatic hydrocarbon groups represented by $Y^1$ and $Y^2$ are each composed of a single ring or condensed ring; and each preferably have 6 to 18, more preferably 6 to 14 carbon atoms. Although not particularly limited, examples of such aromatic hydrocarbon groups include a phenyl group, naphthyl group and anthracenyl group.

The aliphatic hydrocarbon group represented by $Y^2$ preferably has 1 to 20, more preferably 1 to 10 carbon atoms, examples of which include a linear or branched alkyl group, a linear or branched alkenyl group, a linear or branched alkynyl group, and an alicyclic hydrocarbon group. Although not particularly limited, examples of the aliphatic hydrocarbon group include a methyl group, ethane-1-yl group, propane-1-yl group, 1-methylethane-1-yl group, butane-1-yl group, butane-2-yl group, 2-methylpropane-1-yl group, 2-methylpropane-2-yl group, pentane-1-yl group, pentane-2-yl group, 2-dimethylbutane-1-yl group, hexane-1-vi group, 2-methylpentane-1-yl group, 3-methylpentane-1-yl group, heptane-1-yl group, 3-ethylpentane-1-yl group, 2-methylhexane-yl group, 3-methylhexane-yl group, octane-1-yl group, 2-methylheptane-1-yl group, 3-methylheptane-1-yl group, 4-methylheptane-1-yl group, 2-ethylhexane-1-yl group, 3-ethylhexane-1-yl group, 1,1,3,3-tetramethylbutyl nonane-1-yl group, 3-ethylheptane-1-yl group, 4-ethylheptane-1-yl group, 2-methyloctane-1-yl group, 3-methyloctane-1-yl group, 4-methyloctane-1-yl group, decane-1-yl group, 4-propylheptane-1-yl group, 3-ethyloctane-1-yl group, 4-ethyloctane-1-yl group, undecane-1-yl group, dodecane-1-yl group, 2-methylundecane-1-yl group, 2-ethyldecane-1-yl group, tridecane-1-yl group, tetradecane-1-yl group, pentadecane-1-yl group, hexadecane-1-yl group, heptadecane-1-yl group and octadecane-1-yl group. Even among these examples, preferred is a linear or branched alkyl group having 1 to 8 carbon atoms, more preferred is a linear or branched alkyl group having 1 to 4 carbon atoms. Further, as for a cyclic hydrocarbon group, it is preferred that the number of the carbon atoms be 3 to 10, more preferably 3 to 8. There may be listed a cyclopropyl group, cyclobutyl group, cyclopentyl group, cyclohexyl group, cycloheptyl group, cyclooctyl group, and groups containing these groups as skeletons.

Although not particularly limited, examples of substituent group(s) of $Y^1$, $Y^2$ may include the monovalent or divalent groups described in the section titled "[Substituent group etc.]." When the substituent group(s) is a divalent group, any two of (preferably any adjacent two of) the carbon atoms in the above aromatic hydrocarbon group or aliphatic hydrocarbon group may together form a ring.

Preferable examples are as follows.

In terms of heat resistance and a molar extinction coefficient at the maximum absorption peak in a wavelength region of 350 to 430 nm, preferable examples of the bonding group represented by the formula (I) are as follows.

(1-1) The bonding group is represented by the formula (I). In the formula (I), l is 1, X is an oxygen atom.

(1-2) The bonding group is represented by the formula (I). In the formula (I), l is 0 or 1; when l is 1, X is a nitrogen atom.

(1-3) The bonding group is represented by the formula (I). In the formula (I), l is 1, X is a nitrogen atom, and a molecular weight of $Y^1$ is not smaller than 190.

(1-4) The bonding group is represented by the formula (I). In the formula (I), l is 0 or 1; when l is 1, X is an oxygen atom, and $Y^1$ contains an oxygen-containing group(s).

(1-5) The bonding group is represented by the formula (I). In the formula (I), l is 1, X is a nitrogen atom, and $Y^2$ is a hydrogen atom or a substituted or unsubstituted aromatic hydrocarbon group.

(1-6) The bonding group is represented by the formula (I). In the formula (I), $Y^1$ has a substituent group(s) in the aromatic hydrocarbon group, and a base end of such substituent group(s) is an ester group or amide group; l is 0 or 1; when l is 1, X is a nitrogen atom.

(1-7) The bonding group is represented by the formula (I). In the formula (I), $Y^1$ has a substituent group(s) in the aromatic hydrocarbon group, and such substituent group(s) includes at least one kind of group selected from a hydroxyl group and a (meth)acryloyl group. Preferably, such substituent group(s) are a hydroxyalkyl group (having, for example, 1 to 10 carbon atoms), a (meth)acryloyl group, or an alkyl group whose end is substituted by a (meth)acryloyl group (the alkyl group has, for example, 1 to 10 carbon atoms).

(1-8) The bonding group is represented by the formula (I). In the formula (I), l is 1, X is a nitrogen atom, and $Y^1$ contains a bicyclic or more complex (e.g. tetracyclic or less complex, though no particular restrictions are imposed on the upper limit) condensed ring skeleton bonded to a sulfur-containing group. Although not particularly limited, the condensed ring skeleton may, for example, be a benzotriazole skeleton. Preferably, $Y^1$ has a substituent group(s) in the aromatic hydrocarbon group (preferably, phenyl group), and such substituent group(s) includes the aforementioned sulfur-containing group. More preferably, the base end of such substituent group(s) is the aforementioned sulfur-containing group.

(1-9) The bonding group is represented by the formula (I). In the formula (I), l is 1, X is a nitrogen atom; and $Y^1$ is such that the aromatic hydrocarbon group is a bicyclic or more complex condensed ring, or that a substituent group(s) is present in the aromatic hydrocarbon group, and such substituent group(s) and the aromatic hydrocarbon group together form a ring(s).

Further, in addition to any of the above examples, it is more preferred that there are three or more substituent groups in any one of $R^1$ to $R^4$ in the formula (A), in terms of heat resistance and the molar extinction coefficient at the maximum absorption peak in the wavelength region of 350 to 430 nm.

In terms of heat resistance and the molar extinction coefficient at the maximum absorption peak in the wavelength region of 350 to 430 nm, preferable examples of the bonding group represented by the formula (II) are as follows.

(2-1) The bonding group is represented by the formula (II). In the formula (II), a hetero ring is polycyclic (e.g. bicyclic to tetracyclic, though not particularly limited).

Further, in addition to the above example, in terms of heat resistance, it is more preferred that there are three or more substituent groups in any one of $R^1$ to $R^4$ in the formula (A).

In terms of long-wavelength absorption, preferable examples of the bonding group represented by the formula (I) are as follows.

(3-1) The bonding group is represented by the formula (I). In the formula (I), l is 1, X is a nitrogen atom, $Y^2$ is a hydrogen atom, and an oxygen-containing group or nitrogen-containing group is present in $Y^1$.

(3-2) The bonding group is represented by the formula (I). In the formula (I), l is 1, X is a nitrogen atom; $Y^2$ is a substituted or unsubstituted aliphatic hydrocarbon group, or a substituted or unsubstituted aromatic hydrocarbon group.

(3-3) The bonding group is represented by the formula (I). In the formula (I), l is 1, and X is a nitrogen atom or a residue obtained by eliminating a hydrogen atom from an amide group.

In terms of a gradient of the maximum absorption peak on the long-wavelength side in the wavelength region of 350 to 430 nm, preferable examples of the bonding group represented by the formula (I) or (II) are as follows.

(4-1) The bonding group is represented by the formula (I). In the formula (I), l is 1, X is a nitrogen atom, $Y^1$ is a monocyclic and unsubstituted aromatic hydrocarbon group (preferably, phenyl group), and Y is a hydrogen atom or a substituted or unsubstituted aliphatic hydrocarbon group.

(4-2) The bonding group is represented by the formula (I). In the formula (I), l is 1, X is a nitrogen atom, and $Y^1$ contains a bicyclic or more complex condensed ring (e.g. tetracyclic or less complex, though no particular restrictions are imposed on the upper limit). The condensed ring may be that containing the aforementioned aromatic hydrocarbon group, or that contained in the substituent group(s) of such aromatic hydrocarbon group (in the latter case, there may be listed, for example, a benzotriazole skeleton). $Y^1$ preferably contains a bicyclic or more complex condensed ring directly bonded to the nitrogen atom represented by X. The condensed ring is preferably tricyclic or more complex. Preferably, the condensed ring has two or more six-membered rings. The six-membered ring is preferably an aromatic hydrocarbon group (more preferably, phenyl group).

(4-3) The bonding group is represented by the formula (I). In the formula (I), l is 1, X is a nitrogen atom; $Y^1$ contains a condensed ring having at least one six-membered ring (e.g. a bicyclic to tetracyclic condensed ring, though not particularly limited). The condensed ring may be that containing the aforementioned aromatic hydrocarbon group, or that contained in the substituent group(s) of such aromatic hydrocarbon group (in the latter case, there may be listed, for example, a benzotriazole skeleton). Preferably, the condensed ring has two or more six-membered rings. The six-membered ring is preferably an aromatic hydrocarbon group (more preferably, phenyl group).

(4-4) The bonding group is represented by the formula (I). In the formula (I), l is 1, X is a nitrogen atom; Y contains a condensed ring (e.g. bicyclic to tetracyclic, though not particularly limited) having an oxygen-containing group as the substituent group(s). The condensed ring may or may not contain the aforementioned aromatic hydrocarbon group in its skeleton. Preferably, the condensed ring contains such aromatic hydrocarbon group in its skeleton.

(4-5) The bonding group is represented by the formula (II). In the formula (II), the hetero ring is polycyclic (e.g. bicyclic to tetracyclic, though not particularly limited).

(4-6) The bonding group is represented by the formula (II). In the formula (II), the hetero ring has at least one six-membered ring (e.g. monocyclic to tetracyclic, though not particularly limited). Preferably, the hetero ring has two or more six-membered rings. The six-membered ring is preferably an aromatic hydrocarbon group (preferably, phenyl group).

(4-7) The bonding group is represented by the formula (II). In the formula (II), the hetero ring has at least one five-membered ring (e.g. monocyclic to tetracyclic, though not particularly limited). Preferably, the hetero ring is bicyclic or more complex.

(4-8) The bonding group is represented by the formula (I). In the formula (I), l is 0, and $Y^1$ is a substituted or unsubstituted aromatic hydrocarbon group (preferably, phenyl group). Preferably. $Y^1$ does not have a substituent group(s), or has an oxygen-containing group or nitrogen-containing group as the substituent group(s). More preferably, $Y^1$ has an oxygen-containing group as the substituent group(s).

(4-9) The bonding group is represented by the formula (I). In the formula (I), l is 1, X is a nitrogen atom, and $Y^1$ contains a bicyclic or more complex (e.g. tetracyclic or less complex, though no particular restrictions are imposed on the upper limit) condensed ring skeleton bonded to a sulfur-containing group. Although not particularly limited, the condensed ring skeleton may, for example, be a benzotriazole skeleton. Preferably, Y has a substituent group(s) in the aromatic hydrocarbon group (preferably, phenyl group), and such substituent group(s) includes the aforementioned sulfur-containing group. More preferably, the base end of such substituent group(s) is the aforementioned sulfur-containing group.

(4-10) The bonding group is represented by the formula (I). In the formula (I), l is 1, X is a nitrogen atom; $Y^1$ has a substituent group(s) in the aromatic hydrocarbon group (preferably, phenyl group), and such substituent group(s) includes a hydroxy group, preferably a hydroxyalkyl group (the number of the carbon atoms is, for example, 1 to 10).

(4-11) The bonding group is represented by the formula (I). In the formula (I), l is 1. X is a nitrogen atom; $Y^1$ has a substituent group(s) in the aromatic hydrocarbon group (preferably, phenyl group), and such substituent group(s) includes a (meth)acryloyl group, preferably a (meth)acryloyl group or an alkyl group whose base end is substituted by a (meth)acryloyl group (the alkyl group has, for example, 1 to 10 carbon atoms).

In terms of compatibility to resins, preferable examples of the bonding group represented by the formula (I) or (II) are as follows.

(5-1) The bonding group is represented by the formula (I). In the formula (I), l is 0, and $Y^1$ is a substituted or unsubstituted aromatic hydrocarbon group (preferably, phenyl group).

(5-2) The bonding group is represented by the formula (II). In the formula (II), the hetero ring is polycyclic (e.g. bicyclic to tetracyclic, though not particularly limited).

(5-3) The bonding group is represented by the formula (II). In the formula (II), the hetero ring has at least one six-membered ring (e.g. monocyclic to tetracyclic, though not particularly limited). Preferably, the hetero ring has two or more six-membered rings. The six-membered ring is preferably an aromatic hydrocarbon group (more preferably, phenyl group).

(5-4) The bonding group is represented by the formula (II). In the formula (II), the hetero ring has at least one five-membered ring (e.g. monocyclic to tetracyclic, though not particularly limited). Preferably, the hetero ring is bicyclic or more complex.

Further, in addition to the above examples, it is preferred that at least one of $R^1$ to $R^5$ in the formula (A) be a methyl group. Preferably. $R^4$ is a methyl group.

In terms of light resistance, preferable examples of the bonding group represented by the formula (I) or (II) are as follows.

(6-1) The bonding group is represented by the formula (I). In the formula (I), l is 1, X is a nitrogen atom, and $Y^1$ contains a bicyclic or more complex (e.g. tetracyclic or less complex, though no particular restrictions are imposed on the upper limit) condensed ring. The condensed ring may be that containing the aforementioned aromatic hydrocarbon group, or that contained in the substituent group(s) of such aromatic hydrocarbon group (in the latter case, there may be listed, for example, a benzotriazole skeleton). $Y^1$ preferably contains a bicyclic or more complex condensed ring directly bonded to the nitrogen atom represented by X. The condensed ring is preferably tricyclic or more complex. Preferably, the condensed ring has two or more six-membered rings. The six-membered ring is preferably an aromatic hydrocarbon group (more preferably, phenyl group).

(6-2) The bonding group is represented by the formula (I). In the formula (I), l is 1, X is a nitrogen atom, and $Y^1$ has a condensed ring skeleton containing at least one six-membered ring (e.g. bicyclic to tetracyclic, though not particularly limited). Preferably, $Y^1$ has a condensed ring containing the aforementioned aromatic hydrocarbon group in its skeleton. The condensed ring preferably has two or more six-membered rings. The six-membered ring is preferably an aromatic hydrocarbon group (more preferably, phenyl group).

(6-3) The bonding group is represented by the formula (I). In the formula (I), l is 1. X is a nitrogen atom; $Y^1$ contains a condensed ring (e.g. bicyclic to tetracyclic, though not particularly limited) having an oxygen-containing group as the substituent group(s). The condensed ring may or may not contain the aforementioned aromatic hydrocarbon group in its skeleton. Preferably, the condensed ring contains such aromatic hydrocarbon group in its skeleton.

(6-4) The bonding group is represented by the formula (II). In the formula (II), the hetero ring contains an unsaturated bond (preferably, double bond).

(6-5) The bonding group is represented by the formula (II). In the formula (II), the hetero ring is polycyclic (e.g. bicyclic to tetracyclic, though not particularly limited).

(6-6) The bonding group is represented by the formula (II). In the formula (II), the hetero ring has at least one six-membered ring (e.g. monocyclic to tetracyclic, though not particularly limited). Preferably, the hetero ring has two or more six-membered rings. The six-membered ring is preferably an aromatic hydrocarbon group (more preferably, phenyl group).

(6-7) The bonding group is represented by the formula (II). In the formula (II), the hetero ring has at least one five-membered ring (e.g. monocyclic to tetracyclic, though not particularly limited). Preferably, the hetero ring is bicyclic or more complex.

(6-8) The bonding group is represented by the formula (I). In the formula (I), l is 0, and Y is a substituted or unsubstituted aromatic hydrocarbon group (preferably, phenyl group). Preferably, $Y^1$ does not have a substituent group(s), or has an oxygen-containing group or nitrogen-containing group as the substituent group(s). More preferably, $Y^1$ has an oxygen-containing group or nitrogen-containing group as the substituent group(s).

(6-9) The bonding group is represented by the formula (I). In the formula (I), l is 1, X is a nitrogen atom, and $Y^1$ contains a bicyclic or more complex (e.g. tetracyclic or less complex, though no particular restrictions are imposed on the upper limit) condensed ring skeleton bonded to a sulfur-containing group. Although not particularly limited, the condensed ring skeleton may, for example, be a benzotriazole skeleton. Preferably, $Y^1$ has a substituent group(s) in the aromatic hydrocarbon group (preferably, phenyl group), and such substituent group(s) includes the aforementioned sulfur-containing group. More preferably, the base end of such substituent group(s) is the aforementioned sulfur-containing group.

Further, in addition to the above examples, it is preferred that at least one of $R^1$ to $R^5$ in the formula (A) be a methyl group. Preferably, $R^4$ is a methyl group.

It is preferable to contain a reactive substituent group(s) in the bonding group represented by the formula (I) or (II) and/or in the formula (A) in that if the ultraviolet absorber is added to an organic or inorganic material before use, the ultraviolet absorber shall, for example, bond to the organic or inorganic material to prevent bleed-out or the like and ensure a strength of the organic material. There are no particular restrictions on a reactive substituent group(s) as long as the substituent group(s) is capable of reacting with the functional groups present in the organic or inorganic materials. Examples of such reactive substituent group(s) include an isocyanate group, an epoxy group, a carboxy group, a carbonyl group, a hydroxy group, an alkenyl group, an alkynyl group, an ether group, a thioisocyanate group, a thioepoxy group, a thiocarboxylic acid group, a thiocarbonyl group, a thiol group, an amino group, a vinyl group, a vinyloxy group, an allyl group, a (meth)acryloyl group, a maleoyl group, a styryl group, a cinnamoyl group, hydrocarbon groups with these groups bonded thereto (e.g. carbon number 1 to 20. An alkyl group is preferred.), and polyoxyalkylene groups with these groups bonded thereto (e.g. carbon number 1 to 20); preferred are, for example, a hydroxy group, a (meth)acryloyl group, hydrocarbon groups with these groups bonded thereto, and polyoxyalkylene groups with these groups bonded thereto. For example, in the bonding group represented by the above formula (I), it is preferred that the reactive substituent group(s) be contained in the aromatic hydrocarbon group represented by $Y^1$; in terms of reactivity, it is more preferred that there be employed an aromatic hydrocarbon group with an alkyl group having a reactive substituent group at its end being bonded to an aromatic.

As a preferable example, the bonding group is represented by the formula (I); and in the formula (I), 1 is 1, X is a nitrogen atom, and $Y^1$ has a reactive substituent group(s) in the aromatic hydrocarbon group.

In the bonding group represented by the above formula (II), $Y^3$ forms a substituted or unsubstituted hetero ring together with a nitrogen atom N. As an atom(s) composing the ring of such hetero ring, other than a nitrogen atom and carbon atom there may also be listed hetero atoms such as a sulfur atom, nitrogen atom and oxygen atom; it is preferred that the hetero ring be such that the hetero atom is at least one selected from a nitrogen atom and oxygen atom; it is more preferred that the hetero ring be such that the hetero atom is a nitrogen atom. Further, a bicyclic or more complex condensed ring is even more preferred.

Although not particularly limited, specific examples thereof include aziridine, 1H-azirine, pyrrole, pyrrolidine, piperidine, hexamethyleneimine, azatropylidene, azocan, azonan, azonine, pyrazole, imidazoline, morpholine, thiazine, triazole, tetrazole, carbazole, phenazine, phenoxazine, phenothiazine, pyrroline, indole, isoindole, benzoimidazole, purine, benzotriazole, porphyrin, chlorin, choline, adenine, guanine, cytosine, thymine, uracil, pyrrolidone and imidazole, among which preferred are pyrrole, carbazole, piperidine, indole and phenothiazine, more preferred are pyrrole, carbazole and indole, even more preferred are carbazole and indole, particularly preferred is carbazole.

It is desired that an ultraviolet absorber have a high thermal decomposition temperature because an ultraviolet absorber with a low thermal decomposition temperature will decompose, and thus fail to sufficiently exhibit an ultraviolet absorption effect, or even contaminate a device, when reacted, mixed and kneaded with an organic substance such as a resin and an inorganic substance under a heated condition, or when an ultraviolet absorber-containing resin member is processed and molded by heating, where if the resin member employed is a transparent resin member, a loss in transparency needs to be prevented as well. Further, in terms of suppressing an odor at the time of thermal decomposition (oxidative decomposition), it is desired that there be contained no sulfur atom which causes the odor. The ultraviolet absorber of the present invention is such that a heat resistance thereof is improved by introducing the bonding group represented by the formula (I) or (II) into a 2-phenylbenzotriazole derivative. A 5% weight reduction temperature of the 2-phenylbenzotriazole derivative in the present invention is preferably not lower than 250° C., more preferably not lower than 280° C., even more preferably not lower than 300° C., particularly preferably not lower than 340° C. Since this 5% weight reduction temperature is higher than a temperature of 100 to 250° C. which is the softening temperature of a general resin ("Easily understandable plastics" editorial supervisor: The Japan Plastics Industry Federation, publisher: Nippon Jitsugyo Publishing), the ultraviolet absorber of the present invention can be applied not only to a thermosetting resin or thermoplastic resin having a molding process temperature of 100 to 200° C., but also to a thermoplastic resin requiring a molding process temperature that is even higher than a temperature of 200 to 250° C.

It has been pointed out that in addition to an ultraviolet light of a wavelength of 250 to 400 nm in the sunlight, lights in a visible light short-wavelength region of about 400 to 430 nm can also cause damages to organic substances (e.g. protection of a general organic resin composition and a blue light-emitting element in an organic EL display device such as a display) and human body; and even in the field of LED illumination likewise, there has been demanded a light absorber capable of absorbing even lights in the visible light short-wavelength region. Therefore, it is preferred that in a long-wavelength region of 380 to 430 nm, an absorption peak be present at a wavelength of not shorter than 355 nm, more preferably not shorter than 370 nm, even more preferably not shorter than 390 nm, particularly preferably not shorter than 400 nm.

Further, when absorbing a visible light of 400 to 430 nm, in order to inhibit, for example, a deterioration in the appearance of a resin member (e.g. yellowing), a deterioration in the display colors of a display, and a deterioration in the emission color of an LED, it is preferable to pass lights of a wavelength of greater than 430 nm through. In such case, although there are various standards, for example, a transmittance at 400 nm is preferably not higher than 10, more preferably not higher than 1%; a transmittance at 430 nm is preferably not higher than 75%; a transmittance at 440 nm is preferably not lower than 53%, more preferably not lower than 75%. While an absorption region required as well as a wavelength of an absorption peak required therewith vary depending on fields, the selectivity of an absorption wavelength and an absorption efficiency are critical in many fields. When focusing on the shape of an absorption peak, a sharp absorption peak with a large absorption peak gradient indicates that a light of a particular wavelength can be selectively absorbed; an absolute value of a gradient of a wavelength at the maximum absorption peak in the wavelength region of 350 to 430 nm that is measured with chloroform at 50 μM or 100 μM is preferably not smaller than 0.015, more preferably not smaller than 0.020, even more preferably not smaller than 0.025, particularly preferably not smaller than 0.030, more particularly preferably not smaller than 0.034. When the absolute value is within these ranges, lights of the wavelength of 400 to 430 nm can be selectively absorbed. Further, in order to efficiently absorb lights in such wavelength region, a molar extinction coefficient at the maximum absorption peak in the wavelength region of 350 to 430 nm that is measured with chloroform at 50 μM or 100 μM is preferably not smaller than 17,200 L/(mol·cm), more preferably not smaller than 18,000 L/(mol·cm), even more preferably not smaller than 20,000 L/(mol·cm), particularly preferably not smaller than 30,000 L/(mol·cm).

Light resistance is critical in terms of inhibiting a deterioration in an ultraviolet absorber as well as a deterioration in an organic material, inorganic material composition or organic resin composition containing such ultraviolet absorber; in the case of the ultraviolet absorber of the present invention, differences in transmittance at 370, 380, 390, 400, 410, 420 and 430 nm after performing irradiation for 100 hours under a condition(s) described in (7) Evaluation of light resistance in working examples below (e.g., wavelength 300 to 400 nm, irradiance 42 W/m$^2$, black panel temperature 63° C.) are all preferably not higher than 76%, more preferably not higher than 45%, even more preferably not higher than 30%, particularly preferably not higher than 15%, more particularly preferably not higher than 10%, most preferably not higher than 5%.

In the abovementioned ultraviolet absorption properties, the molar extinction coefficient affects the amount of the ultraviolet absorber added; the larger the value of the molar extinction coefficient is, the more efficiently a light of a desired wavelength can be absorbed. Further, when the gradient of an absorption peak is large, a light in a desired wavelength region can be selectively absorbed without absorbing a light(s) in the long-wavelength region. For example, in certain fields where inhibition of visible light absorption is required, even after adding the ultraviolet absorber of the present invention to absorb lights of the wavelength of 400 to 430 nm, coloring of a material such as yellowing of a material can still be inhibited. Further, the ultraviolet absorber of the present invention that has a superior light resistance also has a durability, and is thus remarkably useful.

The 2-phenylbenzotriazole derivative in the present invention has a favorable compatibility to resins, where the substituent group(s) at $R^1$ to $R^5$ are preferably linear or branched alkyl groups having 1 to 6 carbon atoms, more preferably methyl groups or t-butyl groups; or even more preferably, there is contained at least one methyl group. Further, the position thereof is preferably at $R^2$, $R^4$.

(Composition)

In this specification, the term "composition" includes a composition containing the ultraviolet absorber of the present invention regardless of a property thereof such as whether the composition is solid, fluid, gel-like or sol-like; a member containing the ultraviolet absorber of the present invention; and a raw material for producing such member.

In this specification, although not particularly limited, the term "member" includes, for example, an object having any shape. Uses of a composition such as a member containing the ultraviolet absorber of the present invention include, for example, those described later.

As a material of a composition containing the ultraviolet absorber of the present invention, there can be listed an organic material and an inorganic material. The ultraviolet absorber of the present invention has a high affinity, compatibility and adhesiveness to various organic and inorganic materials so that as a result of mixing, dissolving, dispersing, applying or performing coating using the ultraviolet absorber of the present invention, there can be obtained an uninform composition or member: particularly, when employing a transparent member, there can be obtained a member superior in transparency. Especially, the ultraviolet absorber of the present invention has a high applicability to an organic material.

A composition containing the ultraviolet absorber of the present invention includes an organic material composition and an inorganic material composition (in the present invention, a composition is referred to as an organic material composition if containing an organic material(s), and as an inorganic material composition if containing an inorganic material(s); they are collectively referred to as an organic material- or inorganic material-containing organic material or inorganic material composition). There are no particular restrictions on the shapes of these organic material composition and inorganic material composition, examples of which may include the shapes of a coating film, a coated film, a laminated film, a film, a sheet, a plate, a powdery product, a granular product, a pellet-shaped product, a tablet-shaped product and a molded product.

In the organic material composition and inorganic material composition that contain the ultraviolet absorber of the present invention, the ultraviolet absorber of the present invention assists in obtaining an organic material composition and an inorganic material composition that are superior in heat resistance, thus suppressing deterioration. Further, the ultraviolet absorber of the present invention has a favorable affinity for an organic material and an inorganic material, especially for an organic material.

Due to the aforementioned properties of the ultraviolet absorber of the present invention, an organic or inorganic material composition containing the same can be an organic or inorganic material composition superior in heat resistance, capable of efficiently absorbing harmful lights in a wavelength region of 250 to 430 nm, and, for example, being superior in appearance and capable of suppressing a deterioration in an ultraviolet absorption capability as the ultraviolet absorber decomposes, a loss in the transparency of a composition, a contamination of a device at the time of processing, and an occurrence of an odor as decomposition takes place, even under a high processing temperature.

The organic material composition contains an organic material(s) by an amount of not smaller than 0.001% by mass, preferably not smaller than 0.01% by mass, more preferably not smaller than 0.1% by mass, even more preferably not smaller than 1% by mass, per a total amount of all the ingredients other than water and a solvent.

The inorganic material composition contains an inorganic material(s) by an amount of not smaller than 0.001% by mass, preferably not smaller than 0.01% by mass, more preferably not smaller than 0.1% by mass, even more preferably not smaller than 1% by mass, per a total amount of all the ingredients other than water and a solvent.

The composition containing the ultraviolet absorber of the present invention may also be that with a raw mater al(s) for eventually forming an organic material, inorganic material, member or the like being added and mixed thereinto. Further, the composition containing the ultraviolet absorber of the present invention may also be that with the organic or inorganic material composition containing the ultraviolet absorber of the present invention being dispersed, dissolved and/or mixed in a liquid such as water and an organic solvent.

There are no particular restrictions on the organic material(s), examples of which may include organic resins, materials derived from animals and plants, materials derived from crude oil and organic compounds.

In the present invention, an organic resin composition is an organic composition containing the ultraviolet absorber of the present invention and an organic resin, and shall be included in the organic material composition.

There are no particular restrictions on the organic resin, conventionally known organic resins can be widely used, examples of which may include a thermoplastic resin and a thermosetting resin each including polymers having one kind of repeating unit as well as copolymers having multiple kinds of repeating units.

As for each individual type of resin(s) exemplified below, the term "thermoplastic resin (polymer and copolymer) and thermosetting resin (polymer and copolymer)" in this specification allows there to be contained other kind(s) of repeating units by an amount of not larger than 20% by mass, preferably not larger than 15% by mass, more preferably not larger than 10% by mass, even more preferably not larger than 5% by mass, particularly preferably not larger than 2% by mass, per a total amount of each corresponding resin, in addition to the kind of repeating unit unique to such resin as defined by the general term thereof. Further, it is allowed that there be employed a mixture of such corresponding resin and an other type of resin so that the other type of resin is contained by an amount of not larger than 20% by mass, preferably not larger than 15% by mass, more preferably not larger than 10% by mass, even more preferably not larger than 5% by mass, particularly preferably not larger than 2% by mass, per a total amount of the mixture.

There are no particular restrictions on the thermoplastic resin, examples of which may include polymers such as a (meth)acryl-based resin, olefin-based resin, styrene-based resin, ester-based resin, ether-based resin, vinyl chloride-based resin, fluorocarbon-based resin, vinyl-based resin, polycarbonate-based resin, polyamide-based resin, polyimide-based resin, polyamideimide-based resin, polymaleimide-based resin, polyvinylpyrrolidone-based resin, polyurethane-based resin, polysulfone-based resin, polyphenylene sulfide-based resin and cycloolefin-based resin; and copolymers such as a butadiene-styrene-based copolymer, acrylonitrile-styrene-based copolymer, acrylonitrile-butadiene-styrene-based copolymer, styrene-isoprene-based copolymer, styrene-acrylic acid-based copolymer and vinyl chloride-vinylidene chloride-acrylonitrile-based copolymer. Any one kind of them may be used alone, or two or more kinds thereof may be used in combination.

Although not particularly limited, examples of the polymers of the thermoplastic resin are as follows.

Although not particularly limited, examples of the (meth) acryl-based resin include poly(meth)acrylic acid, methyl poly(meth)acrylate, ethyl poly(meth)acrylate, butyl poly (meth)acrylate and poly(meth)acrylonitrile.

Although not particularly limited, examples of the olefin-based resin include polyethylene, polypropylene, polybutene, polybutadiene, polyisoprene, poly(2,3-dimethylbutadiene), polycyclohexadiene, polycyclopentadiene, polydicyclopentadiene, polychloroprene and polynorbornene.

Although not particularly limited, examples of the styrene-based resin include polystyrene.

Although not particularly limited, examples of the ester-based resin include polyethylene terephthalate, polybutylene terephthalate, polycyclohexanedimethylene terephthalate, polyethylene naphthalate, polybutylene naphthalate, polycaprolactone, polyethylene succinate, polylactic acid, polymalic acid and polyglycolic acid.

Although not particularly limited, examples of the ether-based resin include polyacetal, polyphenylene ether, polyetherketone, polyetheretherketone, polyetherketoneketone, polyetheretherketoneketone, poly ethersulfone and poly etherimide.

Although not particularly limited, examples of the vinyl chloride-based resin include polyvinyl chloride and polyvinylidene chloride.

Although not particularly limited, examples of the fluorocarbon-based resin include polytetrafluoroethylene, polyvinyl fluoride and polyvinylidene fluoride.

Although not particularly limited, examples of the vinyl-based resin include polyvinyl acetate, polyvinyl alcohol, polyvinyl sulfonic acid and salts thereof.

Although not particularly limited, examples of the polycarbonate-based resin include poly carbonate.

Although not particularly limited, examples of the polyamide-based resin include polyamide, nylon 6, nylon 66, nylon 11 and nylon 12.

Although not particularly limited, examples of the polyimide-based resin include polyimide.

Although not particularly limited, examples of the polyamideimide-based resin include polyamideimide.

Although not particularly limited, examples of the polymaleimide-based resin include polymaleimide and poly N-phenylmaleimide.

Although not particularly limited, examples of the polyvinylpyrrolidone-based resin include polyvinylpyrrolidone.

Although not particularly limited, examples of the polyurethane-based resin include polyurethane.

Although not particularly limited, examples of the polysulfone-based resin include polysulfone.

Although not particularly limited, examples of the polyphenylene sulfide-based resin include a polyphenylene sulfide resin.

Although not particularly limited, examples of the cycloolefin-based resin include a cycloolefin polymer.

As a copolymer of the thermoplastic resin, there may be listed those containing a number of raw material monomers of the polymers described above; although not particularly limited, examples of such copolymer are as follows.

Although not particularly limited, examples of the butadiene-styrene-based copolymer include a butadiene-styrene copolymer.

Although not particularly limited, examples of the acrylonitrile-styrene-based copolymer include an acrylonitrile-styrene copolymer.

Although not particularly limited, examples of the acrylonitrile-butadiene-styrene-based copolymer include an acrylonitrile-butadiene-styrene-copolymer.

Although not particularly limited, examples of the styrene-isoprene-based copolymer include a styrene-isoprene copolymer.

Although not particularly limited, examples of the styrene-acrylic acid-based copolymer include a styrene-acrylic acid copolymer.

Although not particularly limited, examples of the vinyl chloride-vinylidene chloride-acrylonitrile-based copolymer include a vinyl chloride-vinylidene chloride-acrylonitrile copolymer.

There are no particular restrictions on the thermosetting resin, examples of which may include polymers such as a phenol-based resin, urea-formaldehyde-based resin, melamine-based resin, unsaturated polyester-based resin, alkyd-based resin, epoxy-based resin and episulfide-based resin; and copolymers such as an acrylic melamine-based resin and acrylic urethane-based resin. Any one kind of them may be used alone, or two or more kinds thereof may be used in combination.

Although not particularly limited, examples of the polymers of the thermosetting resin are as follows.

Although not particularly limited, examples of the phenol-based resin include a phenolic resin.

Although not particularly limited, examples of the urea-formaldehyde-based resin include a urea-formaldehyde resin.

Although not particularly limited, examples of the melamine-based resin include a melamine resin.

Although not particularly limited, examples of the unsaturated polyester-based resin include an unsaturated polyester resin.

Although not particularly limited, examples of the alkyd-based resin include an alkyd resin.

Although not particularly limited, examples of the epoxy-based resin include an epoxy resin.

Although not particularly limited, examples of the episulfide-based resin include an episulfide resin.

Although not particularly limited, examples of the copolymers of the thermosetting resin are as follows.

Although not particularly limited, examples of the acrylic melamine-based resin include an acrylic melamine resin.

Although not particularly limited, examples of the acrylic urethane-based resin include an acrylic urethane resin.

The ultraviolet absorber of the present invention can be favorably used to produce and process an ultraviolet absorber-containing organic and inorganic material(s), because the ultraviolet absorber of the present invention only exhibits a low level of discoloration and weight loss, and is also capable of suppressing odors even after being placed in a heated environment for a long period of time (a given temperature for a given period of time). There are no particular restrictions on the organic resin to be combined with the ultraviolet absorber of the present invention, examples of which may include the aforementioned thermoplastic resins (polymers and copolymers) and thermosetting resins (polymers and copolymers). As the thermoplastic resin, for example, even among the polymers of the thermoplastic resin, there can be preferably used a (meth)acryl-based resin (polymethyl methacrylate), an ester-based resin (polyethylene terephthalate: PET), a polycarbonate-based resin (polycarbonate: PC), a styrene-based resin (polystyrene: PS) and a cycloolefin-based resin (cycloolefin polymer: COP); even among the copolymers of the thermoplastic resin, there can be preferably used an acrylonitrile-butadiene-styrene-based copolymer (acrylonitrile-butadiene-styrene copolymer: ABS); and even among the thermosetting resins, there can be preferably used a urea-formaldehyde-based resin (urea-formaldehyde resin), a melamine-based resin (melamine resin) and an acrylic melamine-based resin (acrylic melamine resin). Even among these examples, a thermoplastic resin(s) can be preferably used. Further, even among the thermosetting resins, a copolymer(s) can be preferably used; for example, an acrylic melamine-based resin (acrylic melamine resin) can be preferably use.

When combined with the ultraviolet absorber of the present invention, there can be obtained an organic resin composition capable of sufficiently and efficiently absorbing lights of a wavelength of 250 to 430 nm. Further, due to the heat resistance of the ultraviolet absorber of the present invention as well as the compatibility and affinity thereof to organic resins, an organic resin composition containing the ultraviolet absorber of the present invention is superior in appearance, and does not discolor so as to be able to maintain a transparency and inhibit yellowing when used under a heated and high-temperature environment at the time of production and processing and/or an ultraviolet exposure environment.

It is preferred that the organic resin(s) be contained in the organic resin composition of the present invention by an amount of not smaller than 0.001% by mas, more preferably not smaller than 0.01% by mass, particularly preferably not smaller than 0.1% by mass, per a total amount of the organic resin composition excluding the ultraviolet absorber of the present invention. The organic resin composition is, for example, that prepared by mixing, dispersing or dissolving the ultraviolet absorber of the present invention together with the organic resin(s), or that prepared by mixing, dispersing or dissolving the ultraviolet absorber of the present invention into the organic resin(s). An inorganic compound(s) used in, for example, a filler, a silane coupling agent and a primer may also be added to the organic resin composition.

Although not particularly limited, examples of the inorganic material include a siliceous material produced by a sol-gel method, a glass, a liquid glass, a low-melting glass, quartz, a silicon resin, alkoxysilane, a silane coupling agent, a metal, a metal oxide, a mineral and an inorganic compound. Although not particularly limited, examples of the glass include silicon oxide, an alkali-free glass and a soda glass. Although not particularly limited, examples of the liquid glass include an aqueous solution of a water-soluble alkali metal salt, such as silicate soda and potassium silicate. Although not particularly limited, examples of the low-melting glass include a glass containing lead oxide (PbO) and boric acid anhydride ($B_2O_3$) as main components. Although not particularly limited, examples of the silicon resin include a methyl silicon resin, a methylphenyl silicon resin; and organic resin-modified silicon resins such as those modified by an epoxy resin, an alky d resin, a poly ester resin or the like. Although not particularly limited, examples of the alkoxysilane include dimethyldimethoxysilane, methylphenyldimethoxysilane, methylvinyldimethoxysilane, 3-mercaptopropylmethyldimethoxysilane, 3,3,3-trifluoropropylmethyldimethoxysilane, methyltrimethoxysilane, vinyltrimethoxysilane and 3-mercaptopropyltrimethoxysilane. Although not particularly limited, examples of the silane coupling agent include 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, 3-methacryloxypropylmethyldimethoxysilane, 3-methacryloxypropyltrimethoxysilane, 3-isocyanatepropyltriethoxysilane N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-aminopropyltriethoxysilane, 3-triethoxysilyl-N-(1,3-dimethyl-butylidene)propylamine, N-phenyl-3-aminopropyltrimethoxysilane, 3-mercaptopropylmethyldimethoxysilane, 3-mercaptopropyltrimethoxysilane, bis(triethoxysilylpropyl)tetrasulfide and 3-isocyanatepropylethoxysilane. Although not particularly limited, examples of the metal include Zn, Fe, Cu, Ni, Ag, Si, Ta, Nb, Ti, Zr, Al, Ge, B, Na, Ga, Ce, V, P and Sb. Although not particularly limited, examples of the metal oxide include zinc oxide, titanium oxide cerium oxide, iron oxide, tin oxide, indium oxide and antimony oxide. Although not particularly limited, examples of the mineral include smectite, bentonite, hectorite and montmorillonite.

Shape of Member

A member may have any shape, and there are no particular restrictions on the shape of a member. For example, there may be listed a coating, an adhesive agent, a pressure sensitive adhesive, a flexible or bendable film, a rigid plate (plate-shaped) member, a powdered member, a granular member, a pellet-shaped member, a tablet (tablet-shaped) member, a masterbatch and a molded product.

[1] Coating

Specific examples of application include coatings applied to the surfaces of members such as a resin and a glass. Although not particularly limited, a coating method may, for example, be such a method where a resin, paint, siliceous material, glass, solvent dispersion liquid or the like with the ultraviolet absorber of the present invention being mixed, dissolved or dispersed therein is to be applied to or sprayed onto the surface of a member, or used to form a film thereon; or where a coating film containing the ultraviolet absorber of the present invention is to be produced

[2] Adhesive Agent

Although not particularly limited, specific examples of application include adhesive agents with the ultraviolet absorber of the present invention being mixed, dissolved or dispersed in organic adhesive agents (e.g. organic resin, synthetic rubber, starch, pressure sensitive adhesive) or inorganic adhesive agents (e.g. silica, ceramics, cement, solder, liquid glass) that are applicable to various materials and members.

[3] Pressure Sensitive Adhesive

Although not particularly limited, specific examples of application include pressure sensitive adhesives with the ultraviolet absorber of the present invention being mixed, dissolved or dispersed in pressure sensitive adhesives (e.g. organic resin, organic oligomer, organic resin monomer, rubber-based gluing agent, starch, pressure sensitive adhesive, silicone-based pressure sensitive adhesive, silane coupling agent-based pressure sensitive adhesive) that are applicable to various materials and members.

[4] Film

Although not particularly limited, specific examples of application include members with the ultraviolet absorber of the present invention being mixed, dissolved or dispersed in flexible or bendable film-shaped resin, glass or silicon oxide precursors. The film may be a single-layered film, a base material film, or a multi-layered film or film-mounted substrate with one layer or multiple layers being mounted on a substrate depending on intended uses; if mounting multiple layers, at least one of the layers contains the ultraviolet absorber of the present invention. The film-shaped resin or glass containing the ultraviolet absorber of the present invention may also be used as an intermediate film for pieces of glass that are laminated together.

[5] Plate

Although not particularly limited, specific examples of application include members with the ultraviolet absorber of the present invention being mixed, dissolved or dispersed in plate (plate-shaped) resins or glasses.

[6] Powder, Grain, Pellet, Tablet (Tabella)

Although not particularly limited, specific examples of application include members with the ultraviolet absorber of the present invention being mixed, dissolved or dispersed in powdered, granular, pellet-shaped or tablet (tablet-shaped) resins or glasses.

[7] Masterbatch

Although not particularly limited, specific examples of application include, for example, granular or pellet-shaped resin compositions with the ultraviolet absorber of the present invention as well as a colorant such as a pigment, if necessary, being mixed, dissolved or dispersed in resins or the like. It is employed by being melted and mixed with other resins, etc.

[8] Molded Product

Although not particularly limited, specific examples of application include molded products with the ultraviolet absorber of the present invention being mixed, dissolved or dispersed in resins or glasses.

Additive

The composition or member containing the ultraviolet absorber of the present invention may further contain various additives to such an extent that the properties of the composition or member will not be impaired: although not particularly limited, examples of such additives include an antioxidant, a heat-resistant stabilizer, a weather-resistant stabilizer, a light stabilizer, a pigment, a dye, a filler, a plasticizer, an antistatic agent, a nucleating agent, a moisturizer, a preservative, an antifungal agent, a defoaming agent, a stabilizer, an antioxidant agent and a chelator.

The ultraviolet absorber of the present invention is used in fields where a high heat resistance is required; there are no restrictions on the type, shape and intended use of the composition and member.

The composition or member containing the ultraviolet absorber of the present invention may be an ultraviolet absorber-containing composition superior in heat resistance; for example, in cases of a coating film, a film or the like that contain the ultraviolet absorber of the present invention and are for use in a transparent resin or transparent glass, the coating film and film can be such a coating film and film that do not exhibit yellowing, discoloration, a deterioration in ultraviolet absorption capability and a deterioration in transparency for a long period of time from their production until their actual use.

There are no particular limitations on the intended use of the ultraviolet absorber of the present invention; the ultraviolet absorber of the present invention can be preferably used, in particular, for purposes where there exists a possibility of being exposed to lights of a wavelength of 380 to 400 nm, or even 380 to 430 nm, the sunlight, lights including ultraviolet lights, or LED emissions.

Although not particularly limited, the ultraviolet absorber of the present invention may also be used in, for example, members or articles for use in houses, facilities, transportation equipments, displays or the like; interior/exterior materials and paints for houses, facilities, transportation equipments or the like as well as coating films formed by those paints, and even adhesive agents and pressure sensitive adhesives associated therewith; films or members for shielding, for example, electromagnetic waves generated from precision machines, electrical and electronic equipments or various displays; containers or packaging materials for foods, chemical goods, chemicals and cosmetics or the like; sheets or film materials for agricultural and industrial uses; discoloration inhibitors for printed materials, dyes/pigments or the like; protective films for resin members or various devices; glass interlayers; cosmetics; clothing textile products or textiles; interior articles for household use such as curtains, carpets and wallpapers; plastic lenses; medical instruments such as contact lenses and artificial eyes; optical lenses such as optical pickup lenses, camera lenses and lenticular lenses; optical articles such as optical filters, backlight display films, prisms, mirrors, photograph materials and displays as well as protective films for these optical articles: optical materials; films having a functional optical layer(s) (although not particularly limited, examples of which may include protective films for various optical disk substrates, reflective films, anti-reflective films, alignment films, polarizing films, polarizing layer protective films, retardation films, light diffusion films, viewing angle improving films, electromagnetic wave shield films, anti-glare films, light shielding films and brightness improving films) as well as members, adhesive agents or pressure sensitive adhesives associated therewith; optical molded products such as optical fibers and information recording substrates; surface protection films for solar cells; stationery products; sign boards, indicators or the like as well as surface coating materials thereof; glass substitutes and surface coating materials thereof; glasses and glass coating materials for houses, facilities, transportation equipments or the like; daylight glasses; members for those such as fluorescent lamps, mercury lamps, halogen bulbs, LED lights or the like; coating materials for members for light source and light source protective glasses; and window glasses, window films and intermediate films for laminated glasses for houses, facilities, transportation equipments or the like.

Further, other than the use as an organic resin composition, in terms of an organic material composition, although not particularly limited, the ultraviolet absorber of the present invention may be used in, for example, discoloration inhibitors for cosmetics, printed materials, dyed materials, dyes/pigments or the like.

WORKING EXAMPLES

Although the present invention is described in greater detail hereunder with reference to working examples, the present invention shall not be limited to these working examples.

(1) Synthesis of Ultraviolet Absorber
<Synthesis of Intermediate Compound>

Intermediates 1 to 5 represented by the following formulae were synthesized.

<Intermediate 1>

[Chemical formula 4]

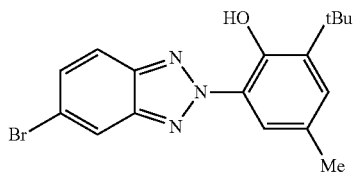

Here, 4-bromo-2-nitroaniline (10.0 g, 46.1 mmol), water (35 mL), sodium bis(2-ethylhexyl) sulfosuccinate (0.0041 g, 0.092 mmol) and a 62.5% sulfuric acid aqueous solution (25 mL) were added, and then heated and dissolved, followed by spending 30 min delivering thereinto by drops a 36% sodium nitrite aqueous solution (10 mL) under an ice-cooled condition, and then allowing them to react for 30 min so as to obtain a diazonium salt. Next, under an ice-cooled condition, an hour was spent delivering such diazonium salt aqueous solution by drops into an aqueous solution (100 mL) prepared by mixing 2-tert-butyl-p-cresol (7.95 g, 48.4 mmol) and sodium hydroxide (12.38 g, 309.6 mmol), followed by allowing them to react for an hour at the temperature as it was. After the reaction was over, hydrochloric acid was used to turn the reactant acidic, followed by filtrating a precipitate, and then washing a residue with isopropyl alcohol, thereby obtaining an intermediate 2 shown below.

<Intermediate 2>

[Chemical formula 5]

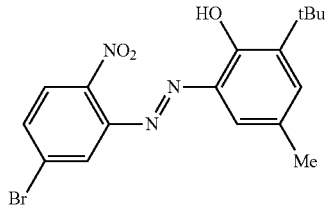

While being heated and refluxed, the intermediate 2 (3.50 g 8.92 mmol), a 2MNaOH aqueous solution (14 mL) and a zinc powder (5.60 g 85.66 mmol) were reacted in toluene (30 mL) for three hours. After being cooled to room temperature, water washing, solvent removal and column purification were performed to obtain an intermediate 1.

<Intermediate 3>

[Chemical formula 6]

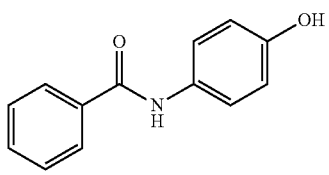

In an ice bath, 15 mL of a DMF solution containing benzoyl chloride (7.05 g, 50 mmol) was delivered by drops into 20 mL of a DMF solution containing 4-aminophenol (5.45 g, 50 mmol). After completing delivering the solution by drops, stirring was performed at room temperature for two and a half hours. After the reaction was over, the solution whose pH level had now been adjusted to 7 was then delivered by drops into 500 mL of an ion-exchange water, followed by collecting a solid precipitated so as to obtain a white solid as an intermediate 3.

<Intermediate 4>

[Chemical formula 7]

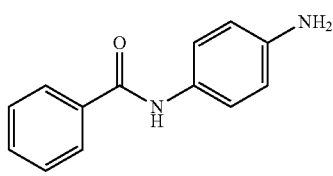

In an ice bath, benzoyl chloride (21.4 mL, 185 mmol) was delivered by drops into 500 mL of a dichloromethane solution containing 1,4-phenylenediamine (20.1 g, 185 mmol) and triethylamine (30 mL, 284 mmol). After completing delivering the solution by drops, stirring was performed at room temperature for three and a half hours. After the reaction was over, filtration was performed, water was then added to a filtrate, a solid precipitated was then collected, water washing was then carried out, and recrystallization was then performed to obtain a white solid as an intermediate 4.

<Intermediate 5>

[Chemical formula 8]

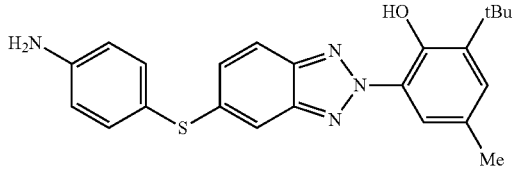

Here, 2-(2-hydroxy-3-tert-butyl-5-methylphenyl)-5-chlorobenzotriazole (5.00 g, 15.8 mmol), 4-aminobenzenethiol (2.97 g, 23.8 mmol), potassium carbonate (4.81 g, 34.8 mmol) and potassium iodide (0.18 g, 1.11 mmol) were reacted in 30 g of DMF at 135° C. for three hours. After the reaction was over. pH was adjusted, followed by performing filtration, water washing, MeOH washing and then recrystallization to obtain a light yellow solid as an intermediate 5.

<Synthesis of Ligand Compound>

A ligand represented by the following formula was synthesized.

<Ligand>

[Chemical formula 9]

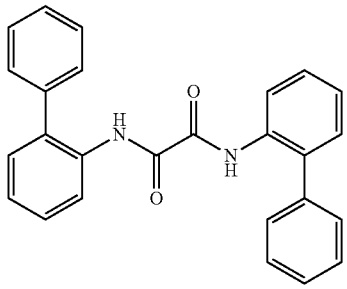

Here, 2-aminobiphenyl (13.57 g, 80 mmol) and triethylamine (9.1 g, 90 mmol) were dissolved into 300 mL of THF followed by slowly delivering oxalyl chloride (5.08 g, 40 mmol) by drops thereinto while performing stirring on ice. After completing delivering the oxalyl chloride by drops, stirring was performed at room temperature for two hours. After the reaction was over, the solvent was distilled away, a solid obtained was then suspended in water, followed by performing filtration to obtain a yellow solid. The solid was then washed with water and a cooled diethyl ether to obtain a white solid as a ligand.

Synthesis Example 1

Synthesis of Compound 1

[Chemical formula 10]

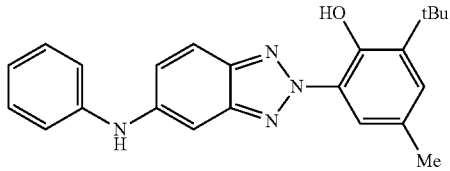 [SMILES: Cc1cc(-n2nc3ccc(Nc4ccccc4)cc3n2)c(O)c(C(C)(C)C)c1]

Here, 2-(3-tert-butyl-2-hydroxy-5-methylphenyl)-5-chlorobenzotriazole (3.17 g, 10 mmol), tris(dibenzylideneacetone)dipalladium (0) (45.8 mg, 0.05 mmol), Xphos (2-Dicyclohexylphosphino-2',4',6'-triisopropylbiphenyl) (95.1 mg, 0.2 mmol), potassium hydroxide (786 mg, 14 mmol), aniline (1.09 mL, 12 mmol) and an ion-exchange water (5 mL) were stirred at 100° C. for five hours under Ar. After the reaction was over, ethyl acetate and hydrochloric acid were added, a solid component was removed by suction filtration, and the solvent was distilled away from a filtrate. A crude product obtained by adding MeOH to an oil-like product obtained was purified via column chromatography and recrystallization, thereby obtaining a yellow solid as the target product.

FT-IR: 2975 cm$^{-1}$: O—H stretching vibration 1412 cm$^{-1}$, 1370 cm$^{-1}$: triazole ring stretching vibration $^1$H-NMR (CDCl$_3$:400 MHz): δ1.49 (s, 9H, —C—(CH$_3$)$_3$), 2.38 (s, 3H, —CH$_3$), 5.98 (s, 1H, NH), 7.05 (t, 1H), 7.14 (s, 1H), 7.17 (d, 1H), 7.21 (d, 2H), 7.35 (t, 2H), 7.41 (s, 1H), 7.80 (t, 1H), 8.02 (s, 1H), 11.72 (s, 1H, —OH)

$^{13}$C-NMR (CDCl$_3$:400 MHz): δ20.9 (—CH$_3$), 29.5 (—C—(CH$_3$)$_3$), 35.4 (—C—(CH$_3$)$_3$), 97.9, 118.5, 119.0, 119.5, 1225, 123.2, 128.1, 129.6 (CH$_{arom}$), 125.6, 139.0, 141.9, 143.2, 144.1 (C$_{arom}$), 128.1 (C$_{arom}$—CH$_3$), 139.1 (—C$_{arom}$—C—(CH$_3$)$_3$), 146.4 (—C$_{arom}$—OH)

Synthesis Example 2

Synthesis of Compound 2

[Chemical formula 11]

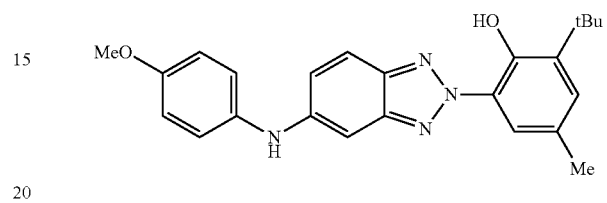

After stirring palladium acetate (22.2 ng, 0.1 mmol) Xphos (95.2 mg, 0.2 mmol), an ion-exchange water (10 μL) and 20 mL, of tert-butyl alcohol under Ar at 110° C. for 2 min, there were added 2-(3-tert-butyl-2-hydroxy-5-methylphenyl)-5-chlorobenzotriazole (3.14 g, 10 mmol), potassium carbonate (1.93 g, 14 mmol) and p-anisidine (1.35 g, 11 mmol) to then perform stirring tinder a heated condition for two hours. After the reaction was over, toluene and hydrochloric acid were added, water washing was performed, followed by removing a solid component via suction filtration, and then distilling away the solvent from a filtrate. A crude product obtained was purified via recrystallization so as to obtain a yellow solid as the target product.

FT-JR: 2961 cm$^{-1}$: O—H stretching vibration 1448 cm$^{-1}$, 1310 cm$^{-1}$: triazole ring stretching vibration 1034 cm$^{-1}$: C—O—C symmetric stretch $^1$H-NMR (CDCl$_3$:400 MHz): δ1.48 (s, 9H, —C—(CH$_3$)$_3$), 2.37 (s, 3H, —CH$_3$), 3.84 (s, 3H, —CH$_3$), 5.76 (s, 1H, —NH—) 6.93 (d, 2H), 7.07 (d, 1H), 7.12 (s, 1H), 7.13 (s, 1H), 7.19 (d, 2H), 7.76 (d, 1H), 7.99 (s, 1H), 11.72 (s, 1H, —OH)

$^{13}$C-NMR (CDCl$_3$:400 MHz): δ20.9 (—CH$_3$), 29.6 (—C—(CH$_3$)) 35.4 (—C—(CH$_3$)$_3$), 55.6 (—O—CH$_3$), 95.3, 114.9, 118.4, 119.0, 122.4, 1238, 128.0 (CH$_{arom}$), 125.6, 134.4, 138.7, 144.3, 145.3, 146.4, 156.3 (C$_{arom}$), 128.1 (C$_{arom}$—CH$_3$), 138.9 (—C$_{arom}$—C—(CH$_3$)$_3$)

Synthesis Example 3

Synthesis of Compound 3

[Chemical formula 12]

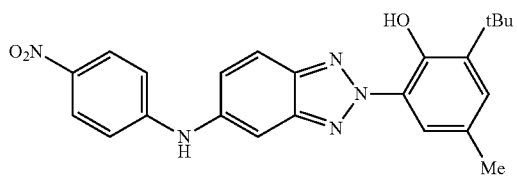 [SMILES: Cc1cc(-n2nc3ccc(Nc4ccc([N+](=O)[O-])cc4)cc3n2)c(O)c(C(C)(C)C)c1]

After stirring palladium acetate (22.0 mg, 0.1 mmol), Xphos (95.2 mg, 0.2 mmol), an ion-exchange water (10 μL) and 20 mL of tert-butyl alcohol under Ar at 110° C. for 2 min, there were added 2-(3-tert-butyl-2-hydroxy-5-methylphenyl)-5-chlorobenzotriazole (3.16 g, 10 mmol), potassium carbonate (1.93 g, 14 mmol) and 4-nitroaniline (1.52 g, 11 mmol) to then perform stirring under a heated condition for two hours. After the reaction was over, toluene and hydrochloric acid were added, water washing was performed, followed by removing a solid component via suction filtration, and then distilling away the solvent from a filtrate. A crude product obtained was purified via recrystallization so as to obtain a yellow solid as the target product.

FT-IR: 2977 cm$^{-1}$: O—H stretching vibration 1569 cm$^{-1}$, 1373 cm$^{-1}$: N—O stretching vibration 1441 cm$^{-1}$, 1322 cm$^{-1}$: triazole ring stretching vibration $^1$H-NMR (CDCl$_3$:400 MHz): δ1.50 (s, 9H, —C—(C$\underline{H}_3$)$_3$), 2.39 (s, 3H, —C$\underline{H}_3$), 6.46 (s, 1H, —N$\underline{H}$—), 7.10 (d, 2H), 7.19 (s, 1H), 7.31 (d, 1H), 7.69 (s, 1H), 7.64 (d, 1H), 8.06 (d, 1H), 8.20 (d, 2H), 11.67 (s, 1H, —O$\underline{H}$)

$^{13}$C-NMR (CDCl$_3$:400 MHz): δ20.9 (—$\underline{C}$H$_3$) 29.6 (—C—($\underline{C}$H$_3$)$_3$), 35.4 (—$\underline{C}$—(CH$_3$)$_3$) 105.6, 114.9, 119.2, 124.3, 126.2, 128.8 ($\underline{C}$H$_{arom}$), 119.3, 140.3, 146.7, 149.0 ($\underline{C}_{arom}$), 128.4 ($\underline{C}_{arom}$—CH$_3$), 139.2 (—$\underline{C}_{arom}$—C—(CH$_3$)$_3$)

Synthesis Example 4

Synthesis of Compound 4

[Chemical formula 13]

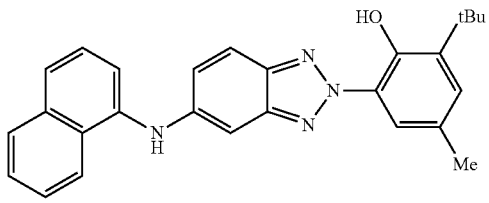 [SMILES: Cc1cc(-n2nc3ccc(Nc4cccc5ccccc45)cc3n2)c(O)c(C(C)(C)C)c1]

After stirring 2-(3-tert-butyl-2-hydroxy-5-methylphenyl)-5-chlorobenzotriazole (3.16 g, 10 mmol), tris(dibenzylideneacetone)dipalladium (0) (45.6 mg, 0.05 mmol), Xphos (95.2 mg, 0.2 mmol), potassium hydroxide (785 mg, 14 mmol), 1-naphthylamine (1.58 g, 11 mmol) and an ion-exchange water (5 mL) under Ar at 100° C. for 30 min, 3 mL of toluene was added to then perform stirring under a heated condition for five hours. After the reaction was over, toluene and hydrochloric acid were added, water washing was performed, followed by removing a solid component via suction filtration, and then distilling away the solvent from a filtrate. A crude product obtained was purified via column chromatography to obtain a yellow solid as the target product.

FT-IR: 2953 cm$^{-1}$: O—H stretching vibration 1437 cm$^{-1}$, 1396 cm$^{-1}$: triazole ring stretching vibration $^1$H-NMR (CDCl$_3$:400 MHz): δ1.47 (s, 9H, —C—(C$\underline{H}_3$)$_3$) 2.36 (s, 3H, —C$\underline{H}_3$), 6.16 (s, 1H, —N$\underline{H}$—), 7.05 (s, 1H), 7.12 (s, 1H), 7.24 (d, 1H), 7.47 to 7.55 (m, 4H), 7.79 (t, 1H), 7.81 (d, 1H), 7.91 (d, 1H), 7.99 (s, 1H), 8.05 (d, 1H), 11.67 (s, 1H, —O$\underline{H}$)

$^{13}$C-NMR (CDCl$_3$:400 MHz): δ20.9 (—$\underline{C}$H$_3$), 29.5 (—C—($\underline{C}$H$_3$)$_3$), 35.3 (—$\underline{C}$—(CH$_3$)$_3$), 97.7, 118.4, 119.0, 122.1, 122.7, 124.8, 126.0, 126.2, 126.4, 128.0, 128.6 ($\underline{C}$H$_{arom}$), 125.6, 134.8, 137.6, 144.1, 145.2, 146.4 ($\underline{C}_{arom}$), 128.6 ($\underline{C}_{arom}$—CH$_3$), 138.9 (—$\underline{C}_{arom}$—C—(CH$_3$)$_3$)

Synthesis Example 5

Synthesis of Compound 5

[Chemical formula 14]

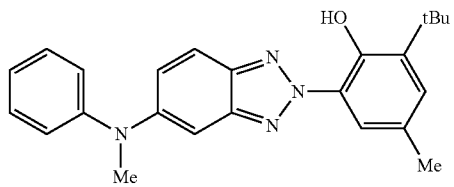 [SMILES: Cc1cc(-n2nc3ccc(N(C)c4ccccc4)cc3n2)c(O)c(C(C)(C)C)c1]

Here 2-(3-tert-butyl-2-hydroxy-5-methylphenyl)-5-chlorobenzotriazole (9.48 g, 30 mmol), tris(dibenzylideneacetone)dipalladium (0) (140 mg, 0.15 mmol), Xphos (283 mg, 0.6 mmol), potassium hydroxide (2.34 g, 42 mmol), N-methylaniline (5.00 mL, 47 mmol) and an ion-exchange water (15 mL) were stirred under Ar and a heated condition at 100° C. for two and a half hours. After the reaction was over, ethyl acetate and hydrochloric acid were added, a solid component was removed by suction filtration, and the solvent was then distilled away from a filtrate. A crude product obtained was purified via column chromatography and recrystallization to obtain a yellow solid as the target product.

FT-IR: 2975 cm$^{-1}$: O—H stretching vibration 1412 cm$^{-1}$, 1359 cm$^{-1}$: triazole ring stretching vibration $^1$H-NMR (CDCl$_3$:400 MHz): δ149 (s, 9H, —C—(C$\underline{H}_3$)$_3$), 2.38 (s, 3H, —C—C$\underline{H}_3$) 3.42 (s, 3H, —N—C$\underline{H}_3$), 7.13 to 7.19 (m, 6H), 7.36 (t, 2H), 7.65 (d, 1H), 8.02 (s, 1H), 11.74 (s, 1H, —O$\underline{H}$)

$^{13}$C-NMR (CDCl$_3$:400 MHz): δ20.9 (—$\underline{C}$H$_3$), 29.6 (—C—($\underline{C}$H$_3$)$_3$), 35.4 (—$\underline{C}$—(CH$_3$)$_3$), 41.1 (—N—$\underline{C}$H$_3$), 99.3, 117.3, 124.0, 128.0 ($\underline{C}$H$_{arom}$), 125.6, 1387, 144.3, 148.6, 148.7 ($\underline{C}_{arom}$), 128.1 ($\underline{C}_{arom}$—CH$_3$), 138.9 (—$\underline{C}_{arom}$—C—(CH$_3$)$_3$), 146.4 (—$\underline{C}_{arom}$—OH)

Synthesis Example 6

Synthesis of Compound 6

[Chemical formula 15]

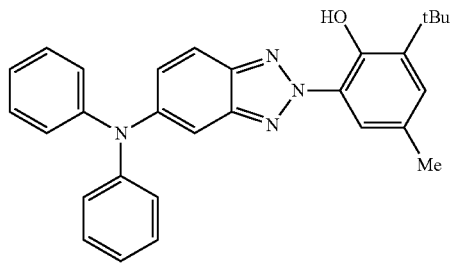 [SMILES: Cc1cc(-n2nc3ccc(N(c4ccccc4)c4ccccc4)cc3n2)c(O)c(C(C)(C)C)c1]

Here 2-(3-tert-butyl-2-hydroxy-5-methylphenyl)-5-chlorobenzotriazole (9.87 g, 31 mmol), tris(dibenzylideneacetone)dipalladium (0) (137 mg, 0.15 mmol), Xphos (287 mg, 0.6 mmol), potassium hydroxide (2.39 g, 43 mmol), diphenylamine (8.32 g, 49 mmol) and an ion-exchange water (15 mL) were stirred under Ar and a heated condition at 100° C. for 24 hours. After the reaction was over, ethyl acetate and hydrochloric acid were added, a solid component was removed by suction filtration, and the solvent was then distilled away from a filtrate. A crude product obtained was purified via column chromatography and recrystallization to obtain a yellow solid as the target product.

FT-IR: 2975 cm$^{-1}$: O—H stretching vibration 1412 cm$^{-1}$, 1370 cm$^{-1}$: triazole ring stretching vibration $^1$H-NMR (CDCl$_3$:400 MHz): δ1.48 (s, 9H, —C—(C$\underline{H}_3$)$_3$), 2.37 (s, 3H, —C$\underline{H}_3$) 7.10 (t, 21H), 713 to 7.16 (m, 5H), 7.28 to 7.34 (m, 6H), 7.75 (d, 1H), 8.00 (s, 1H), 11.63 (s, 1H, —O$\underline{H}$)

$^{13}$C-NMR (CDCl$_3$:400 MHz): δ20 9 (—$\underline{C}$H$_3$), 29.5 (—C—($\underline{C}$H$_3$)$_3$), 35.4 (—$\underline{C}$—(CH$_3$)$_3$), 107.3, 117.8, 119.1, 123.8, 125.0, 126.7, 128.3, 129.5 ($\underline{C}$H$_{arom}$), 125.3, 125.5, 128.1, 129.0, 139.7, 143.8, 147.4, 147.8 ($\underline{C}_{arom}$), 128.2 ($\underline{C}_{arom}$—CH$_3$), 139.0 (—$\underline{C}_{arom}$—C—(CH$_3$)$_3$), 146.5 (—$\underline{C}_{arom}$—OH)

Synthesis Example 7

Synthesis of Compound 7

122.1, 122.8, 128.1 ($\underline{C}$H$_{arom}$), 146.4 ($\underline{C}_{arom}$), 125.6 ($\underline{C}_{arom}$—CH$_3$), 139.0 (—$\underline{C}_{arom}$—C—(CH$_3$)$_3$)

Synthesis Example 8

Synthesis of Compound 8

[Chemical formula 17]

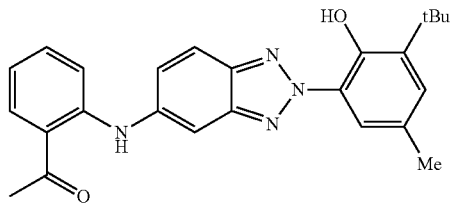 [SMILES: CC(=O)c1ccccc1Nc1ccc2nn(-c3cc(C)cc(C(C)(C)C)c3O)nc2c1]

After stirring 2-(3-tert-butyl-2-hydroxy-5-methylphenyl)-5-chlorobenzotriazole (3.16 g, 10 mmol), tris(dibenzylideneacetone)dipalladium (0) (45.8 mg, 0.05 mmol), Xphos (95.3 mg, 0.2 mmol), potassium hydroxide (786 mg, 14 mmol), 2'-aminoacetophenone (1.8 mL, 12 mmol) and an ion-exchange water (5 mL) under Ar at 100° C. for 30 min, 3 mL of toluene was added to then perform stirring under a heated condition for four hours. After the reaction was over, toluene and hydrochloric acid were added, water washing

[Chemical formula 16]

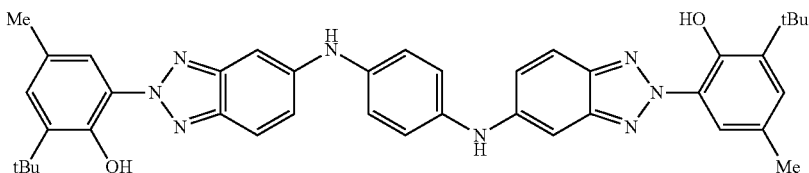

After stirring palladium acetate (44.0 mg, 0.2 mmol), Xphos (192.2 mg, 0.4 mmol), an ion-exchange water (10 μL) and 20 mL of tert-butyl alcohol under Ar at 110° C. for 2 min, there were added 2-(3-tert-butyl-2-hydroxy-5-methylphenyl)-5-chlorobenzotriazole (3.16 g, 10 mmol), potassium carbonate (3.86 g, 28 mmol) and 1,4-phenylenediamine (540.7 mg, 5 mmol) to then perform stirring under a heated condition for 24 hours. After the reaction was over, toluene and hydrochloric acid were added, water washing was performed, followed by removing a solid component via suction filtration, and then distilling away the solvent from a filtrate. A crude product obtained was purified by recrystallization to obtain a yellow solid as the target product.

FT-IR: 2978 cm$^{-1}$: O—H stretching vibration 1449 cm$^{-1}$, 1375 cm$^{-1}$: triazole ring stretching vibration $^1$H-NMR (CDCl$_3$:400 MHz): δ1.49 (s, 18H, —C—(C$\underline{H}_3$)$_3$), 2.38 (s, 6H, —C$\underline{H}_3$), 5.90 (s, 2H, —N$\underline{H}$—), 7.13 to 7.17 (m, 4H), 7.24 (s, 4H), 7.32 (s, 2H), 7.81 (d, 2H), 8.02 (s, 2H), 11.71 (s, 2H, —O$\underline{H}$)

$^{13}$C-NMR (CDCl$_3$:400 MHz) δ20.9 (—$\underline{C}$H$_3$), 29.5 (—$\underline{C}$—(CH$_3$)$_3$), 35.4 (—C—($\underline{C}$H$_3$)$_3$), 96.7, 118.5, 119.0, was performed, followed by removing a solid component via suction filtration, and then distilling away the solvent from a filtrate. A crude product obtained was purified by recrystallization to obtain a yellow solid as the target product.

FT-IR: 2949 cm$^{-1}$: O—H stretching vibration 1632 cm$^{-1}$: C=O stretching vibration 1455 cm$^{-1}$, 1390 cm$^{-1}$: triazole ring stretching vibration $^1$H-NMR (CDCl$_3$:400 MHz): δ1.50 (s, 9H, —C—(C$\underline{H}_3$)$_3$), 2.39 (s, 3H, —C$\underline{H}_3$), 2.68 (s, 3H, —C$\underline{H}_3$), 6.85 (t, 1H), 7.16 (s, 1H), 7.35 (d, 11H), 7.40 (t, 1H), 7.46 (d, 1H), 7.73 (s, 1H), 7.86 to 7.90 (m, 21H), 8.05 (s, 1H), 10.77 (s 1H, —NH—), 11.65 (s, 1H, —O$\underline{H}$)

$^{13}$C-NMR (CDCl$_3$:400 MHz): δ20.9 (—$\underline{C}$H$_3$), 28.2 (—$\underline{C}$H$_3$), 29.5 (—C—($\underline{C}$H$_3$)$_3$), 35.4 (—$\underline{C}$—(CH$_3$)$_3$), 105.7, 115.0, 117.9, 118.5, 119.2, 126.1, 128.2, 128.5, 132.6, 134.7 ($\underline{C}$H$_{arom}$), 120.1, 125.5, 140.1, 140.2, 143.6, 146.6, 146.7 ($\underline{C}_{arom}$), 128.2 ($\underline{C}_{arom}$—CH$_3$) 139.1 (—$\underline{C}_{arom}$—C—(CH$_3$)$_3$), 201.6 (—($\underline{C}$=O)—)

Synthesis Example 9

Synthesis of Compound 9

[Chemical formula 18]

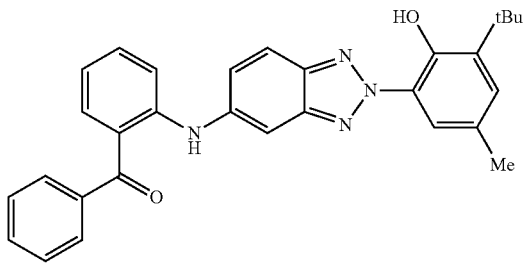 [SMILES: Cc1cc(-n2nc3ccc(Nc4ccccc4C(=O)c4ccccc4)cc3n2)c(O)c(C(C)(C)C)c1]

After stirring 2-(3-tert-butyl-2-hydroxy-5-methylphenyl)-5-chlorobenzotriazole (3.16 g, 10 mmol), tris(dibenzylideneacetone)dipalladium (0) (46.0 mg, 0.05 mmol), Xphos (95.2 mg, 0.2 mmol), potassium hydroxide (787 mg, 14 mmol), 2-aminobenzophenone (2.38 g, 12 mmol) and an ion-exchange water (5 mL) under Ar at 100° C. for 30 min, 3 mL of toluene was added to then perform stirring under a heated condition for four hours. After the reaction was over, toluene and hydrochloric acid were added, water washing was performed, followed by removing a solid component via suction filtration, and then distilling away the solvent from a filtrate. A crude product obtained was purified by recrystallization to obtain a yellow solid as the target product.

FT-IR: 2969 cm$^{-1}$: O—H stretching vibration 1743 cm$^{-1}$: C=O stretching vibration 1451 cm$^{-1}$, 1359 cm$^{-1}$: triazole ring stretching vibration $^1$H-NMR (CDCl$_3$:400 MHz): δ1.50 (s, 9H, —C—(CH$_3$)$_3$), 2.39 (s, 3H, —CH$_3$), 6.85 (t, 1H), 7.16 (s, 1H), 7.38 (d, 1H), 7.39 (t, 1H), 7.50 (t, 2H) 7.56 to 7.61 (m, 3H), 7.74 to 7.76 (m, 3H), 7.88 (d, 2H), 8.06 (s, 1H), 10.24 (s, 1H, —NH—), 11.66 (s, 1H, —OH)

$^{13}$C-NMR (CDCl$_3$:400 MHz): δ20.9 (—CH$_3$), 29.6 (—C—(CH$_3$)$_3$), 35.4 (—C—(CH$_3$)$_3$), 104.0, 115.9, 118.1, 118.6, 119.2, 125.4, 128.2, 128.4, 129.6, 131.8, 134.2, 134.9 (CH$_{arom}$), 121.3, 125.6, 139.4, 139.9, 140.6, 143.7, 146.5, 146.6 (C$_{arom}$), 128.2 (C$_{arom}$—CH$_3$) 139.1 (—C$_{arom}$—C—(CH$_3$)$_3$), 199.2 (—(C=O)—)

Synthesis Example 10

Synthesis of Compound 10

[Chemical formula 19]

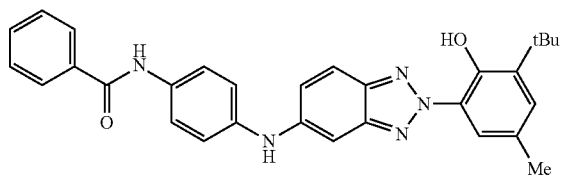 [SMILES: Cc1cc(-n2nc3ccc(Nc4ccc(NC(=O)c5ccccc5)cc4)cc3n2)c(O)c(C(C)(C)C)c1]

The intermediate 4 (317 mg, 1.49 mmol), the intermediate 1 (369 mg, 1.17 mmol) tris(dibenzylideneacetone)dipalladium (0) (92.8 mg, 01.1 mmol) and xantphos (120 mg, 0.21 mmol) and cesium carbonate (658 mg, 2.02 mmol) were dissolved in 5 mL of DMF, and stirred under Ar at 150° C. for 20 hours. After the reaction was over, a solid component was removed via filtration, and the solvent was then distilled away from a filtrate. After separating an oil-like product, purification was performed via column chromatography and recrystallization to obtain a yellow solid as the target product.

FT-IR: 2974 cm$^{-1}$: O—H stretching vibration 1639 cm$^{-1}$: C=O stretching vibration 1412 cm$^{-1}$, 1370 cm$^{-1}$: triazole ring stretching vibration $^1$H-NMR (CDCl$_3$:400 MHz): δ1.49 (s, 9H, —C—(CH$_3$)$_3$), 2.38 (s, 3H, —CH$_3$), 7.14 to 7.17 (m, 2H), 7.27 (d, 2H), 7.37 (d, 1H), 7.52 (t, 2H), 7.58 (t, 1H), 7.64 (d, 2H), 7.79 to 7.82 (m, 2H), 7.90 (d, 2H), 8.02 (s, 1H), 11.71 (s, 1H, —OH)

$^{13}$C-NMR (CDCl$_3$:400 MHz): δ20.9 (—CH$_3$), 29.6 (—C—(CH$_3$)$_3$), 35.4 (—C—(CH$_3$)$_3$) 97.4, 118.5, 119.0, 120.6, 121.8, 122.9, 127.0, 128.1, 128.8, 131.9 (CH$_{arom}$), 125.6, 132.9, 135.0, 138.5, 139.0, 143.5, 144.1 (C$_{arom}$) 139.0 (—C$_{arom}$—C—(CH$_3$)$_3$), 146.4 (—C$_{arom}$—OH), 165.6 (—CONH—)

Synthesis Example 11

Synthesis of Compound 11

[Chemical formula 20]

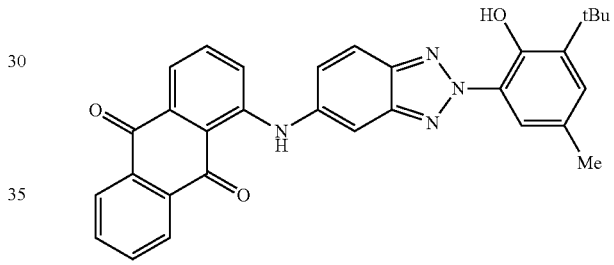

After stirring 2-(3-tert-butyl-2-hydroxy-5-methylphenyl)-5-chlorobenzotriazole (3.16 g, 10 mmol), tris(dibenzylideneacetone)dipalladium (0) (46.0 mg, 0.05 mmol), Xphos (95.1 mg, 0.2 mmol), potassium hydroxide (787 mg, 14 mmol), 2-aminobenzophenone (3.00 g, 13 mmol) and an ion-exchange water (5 mL) under Ar at 100° C. for 30 min, 3 mL of toluene was added to then perform stirring under a heated condition for four hours. After the reaction was over, toluene and hydrochloric acid were added, water washing was performed, followed by removing a solid component via suction filtration, and then distilling away the solvent from a filtrate. A crude product obtained was purified via column chromatography and recrystallization to obtain a red solid as the target product.

FT-IR: 2970 cm$^{-1}$: O—H stretching vibration 1742 cm$^{-1}$: C=O stretching vibration 1437 cm$^{-1}$, 1359 cm$^{-1}$: triazole ring stretching vibration $^1$H-NMR (CDCl$_3$:400 MHz): δ1.51 (s, 9H, —C—(CH$_3$)$_3$), 2.40 (s, 3H, —CH$_3$), 7.19 (s, 1H), 7.44 (d, 1H) 7.61 (t, 1H), 7.74 (d, 1H) 7.76 to 7.84 (m, 4H), 7.96 (d, 2H), 8.08 (d, 2H), 8.31 (d, 1H), 8.35 (d, 1H), 11.59 (s, 1H, —NH—), 11.61 (s, 1H, —OH)

$^{13}$C-NMR (CDCl$_3$:400 MHz): δ20.9 (—CH$_3$) 29.5 (—C—(CH$_3$)$_3$), 35.4 (—C—(CH$_3$)$_3$), 108.4, 118.7, 118.9, 119.3, 120.3, 1263, 127.0, 128.8, 1336, 134.2, 135.2 (CH$_{arom}$), 133.1, 134.7, 134.9, 139.2, 140.6, 143.5, 146.7, 148.3 (C$_{arom}$), 128.3 (C$_{arom}$—CH$_3$) 139.1 (—C$_{arom}$—C—(CH$_3$)$_3$), 185.9 (—(C=O)—)

Synthesis Example 12

Synthesis of Compound 12

[Chemical formula 21]

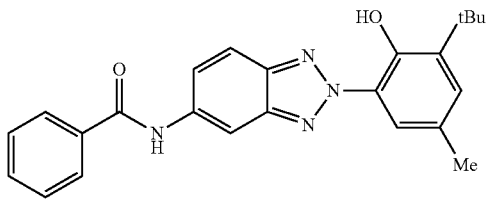 [SMILES: Cc1cc(-n2nc3ccc(NC(=O)c4ccccc4)cc3n2)c(O)c(C(C)(C)C)c1]

After stirring palladium acetate (22.0 mg, 0.1 mmol), Xphos (95.2 mg, 0.2 mmol), an ion-exchange water (10 μL) and 20 mL of tert-butyl alcohol under Ar at 110° C. for 2 min, there were added 2-(3-tert-butyl-2-hydroxy-5-methylphenyl)-5-chlorobenzotriazole (3.16 g, 10 mmol), potassium carbonate (1.93 g, 14 mmol) and benzamide (1.33 g, 11 mmol) to then perform stirring under a heated condition for 24 hours. After the reaction was over, water was added to collect a solid via suction filtration, followed by dissolving the solid into toluene, and then again collecting the solid. A crude product obtained was purified by recrystallization to obtain a white solid as the target product.

FT-IR: 2957 cm$^{-1}$: O—H stretching vibration 1649 cm$^{-1}$: C=O stretching vibration 1440 cm$^{-1}$, 1360 cm$^{-1}$: triazole ring stretching vibration $^1$H-NMR (CDCl$_3$:400 MHz): δ1.50 (s, 9H, —C—(C$\underline{H}_3$)$_3$), 2.39 (s, 3H, —C$\underline{H}_3$) 7.18 (s, 11H), 7.51 to 7.56 (m, 3H), 7.59 (t, 1H), 7.91 to 7.94 (m, 3H), 7.98 (s, 1H), 8.08 (s, 1H), 8.50 (a, 1H), 11.65 (s, 1H, —N$\underline{H}$—)

$^{13}$C-NMR (CDCl$_3$:400 MHz): δ20.9 (—$\underline{C}$H$_3$), 29.6 (—C—($\underline{C}$H$_3$)$_3$), 35.4 (—$\underline{C}$—(CH$_3$)$_3$) 106.4, 118.3, 119.4, 123.0, 127.1, 128.7, 130.0, 132.2 ($\underline{C}$H$_{arom}$), 125.5, 134.7, 137.0, 140.3, 143.2 ($\underline{C}_{arom}$), 128.3 ($\underline{C}_{arom}$—CH$_3$), 139.2 (—$\underline{C}_{arom}$—C—(CH$_3$)$_3$), 146.7 (—$\underline{C}_{arom}$—OH), 165.9 (—$\underline{C}$ONH—)

Synthesis Example 13

Synthesis of Compound 13

[Chemical formula 22]

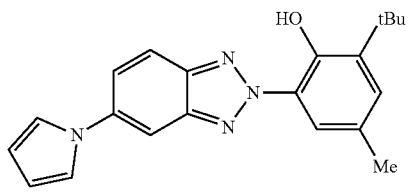 [SMILES: Cc1cc(-n2nc3ccc(-n4cccc4)cc3n2)c(O)c(C(C)(C)C)c1]

Here, 2'-(3-tert-buty-2-hydroxy-5-methylphenyl)-5-chlorobenzotriazole (3.16 g, 10 mmol), tris(dibenzylideneacetone)dipalladium (0) (46.8 mg, 0.05 mmol), Xphos (97.3 mg, 0.2 mmol), potassium hydroxide (790 mg, 14 mmol), pyrrole (1.50 mL, 22 mmol) and an ion-exchange water (5 mL) were stirred under Ar and a heated condition at 100° C. for 24 hours. After the reaction was over, toluene and hydrochloric acid were added, a solid component was removed via suction filtration, and the solvent was then distilled away from a filtrate. A crude product obtained was purified by recrystallization to obtain a yellow solid as the target product.

FT-IR: 2975 cm$^{-1}$: O—H stretching vibration 1412 cm$^{-1}$, 1358 cm$^{-1}$: triazole ring stretching vibration $^1$H-NMR (CDCl$_3$:400 MHz): δ1.50 (s, 9H, —C—(C$\underline{H}_3$)$_3$), 2.40 (s, 3H, —C$\underline{H}_3$) 6.23 (t, 2H), 7.19 to 7.20 (m, 3H), 7.62 (d, 1H), 7.84 (s, 1H), 7.99 (d, 1H), 8.08 (s, 1H), 11.58 (s, 1H, —O$\underline{H}$)

$^{13}$C-NMR (CDCl$_3$:400 MHz): δ20.9 (—$\underline{C}$H$_3$), 29.5 (—C—($\underline{C}$H$_3$)$_3$), 35.4 (—$\underline{C}$—(CH$_3$)$_3$), 106.8, 111.2, 118.9, 119.4, 119.8, 123.1, 129.0 (CH$_{arom}$), 125.4, 140.0, 141.0, 143.1 ($\underline{C}_{arom}$), 128.4 ($\underline{C}_{arom}$—CH$_3$), 139.2 (—$\underline{C}_{arom}$—C—(CH$_3$)$_3$), 146.8 (—$\underline{C}_{arom}$—OH)

Synthesis Example 14

Synthesis of Compound 14

[Chemical formula 23]

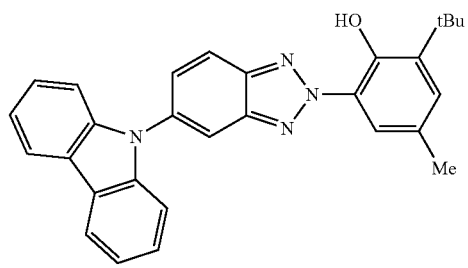

Here, 2-(3-tert-butyl-2-hydroxy-5-methylphenyl)-5-chlorobenzotriazole (3.23 g, 10 mmol), tris(dibenzylideneacetone)dipalladium (0) (48.9 mg, 0.05 mmol), Xphos (97.9 mg, 0.2 mmol), potassium hydroxide (768 mg, 14 mmol), carbazole (2.51 g, 22 mmol) and an ion-exchange water (5 mL) were stirred under Ar and a heated condition at 100° C. for 30 min, followed by adding toluene to then perform stirring under the heated condition for another 24 hours. After the reaction was over, toluene and hydrochloric acid were added, a solid component was removed via suction filtration, and the solvent was then distilled away from a filtrate. A crude product obtained was purified via column chromatography and recrystallization to obtain a yellow solid as the target product.

FT-IR: 2975 cm$^{-1}$: O—H stretching vibration 1402 cm$^{-1}$, 1370 cm$^{-1}$: triazole ring stretching vibration $^1$H-NMR (CDCl$_3$:400 MHz): δ1.52 (s, 9H, —C—(C$\underline{H}_3$)$_3$), 2.42 (s, 3H, —C$\underline{H}_3$), 7.23 (s, 1H), 7.34 (t, 2H), 743 to 7.50 (d, 4H), 7.69 (d, 1H), 8.13 to 8.16 (m, 5H), 11.61 (s, 1H, —OH)

$^{13}$C-NMR (CDCl$_3$:400 MHz): δ21.0 (—$\underline{C}$H$_3$), 29.6 (—C—($\underline{C}$H$_3$)$_3$), 35.5 (—$\underline{C}$—(CH$_3$)$_3$), 109.8, 115.1, 119.2, 119.5, 120.5, 120.5, 126.2, 127.6, 129.2 (CH$_{arom}$), 123.7, 125.4, 137.0, 140.8, 141.7, 143.2 ($\underline{C}_{arom}$), 128.5 ($\underline{C}_{arom}$—CH$_3$), 139.3 (—$\underline{C}_{arom}$—C—(CH$_3$)$_3$), 146.9 (—$\underline{C}_{arom}$—OH)

Synthesis Example 15

Synthesis of Compound 15

[Chemical formula 24]

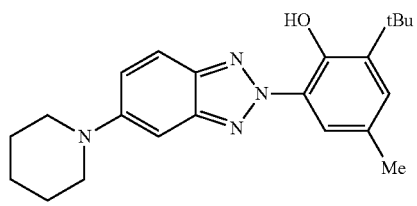 [SMILES: Cc1cc(-n2nc3ccc(N4CCCCC4)cc3n2)c(O)c(C(C)(C)C)c1]

Here, 2-(3-tert-butyl-2-hydroxy-5-methylpentyl)-5-chlorobenzotriazole (1.60 g, 5 mmol), tris(dibenzylideneacetone)dipalladium (0) (68.7 mg, 0.075 mmol), Xphos (73.0 mg, 0.15 mmol), sodium-tert-butoxide (1.44 g, 15 mmol), piperidine (852 mg, 10 mmol) and toluene (10 mL) were stirred under Ar and a heated condition at 70° C. for four hours. After the reaction was over, hydrochloric acid was added to then perform water washing, followed by removing a solid component via filtration, and then distilling away the solvent from a filtrate. A crude product obtained was purified via column chromatography and recrystallization to obtain a yellow solid as the target product.

FT-IR: 2975 cm$^{-1}$: O—H stretching vibration 1401 cm$^{-1}$, 1370 cm$^{-1}$: triazole ring stretching vibration $^1$H-NMR (CDCl$_2$:400 MHz): δ1.49 (s, 9H, —C—(CH$_3$)$_3$), 1.62 to 1.67 (m, 2H, —N—CH$_2$—CH$_2$—CH$_2$—), 1.77 (quin, 4H, —N—CH$_2$—CH$_2$—CH$_2$—), 2.37 (s, 3H, —CH$_3$), 3.25 (t, 4H, —N—CH$_2$—CH$_2$—CH$_2$—), 7.06 (s, 1H), 7.13 (s, 1H), 7.31 (d, 1H), 7.74 (d, 2H), 8.01 (s, 1H), 11.75 (s, 1H, —OH)

$^{13}$C-NMR (CDCl$_3$:400 MHz): δ20.9 (—CH$_3$), 24.2 (—N—CH$_2$—CH$_2$—CH$_2$—), 25.8 (—N—CH$_2$—CH$_2$—CH$_2$—), 29.6 (—C—(CH$_3$)$_3$), 35.3 (—C—(CH$_3$)$_3$), 51.2 (—N—CH$_2$—CH$_2$—CH$_2$—), 98.1, 117.5, 119.0, 123.9, 127.9 (CH$_{arom}$), 125.7, 128.0, 138.5, 144.3, 152.2 (C$_{arom}$), 127.9 (C$_{arom}$—CH$_3$), 138.9 (—C$_{arom}$—C—(CH$_3$)$_3$), 147.3 (—C$_{arom}$—OH)

Synthesis Example 16

Synthesis of Compound 16

[Chemical formula 25]

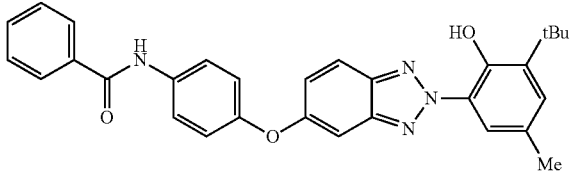

The intermediate 3 (409 mg, 1.92 mmol), the intermediate 1 (424 mg, 1.17 mmol), copper iodide (22.3 mg, 1.17×10$^{-2}$ mmol), the ligand (52.2 mg, 1.33×10$^{-2}$ mmol) and tripotassium phosphate (538 mg, 2.53 mmol) were dissolved in 4 mL of DMF, and stirred under Ar and a heated condition at 100° C. for 24 hours. After the reaction was over, there were performed dilution, filtration, liquid separation and solvent removal, followed carrying out column chromatography and recrystallization to obtain a white solid as the target product. The physical property values are shown below.

FT-IR: 2974 cm$^{-1}$: O—H stretching vibration 1643 cm$^{-1}$: C=O stretching vibration 1402 cm$^1$, 1370 cm$^{-1}$: triazole ring stretching vibration $^1$H-NMR (CDCl$_3$:400 MHz): δ1.49 (s, 9H, —C—(CH$_3$)$_3$) 2.38 (s, 3H, —CH$_3$—) 7.14 to 7.16 (m, 3H), 7.26 (s, 1H), 7.30 (d, 1H), 7.52 (t, 2H), 7.58 (t, 1H), 7.70 (d, 2H), 7.84 (s, 1H, CONH), 7.90 (m, 3H), 8.03 (s, 1H), 11.58 (s, 1H, —OH)

$^{13}$C-NMR (CDCl$_3$:400 MHz): δ20.9 (—CH$_3$), 29.5 (—C—(CH$_3$)$_3$), 35.4 (—C—(CH$_3$)$_3$), 102.1, 119.0, 119.2, 120.5, 122.1, 122.5, 127.0, 128.6, 128.9, 132.0 (CH$_{arom}$), 125.5, 134.4, 134.9, 139.7, 143.3, 152.7, 157.7 (C$_{arom}$) 128.2 (C$_{arom}$—CH$_3$), 139.1 (—C$_{arom}$—C(CH$_3$)$_3$), 146.6 (—C$_{arom}$—OH), 165.7 (—CONH—)

Synthesis Example 17

Synthesis of Compound 17

[Chemical formula 25]

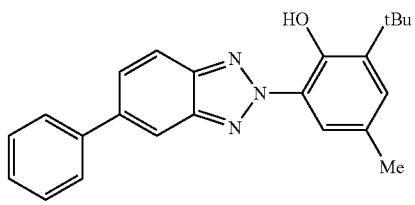 [SMILES: Cc1cc(-n2nc3ccc(-c4ccccc4)cc3n2)c(O)c(C(C)(C)C)c1]

Phenylboronic acid (1.35 g, 11 mmol), 2-(3-tert-butyl-2-hydroxy-5-methylphenyl)-5-chlorobenzotriazole (3.15 g, 10 mmol), tris(dibenzylideneacetone)dipalladium (0) (90 mg, 0.1 mmol), Xphos (190 mg, 0.4 mmol) and potassium carbonate (3.32 g, 24 mmol) were stirred in 150 mL of 1-butanol under Ar and a heated condition at 100° C. for two hours. After the reaction was over, filtration was performed, a filtrate was then cooled to obtain a white solid product.

FT-IR: 2962 cm$^{-1}$: O—H stretching vibration 1443 cm$^{-1}$, 1392 cm$^-$: triazole ring stretching vibration $^1$H-NMR (CDCl$_2$:400 MHz): δ1.51 (s, 9H, —C—(CH$_3$)$_3$), 2.40 (s, 3H, —CH$_3$), 7.19 (s, 1H), 7.42 (t, 1H), 7.51 (t, 2H), 7.69 (d, 2H), 7.75 (d, 1H), 7.99 (d, 1H), 8.08 (s, 1H), 8.12 (s, 1H), 11.77 (s, —OH)

$^{13}$C-NMR (CDCl$_3$:400 MHz): δ20.9 (—CH$_3$), 29.6 (—C—(CH$_3$)$_3$), 35.4 (—C—(CH$_3$)$_3$), 114.9, 117.7, 119.4, 127.5, 127.9, 128.4, 128.8, 129.0 (CH$_{arom}$), 125.5, 140.6, 141.0, 142.2, 143.3 (C$_{arom}$), 128.3 (C$_{arom}$—CH$_3$), 139.2 (—C$_{arom}$—C—(CH$_3$)$_3$) 1468 (—C$_{arom}$—OH)

Synthesis Example 18

Synthesis of Compound 18

[Chemical formula 27]

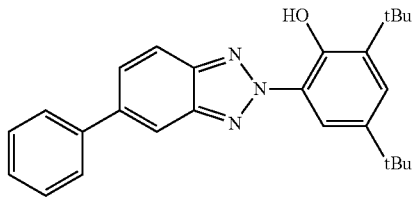

Phenylboronic acid (2.70 g, 22 mmol), 2-(3-tert-butyl-2-hydroxy-5-methylphenyl)-5-chlorobenzotriazole (7.15 g, 20 mmol), tris(dibenzylideneacetone)dipalladium (0) (180 mg, 0.2 mmol), Xphos (380 mg, 0.8 mmol) and potassium carbonate (6.64 g, 48 mmol) were stirred in 200 mL of 1-butanol under Ar and a heated condition at 100° C. for two hours. After the reaction was over, filtration was performed, a filtrate was then cooled to obtain a white solid product.

FT-IR: 2959 cm$^{-1}$: O—H stretching vibration 1457 cm$^{-1}$, 1370 cm$^{-1}$: triazole ring stretching vibration $^1$H-NMR (CDCl$_3$:400 MHz): δ1.41 (s, 9H, —C—(CH$_3$)$_3$), 1.53 (s, 9H, —C—(CH$_3$)$_3$), 7.42 to 7.44 (m, 2H), 7.51 (t, 2H), 7.70 (d, 2H), 7.76 (d, 1H), 8.00 (d, 1H), 8.10 (s, 1H), 8.31 (s, 1H), 11.78 (s, 1H, —OH)

$^{13}$C-NMR (CDCl$_3$:400 MHz): δ29.6, 31.5 (—C—(CH$_3$)$_3$), 34.6, 35.7 (—C—(CH$_3$)$_3$) 114.9, 116.1, 117.8, 125.2, 127.5, 127.9, 128.3, 129.0 (CH$_{arom}$), 1253, 140.7, 140.8, 142.2, 143.3 (C$_{arom}$), 138.6, 141.7 (—C$_{arom}$—C—(CH$_3$)$_3$), 146.7 (—C$_{arom}$—OH)

Synthesis Example 19

Synthesis of Compound 19

[Chemical formula 28]

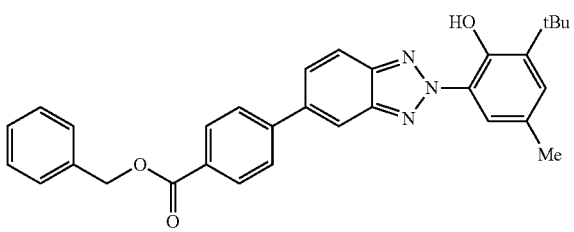 [SMILES: Cc1cc(-n2nc3ccc(-c4ccc(C(=O)OCc5ccccc5)cc4)cc3n2)c(O)c(C(C)(C)C)c1]

The intermediate 1 (0.10 g, 0.28 mmol), 4-(benzyloxycarbonyl)phenylboronic acid (0.0746 g, 0.29 mmol), palladium acetate (0.0025 g, 0.0111 mmol), triphenylphosphine (0.0087 g, 0.0333 mmol) and sodium carbonate (0.0706 g, 0.0666 mmol) were added and dried under a reduced pressure for two hours, followed by adding thereto propanol/water (7.7 mL/0.3 mL) under a nitrogen atmosphere, and then performing stirring under a heated condition and such atmosphere at 90 to 100° C. for 24 hours. After the reaction was over, an acid treatment was carried out, and a precipitate obtained was then filtrated before being subjected to column purification, thereby obtaining a white solid as the target product.

FT-IR: 2866 cm$^{-1}$: O—H stretching vibration 1716 cm$^{-1}$: C=O stretching vibration 1447 cm$^{-1}$, 1357 cm$^{-1}$: triazole ring stretching vibration $^1$H-NMR (CDCl$_3$:400 MHz): δ1.51 (s, 9H, —C—(CH$_3$)$_3$), 2.40 (s, 3H, —CH$_3$), 5.41 (s, 2H, —CH$_2$—), 7.20 (s, 1H), 7.40 to 7.44 (m, 3H), 7.48 (d, 2H), 7.75 (d, 3H), 8.00 (d, 2H), 8.11 (d, 2H), 8.21 (d, 2H), 11.68 (s, 1H, —OH)

$^{13}$C-NMR (CDCl$_3$:400 MHz): δ20.9 (—CH$_3$), 29.6 (—C—(CH$_3$)$_3$), 35.4 (—C—(CH$_3$)$_3$), 115.6, 118.1, 119.5, 128.3, 128.7, 129.0, 130.5 (CH$_{arom}$), 66.9, 127.5, 128.0, 128.2, 136.1, 143.2, 145.1 (C$_{arom}$), 128.2 (C$_{arom}$—CH$_3$), 139.3 (—C$_{arom}$—C—(CH$_3$)$_3$) 146.9 (—C$_{arom}$—OH), 167.0 (—COO—)

Synthesis Example 20

Synthesis of Compound 20

[Chemical formula 29]

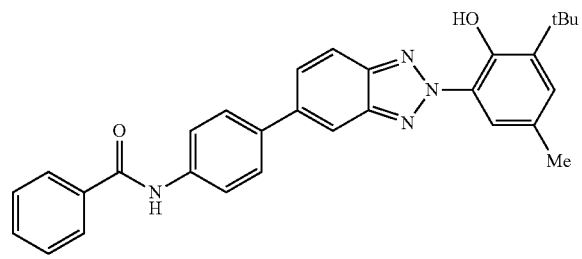 [SMILES: Cc1cc(-n2nc3ccc(-c4ccc(NC(=O)c5ccccc5)cc4)cc3n2)c(O)c(C(C)(C)C)c1]

The intermediate 1 (0.10 g, 0.28 mmol), 4-(phenylcarbamoyl)phenylboronic acid (0.0746 g, 0.29 mmol), palladium acetate (0.0025 g, 0.0111 mmol), triphenylphosphine (0.0087 g, 0.0333 mmol) and sodium carbonate (0.0706 g, 0.0666 mmol) were added and dried under a reduced pressure for two hours, followed by adding thereto propanol/water (7.7 mL/0.3 mL) under a nitrogen atmosphere, and then performing stirring under a heated condition and such atmosphere at 90 to 100° C. for 24 hours. After the reaction was over, an acid treatment was carried out, and a precipitate obtained was then filtrated before being subjected to column purification, thereby obtaining a white solid as the target product.

FT-IR: 2952 cm$^{-1}$: O—H stretching vibration 1656 cm$^{-1}$: C=O stretching vibration 1441 cm$^{-1}$, 1355 cm$^{-1}$: triazole ring stretching vibration $^1$H-NMR (CDCl$_3$:400 MHz): δ1.51 (s, 91, —C—(CH3)$_3$), 2.41 (s, 3H, —CH$_3$), 7.21 (s, 1H, CONH), 7.12 to 7.21 (m, 1H), 7.41 (t, 1H), 7.68 (d, 2H), 7.77 (d, 1H), 7.83 (m, 3H), 8.05 (m, 3H), 8.15 (d, 2H), 11.67 (s, 1H, —OH)

$^{13}$C-NMR (CDCl$_3$:400 MHz): δ20.9 (—CH$_3$), 29.6 (—C—(CH$_3$)$_3$), 35.4 (—C—(CH$_3$)$_3$) 115.6, 119.5, 119.5, 120.5, 127.5, 128.2, 128.7, 129.0, 130.5, 136.0 (CH$_{arom}$) 66.9, 125.5, 134.4, 134.9, 139.3, 139.7, 143.3, 145.1, 157.7 (C$_{arom}$), 128.4 (C$_{arom}$—CH$_3$), 139.3 (—C$_{arom}$—C—(CH$_3$)$_3$), 146.9 (—C$_{arom}$—OH) 166.2 (—CONH—)

Synthesis Example 21

Synthesis of Compound 21

[Chemical formula 30]

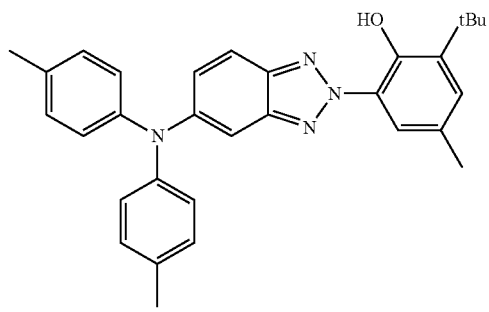

Palladium acetate (22.0 mg, 0.1 mmol), Xphos (95.2 mg, 0.2 mmol), an ion-exchange water (10 μL), 7.5 g of tert-butyl alcohol, 7.5 g of toluene, 2-(3,5-di-tert-butyl-2-hydroxyphenyl)-5-chlorobenzotriazole (3.16 g, 10 mmol), potassium carbonate (1.93 g, 14 mmol) and ditolylamine (3.95 g, 20 mmol) were added, and stirred under a heated condition for 48 hours. After the reaction was over, water, toluene and hydrochloric acid were added, water washing was performed, and the solvent was then distilled away from a filtrate. A crude product obtained was purified via column chromatography and recrystallization to obtain a yellow solid as the target product.

FT-IR: 2974 cm$^{-1}$: O—H stretching vibration 1454 cm$^{-1}$, 1370 cm$^{-1}$: triazole ring stretching vibration $^1$H-NMR (CDCl$_3$:400 MHz): δ1.47 (s, 9H, —C—(C$\underline{H}_3$)$_3$), 2.34 (s, 6H, —C$\underline{H}_3$), 2.36 (s, 3H, —C$\underline{H}_3$), 7.05 (d, 4$\underline{H}$), 7.06 to 7.12 (m, 5$\underline{H}$), 7.26 (m, 1H), 7.70 (d, 1H), 7.99 (s, 1H), 11.66 (s, 1H, —O$\underline{H}$)

$^{13}$C-NMR (CDCl$_2$:400 MHz): δ20.9 (—$\underline{C}$H$_3$), 29.5 (—C—($\underline{C}$H$_3$)$_3$), 35.4 (—$\underline{C}$—(CH$_3$)$_3$), 105.4, 117.0.5, 119.0, 125.3, 126.2, 128.1, 130.1 ($\underline{C}$H$_{arom}$), 125.6, 133.6, 138.9, 143.9, 144.9, 118.2 ($\underline{C}_{arom}$), 128.1 ($\underline{C}_{arom}$—CH$_3$), 139.4 (—$\underline{C}_{arom}$—C—(CH$_3$)$_3$), 146.5 (—$\underline{C}_{arom}$—OH)

Synthesis Example 22

Synthesis of Compound 22

[Chemical formula 31]

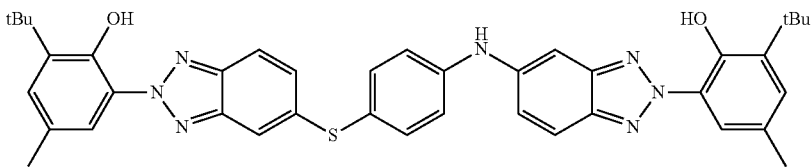

Palladium acetate (11.0 mg, 0.05 mmol), Xphos (48 mg, 0.1 mmol), anion-exchange water (5 μL), 7.5 g of tert-butyl alcohol, 2-(3,5-di-tert-butyl-2-hydroxyphenyl)-5-chlorobenzotriazole (1.57 g, 5 mmol), potassium carbonate (1.93 g, 14 mmol) and the intermediate 5 (2.02 g, 5 mmol) were added, and stirred under a heated condition for 24 hours. After the reaction was over, water, toluene and hydrochloric acid were added, water washing was performed, and the solvent was then distilled away from a filtrate. A crude product obtained was purified by recrystallization to obtain a yellow solid as the target product.

FT-IR: 2974 cm$^{-1}$: O—H stretching vibration 1428 cm$^{-1}$ 1359 cm$^{-1}$: triazole ring stretching vibration $^1$H-NMR (CDCl$_3$:400 MHz): δ1.48 (s, 9H, —C—(C$\underline{H}_3$)$_3$), 1.49 (s, 9H, —C—(C$\underline{H}_3$)$_3$), 2.37 (s, 3H, —C$\underline{H}_3$), 2.38 (s, 31H, —C$\underline{H}_3$), 6.12 (s, 1H, —N$\underline{H}$—), 7.16 (s, 2$\underline{H}$), 7.21 to 7.27 (m, 3H), 7.36 (dd, 1H), 7.51 to 7.56 (m, 4H), 7.82 (d, 1H), 7.86 (d, 1H), 8.34 (s, 2H), 11.59 (s, 1H, —O$\underline{H}$), 11.66 (s, 1H, —O$\underline{H}$)

$^{13}$C-NMR (CDCl$_3$:400 MHz): δ20.9 (—$\underline{C}$H$_3$), 29.5 (—C—($\underline{C}$H$_3$)$_3$), 35.4 (—$\underline{C}$—(CH$_3$)$_3$), 100.5, 114.4, 117.8, 118.7, 119.0, 119.1, 119.3, 123.6, 128.4, 128.5, 128.7, 136.0 ($\underline{C}$H$_{arom}$), 123.7, 125.4, 125.5, 139.0, 139.1, 141.4, 141.7, 143.3, 143.8 ($\underline{C}_{arom}$), 128.2, 128.3 ($\underline{C}_{arom}$—CH$_3$), 139.47, 139.51 (—$\underline{C}_{arom}$—C—(CH$_3$)$_3$), 146.5, 146.7 (—$\underline{C}_{arom}$—OH)

Synthesis Example 23

Synthesis of Compound 23

[Chemical formula 32]

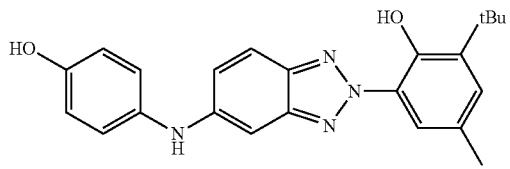

Palladium acetate (112 mg, 0.5 mmol), Xphos (476 mg, 1.0 mmol), an ion-exchange water (50 μL), 80 g of tert-butyl alcohol, 2-(3,5-di-tert-butyl-2-hydroxyphenyl)-5-chlorobenzotriazole (15.8 g, 50 mmol), potassium carbonate (9.67 g, 70 mmol) and 4-aminophenol (9.82 g, 90 mmol) were added, and stirred under a heated condition for four hours. After the reaction was over, water, toluene and hydrochloric acid were added, water washing was performed, and the solvent was then distilled away from a filtrate. A crude product obtained was purified by recrystallization to obtain a yellow solid as the target product.

FT-IR: 3219 cm$^{-1}$, 3034 cm$^{-1}$: O—H stretching vibration 1441 cm$^{-1}$, 1373 cm$^{-1}$: triazole ring stretching vibration $^1$H-NMR (CDCl$_3$:400 MHz): δ1.48 (s, 9H, —C—(C$\underline{H}_3$)$_3$), 2.36 (s, 3H, —C$\underline{H}_3$), 4.75 (s, 1H, —O$\underline{H}$), 5.74 (s, 1$\underline{H}$, —N$\underline{H}$—), 6.86 (d, 2$\underline{H}$), 7.05 to 7.15 (m, 5H), 7.75 (d, 1H), 7.99 (s, 1H), 11.71 (s, 1H, —O$\underline{H}$)

$^{13}$C-NMR (CDCl$_3$:400 MHz): δ20.9 (—$\underline{C}$H$_3$) 29.5 (—C—($\underline{C}$H$_3$)$_3$) 35.3 (—$\underline{C}$—(CH$_3$)$_3$) 95.2, 116.3, 118.4, 122.4, 123.9, 128.0 ($\underline{C}$H$_{arom}$), 125.6, 134.5, 138.7, 144.2, 145.2, 152.1 ($\underline{C}_{arom}$), 128.1 ($\underline{C}_{arom}$—CH$_3$), 138.9 (—$\underline{C}_{arom}$—C—(CH$_3$)$_3$), 146.4 (—$\underline{C}_{arom}$—OH)

Synthesis Example 24

Synthesis of Compound 24

[Chemical formula 33]

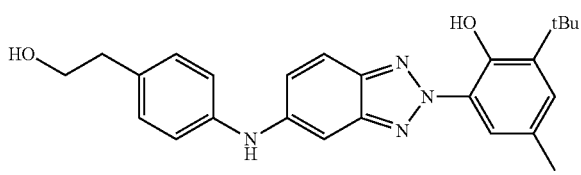

Palladium acetate (112 mug, 0.5 mmol), Xphos (476 mg, 1.0 mmol), an ion-exchange water (50 μL), 80 g of tert-butyl alcohol, 2-(3,5-di-tert-butyl-2-hydroxyphenyl)-5-chlorobenzotriazole (15.8 g, 50 mmol), potassium carbonate (9.67 g, 70 mmol) and 2-(4-aminophenyl)ethanol (10.36 g, 75 mmol) were added, and stirred under a heated condition for four hours. After the reaction was over, water, toluene and hydrochloric acid were added, water washing was performed, and the solvent was then distilled away from a filtrate. A crude product obtained was purified by recrystallization to obtain a yellow solid as the target product.

FT-IR: 3237 cm$^{-1}$, 3042 cm$^1$: O—H stretching vibration 1453 cm$^{-1}$, 1375 cm$^{-1}$: triazole ring stretching vibration $^1$H-NMR (CDCl$_3$:400 MHz): δ1.42 (t, 1H, —OH), 1.49 (s, 9H, —C—(CH$_3$)$_3$), 2.37 (s, 3H, —CH$_3$), 2.87 (t, 2H, —CH$_2$—), 3.88 (q, 2H, —CH$_2$—), 5.92 (s, 1H, —NH—), 7.16 to 7.23 (m, 6H), 7.36 (s, 1H), 7.79 (d, 1H), 8.01 (s, 1H), 11.70 (s, 1H, —OH)

$^{13}$C-NMR (CDCl$_3$:400 MHz): δ20.9 (—CH$_3$), 29.5 (—C—(CH$_3$)$_3$), 35.4 (—C—(CH$_3$)$_3$), 38.6, 63.8 (—CH$_2$—), 93.74, 118.5, 119.0, 120.1, 123.0, 128.1, 130.1 (CH$_{arom}$), 125.6, 132.8, 138.9, 139.0, 140.3, 143.5, 144.1, 148.2 (C$_{arom}$) 146.4 (—C$_{arom}$—OH)

Synthesis Example 25

Synthesis of Compound 25

[Chemical formula 34]

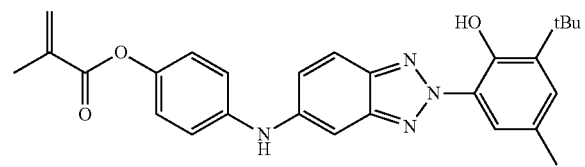

Methacryloyl chloride (590 mg, 5.5 mmol) was put into a beaker containing the compound 23 (1.94 g, 5 mmol), triethylamine (660 mg, 6.5 mmol) and 20 mL of toluene, followed by stirring them at room temperature for 30 min. After the reaction was over, hexane was added thereto, a solid precipitated was then collected and later washed with methanol before being dissolved in ethyl acetate. After washing an organic layer with water, recrystallization was performed to obtain a yellow solid as the target product.

FT-IR: 3043 cm$^{-1}$: O—H stretching vibration 1755 cm$^{-1}$: C═O stretching vibration 1444 cm$^{-1}$, 1375 cm$^{-1}$: triazole ring stretching vibration $^1$H-NMR (CDCl$_3$:400 MHz): δ1.49 (s, 9H, —C—(CH$_3$)$_3$) 2.08 (s, 3H, —CH$_3$), 2.37 (s, 3H, —CH$_3$), 5.77 (s, 1H), 5.95 (s, 1H, —NH—), 6.37 (s, 1H), 7.10 to 7.23 (m, 6H), 7.37 (s, 1H), 7.80 (d, 1H), 8.02 (s, 1H), 11.68 (s, 1H, —OH)

$^{13}$C-NMR (CDCl$_3$:400 MHz): δ18.4, 20.9 (—CH$_3$), 29.5 (—C—(CH$_3$)$_3$), 35.4 (—C—(CH$_3$)$_3$), 97.8, 118.6, 119.0, 120.6, 122.6, 123.0, 128.2 (CH$_{arom}$), 125.6 (═CH$_2$), 135.9, 139.0, 139.1, 143.3, 144.0, 146.0, 146.4 (C$_{arom}$), 127.2 (C$_{arom}$—CH$_3$), 139.5 (—C$_{arom}$—C—(CH$_3$)—), 166.1 (—CO—)

Synthesis Example 26

Synthesis of Compound 26

[Chemical formula 35]

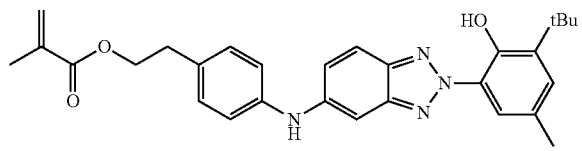

Methacryloyl chloride (590 mg, 5.5 mmol) was put into a beaker containing the compound 24 (2.09 g, 5 mmol), triethylamine (660 ng, 6.5 mmol) and 20 mL of toluene, followed by stirring them at room temperature for 20 hours. After the reaction was over, hexane was added thereto, and a solid precipitated was then collected. The solid was later dissolved in ethyl acetate, toluene, hexane and methanol, and an upper layer was then collected before being dissolved in ethyl acetate. After washing an organic layer with water, recrystallization was performed to obtain a yellow solid as the target product.

FT-IR: 3041 cm$^{-1}$: O—H stretching vibration 1762 cm$^{-1}$: C═O stretching vibration 1451 cm$^{-1}$, 1353 cm$^{-1}$: triazole ring stretching vibration $^1$H-NMR (CDCl$_3$:400 MHz): δ1.49 (s, 9H, —C—(CH$_3$)$_3$), 1.95 (s, 3H, —CH$_3$) 2.37 (s, 3H, —CH$_3$) 298 (t, 2H, —CH$_2$—), 4.36 (t, 2H, —CH$_2$—), 5.57 (s, 1H), 5.92 (s, 1H, —NH—), 6.11 (s, 1H), 7.13 to 7.17 (m, 4H), 7.23 (d, 2H), 7.36 (s, 1H), 7.79 (d, 1H), 8.01 (s, 1H), 11.69 (s, 1H, —OH)

$^{13}$C-NMR (CDCl$_3$:400 MHz): δ18.3, 20.9 (—CH$_3$), 29.5 (—C—(CH$_3$)$_3$), 34.5, 65.3 (—CH$_2$—), 35.6 (—C—(CH$_3$)$_3$), 97.4, 118.5, 119.0, 119.9, 123.1, 130.1 (CH$_{arom}$), 125.5 (═CH$_2$), 132.3, 136.4, 138.9, 140.3, 143.4, 144.1, 146.4 (C$_{arom}$), 128.1 (C$_{arom}$—CH$_3$), 139.0 (—C$_{arom}$—C—(CH$_3$)$_3$), 166.1 (—CO—)

Synthesis Example 27

Synthesis of Compound 27

[Chemical formula 36]

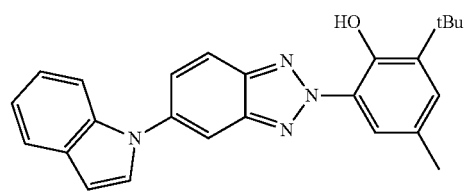

Palladium acetate (22.0 mg, 0.1 mmol), Xphos (95.2 mg, 0.2 mmol), an ion-exchange water (10 μL), 7.5 mL of tert-butyl alcohol, 7.5 mL of toluene, 2-(3,5-di-tert-butyl-2-hydroxyphenyl)-5-chlorobenzotriazole (3.16 g, 10 mmol), potassium carbonate (1.93 g, 14 mmol) and indole (2.34 g, 20 mmol) were added, and stirred under a heated condition for 24 hours. After the reaction was over, water, toluene and hydrochloric acid were added, water washing was performed, and the solvent was then distilled away from a filtrate. A crude product obtained was purified by recrystallization to obtain a yellow solid as the target product.

FT-IR: 2976 cm$^{-3}$: O—H stretching vibration 1437 cm$^{-1}$, 1372 cm$^{-1}$: triazole ring stretching vibration $^1$H-NMR (CDCl$_3$:400 MHz): δ1.51 (s, 9H, —C—(CH$_3$)$_3$), 2.41 (s, 3H, —CH$_3$), 6.76 (d, 1H), 7.21 to 7.28 (m, 3H), 7.44 (d, 1H), 7.64 to 7.74 (m, 3H), 8.00 (s, 1H), 8.07 (d, 1H), 8.12 (s, 1H), 11.60 (s, 1H, —OH)

$^{13}$C-NMR (CDCl$_3$:400 MHz): δ21.0 (—CH$_3$), 29.6 (—C—(CH$_3$)$_3$), 35.4 (—C—(CH$_3$)$_3$), 104.6, 110.5, 111.3, 119.0, 119.5, 120.9, 121.4, 122.8, 125.8, 127.9, 129.1 (CH$_{arom}$) 125.4, 129.5, 135.9, 139.1, 141.2, 143.1 (C$_{arom}$) 128.5 (C$_{arom}$—CH$_3$), 139.3 (—C$_{arom}$—C—(CH$_3$)$_3$), 146.8 (—C$_{arom}$—OH)

Synthesis Example 28

Synthesis of Compound 28

[Chemical formula 37]

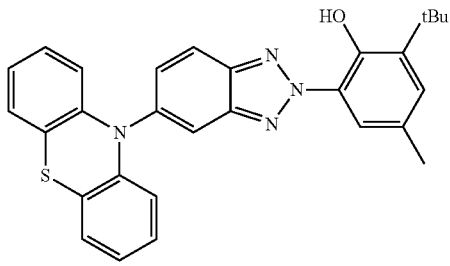

Palladium acetate (44.0 mg, 0.2 mmol) Xphos (192 ng, 0.4 mmol), an ion-exchange water (20 μL), 15 g of tert-butyl alcohol, 15 g of toluene, 2-(3,5-di-tert-butyl-2-hydroxyphenyl)-5-chlorobenzotriazole (6.31 g, 20 mmol), potassium carbonate (3.86 g, 28 mmol) and phenothiazine (5.18 g, 26 mmol) were added, and stirred under a heated condition for 24 hours. After the reaction was over, water, toluene and hydrochloric acid were added, water washing was performed, and the solvent was then distilled away from a filtrate. A crude product obtained was purified by recrystallization to obtain a yellow solid as the target product. It was confirmed that the 5% weight reduction temperature of this compound was 348° C., and that the wavelength at the maximum absorption peak in the wavelength region of 350 to 430 nm (maximum absorption wavelength: λ$_{max}$) was 354 nm.

FT-IR: 2957 cm$^{-1}$: O—H stretching vibration 1465 cm$^{-1}$, 1310 cm$^{-1}$: triazole ring stretching vibration $^1$H-NMR (CDCl$_3$:400 MHz): δ1.55 (s, 9H, —C—(CH$_3$)$_3$), 2.41 (s, 6H, —CH$_3$), 6.39 (d, 2H), 6.87 to 6.94 (m, 4H), 7.11 (d, 2H), 7.21 (s, 1H), 7.45 (d, 1H), 7.95 (s, 1H), 8.12 (m, 2H), 11.66 (s, 1H, —OH)

$^{13}$C-NMR (CDCl$_3$:400 MHz): δ20.9 (—CH$_3$), 29.5 (—C—(CH$_3$)$_3$), 35.4 (—C—(CH$_3$)$_3$), 117.4, 117.6, 119.5, 119.9, 123.3, 127.0, 127.2, 129.1, 129.9 (CH$_{arom}$), 122.1, 125.4, 140.8, 141.7, 143.8, 146.8 (C$_{arom}$), 128.5 (C$_{arom}$—CH$_3$), 139.3 (—C$_{arom}$—C—(CH$_3$)$_3$)

Synthesis Example 29

Synthesis of Compound 31

[Chemical formula 38]

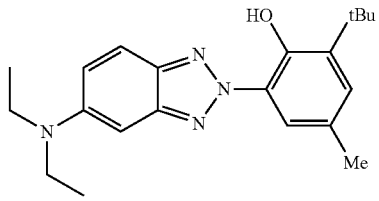 [SMILES: CCN(CC)c1ccc2nn(-c3cc(C)cc(C(C)(C)C)c3O)nc2c1]

Here, 2-(3-tert-butyl-2-hydroxy-5-methylphenyl)-5-chlorobenzotriazole (1.58 g, 5 mmol), tris(dibenzylideneacetone)dipalladium (0) (68.7 mg, 0.075 mmol), Xphos (713.1 mg, 0.15 mmol), sodium-tert-butoxide (1.44 g, 15 mmol), diethylamine (732 mg, 10 mmol) and toluene (10 mL) were stirred under Ar and a heated condition at 70° C. for four hours. After the reaction was over, hydrochloric acid was added to then preform water washing, followed by removing a solid component via filtration, and then distilling away the solvent from a filtrate. A crude product obtained was purified via column chromatography and recrystallization so as to obtain a yellow solid as the target product.

FT-IR: 2975 cm$^{-1}$: O—H stretching vibration 1401 cm$^{-1}$, 1370 cm$^{-1}$: triazole ring stretching vibration $^1$H-NMR (CDCl$_3$:400 MHz): δ1.24 (t, 6H, —CH$_2$—CH$_3$), 1.50 (s, 9H, —C—(CH$_3$)$_3$), 2.38 (s, 3H, CH$_3$), 2.46 (q, 4H, —CH$_2$—CH$_3$) 6.77 (s, 1H), 7.11 (s, 1H), 7.14 (d, 1H), 7.73 (d, 2H), 8.00 (s, 1H), 11.87 (s, 1H, —OH)

$^{13}$C-NMR (CDCl$_3$:400 MHz): δ12.6 (—N—CH$_2$—CH$_3$), 20.9 (—CH$_3$), 29.6 (—C—(CH$_3$)$_3$), 35.3 (—C—(CH$_3$)$_3$), 45.0 (—N—CH$_2$—CH$_3$), 92.1, 117.8, 118.9, 119.7, 127.6 (CH$_{arom}$), 117.6, 123.7, 137.1, 145.0, 146.3 (C$_{arom}$), 127.9 (C$_{arom}$—CH$_3$) 138.4 (—C$_{arom}$—C—(CH$_3$)$_3$), 147.6 (—C$_{arom}$—OH)

Here, as compounds 29 and 30, there were used those produced by Tokyo Chemical Industry Co., Ltd.

(2) 5% Weight Reduction Temperature

A simultaneous thermogravimetric analyzer (TG/DTA6200 by Seiko Instruments Inc.) was used to measure changes in weight with regard to the compound(s) of the present invention at a temperature rise rate of 10° C./min and in a measurement range of 250 to 550° C.; a temperature at which the weight had decreased by 5% was read via thermogravimetry (TG) (Tables 1A to 1D).

As comparted to the compounds 29, 30 as 2-phenylbenzotriazole derivatives having no bonding group represented by the formula (I) or (II) and the compound 31 (244° C.) of a comparative example 3 having no Y$^1$ (Y$^1$ is an alkyl group), it was confirmed that the ultraviolet absorber compounds 1 to 28 of the present invention having the bonding group represented by the Y-containing formula (I) or the formula (II) had a high 5% weight reduction temperature of not lower than 250° C. i.e. the compounds 1 to 28 were superior in heat resistance.

Particularly, since there exists a correlation that compound 20 (380° C.)>compound 16 (352° C.), and a correlation that compound 1 (292° C.)>compound 17 (271° C.), the compounds were superior in heat resistance in an order of X being an oxygen atom<1=0<X being a nitrogen atom in the formula (I).

Further, the compound 1 (292° C.), compound 2 (322° C.), compound 3 (300° C.), compound 4 (326° C.), compound 5 (284° C.), compound 6 (290° C.), compound 7 (348° C., compound 8 (280° C.), compound 10 (374° C.), compound 11 (382° C.), compound 12 (319° C.), compound 14 (329° C.), compound 16 (352° C.), compound 19 (346° C.), compound 20 (380° C.), compound 21 (324° C.), compound 22 (356'C), compound 23 (302° C.), compound 24 (327° C.), compound 25 (339° C.), compound 26 (336° C.), compound 27 (297° C.) and compound 28 (348° C.) all exhibited a 5% weight reduction temperature of not lower than 280° C. The compound 2 (322° C.), compound 3 (300° C.), compound 4 (326° C.), compound 7 (348° C.), compound 10 (374° C.), compound 11 (382° C.), compound 12 (319° C.), compound 14 (329° C.), compound 16 (352° C.), compound 19 (346° C.), compound 20 (380° C.), compound 21 (324° C.), compound 22 (356° C.), compound 23 (302° C.), compound 24 (327° C.), compound 25 (339° C.), compound 26 (336° C.) and compound 28 (348° C.) all exhibited a 5% weight reduction temperature of not lower than 300° C. Moreover, as for the formula (I), the compounds in which (l==1, X is a nitrogen atom), and the molecular weight of $Y^1$ is not smaller than 190 (compound 7: 348° C., compound 10: 374° C., compound 11: 382° C. compound 22: 356° C.), the compounds in which (l=1, X is an oxygen atom) or (l=0), and an oxygen-containing group(s) has been introduced into $Y^1$ (compound 16: 352° C., compound 19: 346° C., compound 20: 380° C.), and the compounds having a bicyclic or more complex hetero atom (nitrogen atom, oxygen atom)-containing hetero or condensed ring in $Y^1$ of the formula (I) (compound 7: 348° C., compound 11: 382° C., compound 22: 356° C.; especially, the compound 11 having a tricyclic or more complex ring was superior) were all superior in heat resistance by exhibiting a 5% weight reduction temperature of not lower than 340° C. As for the formula (II), the hetero ring compound having a hetero atom(s) (sulfur atom) (compound 28: 348° C.) was superior in heat resistance by exhibiting a 5% weight reduction temperature of not lower than 340° C.

Further, there is a correlation that compound 1 (292° C.)>compound 6 (290° C.)>compound 5 (284° C.) thus it was indicated that the heat resistance would be improved in an order of $Y^1$ being a hydrogen atom>aromatic hydrocarbon group>aliphatic hydrocarbon group; and there is a correlation that compound 14 (tricyclic: 329° C.), compound 28 (tricyclic: 348° C.)>compound 27 (bicyclic 297° C.)>compound 15 (monocyclic: 260° C.), compound 13 (monocyclic: 258° C.), thus it was indicated that the larger the number of the rings composing the polycyclic ring in the formula (II), the more significantly the heat resistance would be improved.

Further, since there are a correlation that compound 19 (346° C.), compound 20 (380° C.)>compound 17 (271° C.), a correlation that compound 10 (374° C.)>compound 1 (292° C.), and a correlation that compound 22 (356° C.), compound 7 (348° C.)>compound 1 (292'C), a superior heat resistance was exhibited when $Y^1$ in the formula (I) was an aromatic hydrocarbon group having a substituent group(s) whose base end was an ester group or amide group, or when $Y^1$ in the formula (I) was an aromatic hydrocarbon group having a substituent group(s) whose base end was a sulfur-containing group or a nitrogen-containing group.

Since there is a correlation that compound 11 (382° C.), compound 4 (326° C.)>compound 1 (292° C.), it was indicated that the heat resistance would be improved when the aromatic hydrocarbon group represented by $Y^1$ in the formula (T) contained a bicyclic or more complex condensed ring; or when a substituent group(s) was present in such aromatic hydrocarbon group, and this substituent group (s) formed a ring together with the aromatic hydrocarbon group.

(3) Wavelength, Molar Extinction Coefficient, Peak Gradient (Absolute Value) at Maximum Absorption Peak in Wavelength Region of 350 to 430 nm Each of the compounds 1, 2, 4 to 6, 8 to 21, 23 to 27 and 29 to 31 was diluted with chloroform at 100 μM, and each of the compounds 3, 7 and 22 was diluted with chloroform at 50 μM. The compounds were then each put into a 10 mm quartz cell, and an ultraviolet-visual-near-infrared spectrophotometer (UH4150V by Hitachi High-Tech Science Corporation) was used to measure the absorption spectra thereof from which a wavelength at the maximum absorption peak in the wavelength region of 350 to 430 nm (maximum absorption wavelength: $\lambda_{max}$) was then read (Tables 1A to 1D). Further, molar extinction coefficients at these peaks (maximum molar extinction coefficient: $\varepsilon_{max}$) were calculated by the following formula. (Tables 1A to 1D).

Molar extinction coefficient: $\varepsilon_{max}$ (L/(mol·cm))=A: Absorbance/[c: Molar concentration (mol/L)×1: Cell optical path length (cm)]

Further, with a point of intersection between theses absorption spectra and a baseline (line at which the gradient of an absorption spectrum in 350 to 550 nm is 0) serving as a peak end (e.g. FIG. 1), the absolute value of the gradient of an absorption peak in the wavelength region of 350 to 430 nm on the long-wavelength side was calculated by the following formula (Tables 1A to 1D).

As for the compound 11, since absorptions were also observed at and beyond 430 nm, it was difficult to draw a baseline: an end point at the maximum absorption peak in the wavelength region of 350 to 430 nm was regarded as a peak end.

|Gradient of maximum absorption peak on long-wavelength side in wavelength region of 350 to 430 nm|=|(Absorbance at peak end−Absorbance at maximum absorption peak in wavelength region of 350 to 430 nm)/(Absorption wavelength at peak end−Wavelength at maximum absorption peak in wavelength region of 350 to 430 nm)|

As a result, in the cases of the compounds 1 to 27 of the present invention, absorptions peaks were present from the ultraviolet wavelength region to the visible light short wavelength region; it was indicated that these compounds would function as ultraviolet absorbers when added to films and resins, for example.

With regard to the absorption peaks in the wavelength region of 350 to 430 nu, it was confirmed that as compared to the conventional ultraviolet absorber of a long-wavelength absorption type (compound 29), the benzotriazole-based compounds 1 to 27 of the present invention in which the bonding group represented by the formula (I) or (L) had been introduced into benzotriazole were superior in ultraviolet absorption as the maximum absorption peaks thereof had shifted toward the long-wavelength region, and the absorption peaks thereof were present in an even longer-wavelength region of 355 nm or longer. Particularly, the compound 1 (386 nm), compound 4 (387 nm), compound 11 (380 nm), compound 14 (376 nm), compound 15 (375 urn), compound 22 (380 nm), compound 23 (389 urn), compound 24 (388 urn), compound 25 (385 nm), compound 26 (388 nm) and compound 27 (370 nm) were superior in long-wavelength absorption by having an absorption peak at a wavelength of 370 nm or longer; the compound 2 (390 un), compound 3 (396 nm), compound 5 (391 nm), compound 7 (395 un) and compound 10 (391 nm) were superior in long-wavelength absorption by having an absorption peak at a wavelength of 390 nm or longer; and the compound 6 (406 nm), compound 8 (401 nm), compound 9 (411 nm) and compound 21 (413 nm) were superior in long-wavelength absorption by having an absorption peak at a wavelength of 400 nm or longer.

When l=1, X is a nitrogen atom and $Y^2$ is a hydrogen atom in the formula (I), as compared to the compound 1, compounds having an oxygen-containing group or nitrogen-containing group in $Y^1$, or compounds in which $Y^1$ is a benzene ring, and the benzene ring has one substituent group (compounds 2, 3, 7, 8, 9, 10, 22 to 26) exhibited absorption peaks that had shifted toward the long-wavelength region; each absorption peak was at a wavelength of 380 un or longer.

Further, while a compound with a hydrogen atom being introduced into $Y^2$ (compound 1: 386 nm) exhibited an absorption peak at 375 nm or longer, the absorption peak shifted toward the long-wavelength region and was observed at a wavelength of 390 urn or longer by introducing an aliphatic hydrocarbon group into $Y^2$ (compound 5: 391 nm), and the absorption peak likewise shifted toward the long-wavelength region and was even observed at a wavelength of 400 nm or longer by introducing an aromatic hydrocarbon group into $Y^2$ (compound 6: 406 nm, compound 21: 413 nm).

Meanwhile, as for the absorption peaks in the wavelength region of 350 to 430 nm, the absorption peaks shifted toward the long-wavelength region in an order of compound 10>compound 20>compound 16, compound 1>compound 12>compound 17, and in terms of X, the absorption peaks shifted toward the long-wavelength region in an order of (l=1, X is a nitrogen atom)>(l=1, X is an amide group)>(l=0)>(l=1, X is an oxygen atom); a high usefulness was confirmed. Further, as for the formula (II), there is a correlation that compounds 13 to 15, 27<compounds 1 to 11, 21 to 26 i.e. as compared to the formula (II), compounds in which 1=1, and X is a nitrogen atom in the formula (T) were superior in long-wavelength absorption.

As for molar extinction coefficient, among the compounds having the substituent group(s) at $R^6$ to $R^9$ in the benzotriazole represented by the formula (A), the benzotriazole-based compounds 1 to 27 of the present invention into which the bonding group represented by the formula (I) or (II) had been introduced exhibited molar extinction coefficients of not smaller than 17,200 L/(mol cm) which were higher than that of the conventional ultraviolet absorber of a long-wavelength absorption type (compound 29: 15,300 L/(mol·cm)) and that of an ultraviolet absorber having a similar structure (compound 31: 17,100 L/(mol·cm)); it was confirmed that the compounds 1 to 27 were superior in ultraviolet absorption capability at the absorption peaks in the wavelength region of 350 to 430 nm, and that a light having a target wavelength could be efficiently absorbed even with a small additive amount of the compound(s) of the present invention. Particularly, the compounds 15, 23 exhibited high molar extinction coefficients of 18,000 L/(mol·cm) or larger, the compound 1, compounds 4 to 6, compounds 8 to 14, compounds 16 to 20 and 24 to 27 exhibited high molar extinction coefficients of 20,000 L/(mol·cm) or larger, the compound 3, compound 7 and compound 22 exhibited high molar extinction coefficients of 30,000 L/(mol·cm) or larger; these compounds were superior in ultraviolet absorption capability. That is, it was confirmed that the compounds 7, 22 having two benzotriazole skeletons therein, especially, the compound 3 having a nitro group in $Y^1$ though having one benzotriazole skeleton had exhibited high molar extinction coefficients and were thus superior.

As for the gradient of a peak (absolute value), the absolute values of the gradients of the absorption peaks of the benzotriazole-based compounds 1 to 27 of the present invention in which the bonding group represented by the formula (I) or (II) had been introduced into benzotriazole, on the long-wavelength side in the wavelength region of 350 to 430 nm, were all not smaller than 0.015; it was confirmed that these gradients were larger than that of the compound 29 which was the conventional ultraviolet absorber of a long-wavelength absorption type (comparative example 1: 0.011). Particularly, the compounds 1, 3 to 6 and 8 to 27 exhibited gradients of not smaller than 0.020; the compounds 1, 4 to 6, 8 to 12, 14 to 20 and 22 to 27 exhibited gradients of not smaller than 0.025. Further, the compounds L, 4, 5, 11, 14, 18 to 20, 22 and 24 to 27 exhibited gradients of not smaller than 0.030; the gradients exhibited by these compounds were larger than that of the compound 31 (comparative example 3: 0.028) as an analogous compound in which $Y^1$ is an aliphatic hydrocarbon group, and no hetero ring is formed i.e. it was indicated that these compounds were superior to the compound 31 in wavelength selectivity. Especially, the compounds 1, 4, 11, 14, 18, 19 and 24 to 26 exhibited gradients of not smaller than 0.034, the gradients exhibited by these compounds were larger than that of the compound 30 (comparative example 2) i.e. it was indicated that these compounds were superior to the compound 30 in wavelength selectivity.

Moreover, large gradients of 0.030 or larger were confirmed with the compound 1 (0.034) where, in the formula (I), 1=1, X is a nitrogen atom, $Y^1$ is a monocyclic and unsubstituted aromatic hydrocarbon group (phenyl group), and $Y^2$ is a hydrogen atom; the compound 5 (0.031) where, in the formula (I), 1=1, X is a nitrogen atom, $Y^1$ is a monocyclic and unsubstituted aromatic hydrocarbon group (phenyl group), and $Y^2$ is an aliphatic hydrocarbon group; and the compound 11 (0.095) where, in the formula (I), l=1, X is a nitrogen atom, and $Y^1$ is a tricyclic or more complex condensed ring directly bonded to the nitrogen atom.

Further, large gradients of 0.030 or larger were confirmed with the compounds 11 (0.095) and 22 (0.031, benzotriazole skeleton as a condensed ring) where, in the formula (I), $Y^1$ is a condensed ring containing at least one (at least two) six-membered ring (aromatic hydrocarbon group: phenyl group); particularly, it was confirmed that the compound 11 where an oxygen-containing group(s) is contained in the condensed ring of $Y^1$ exhibited an especially high gradient of 0.095.

The compounds 13 (0.022), 14 (0.034) and 27 (0.037) containing at least one five-membered ring exhibited large gradients of 0.015 or larger. Further, the gradients exhibited by the compounds 14 (0.034) and 27 (0.037) where, in the formula (II), the hetero ring is bicyclic or more complex were larger than those exhibited by the compounds 13 (0.022) and 15 (0.025) where, in the formula (II), the hetero ring is composed of a monocyclic ring; the gradients exhibited by the compounds 15 (one six-membered ring: 0.025) and 14 (two six-membered rings: 0.034) where, in the formula (II), the hetero ring contains at least one six-membered ring were larger than that of the compound 27 (one six-membered ring: 0.037) and the compound 13 (0.022) where no six-membered ring is contained in the hetero ring. Moreover, even among the compounds containing one six-membered ring, the gradient exhibited by the compound 27 (one six-membered ring: 0.037) containing an aromatic hydrocarbon group was larger than that of the compound 15 (one six-membered ring: 0.025) containing no aromatic hydrocarbon group.

Gradients of 0.025 or larger were observed with the compounds 17 (0.028), 18 (0.034), 19 (0.034) and 20 (0,033) where, in the formula (I), l=0, and Y is an aromatic hydrocarbon group (phenyl group); particularly, as a result of comparing the compounds 17 (0.028), 19 (0.034) and 20 (0.033) having an identical substituent group in $R^1$, $R^2$ and $R^4$ of the formula (A), the compounds 19 and 20 in which the aromatic hydrocarbon group (phenyl group) represented $Y^1$ contains an oxygen-containing group and nitrogen-containing group were confirmed to have exhibited high gradients of 0.030 or higher, and the compound 20 containing an oxygen-containing group was confirmed to have exhibited a gradient of 0.033.

Large gradients of 0.030 or larger were confirmed with all the compound 22 (0.031) where, in the formula (I), l=1, X is a nitrogen atom, and Y is an aromatic hydrocarbon group (phenyl group) containing a sulfur-containing group; the compound 24 (0.034) where, in the formula (I), l=1, X is a nitrogen atom, and $Y^1$ is an aromatic hydrocarbon group (phenyl group) containing a hydroxyalkyl group; and the compounds 25 (0.040) and 26 (0.040) where, in the formula (I), l=1, X is a nitrogen atom, and $Y^1$ is an aromatic hydrocarbon group (phenyl group) containing a (meth) acryloyl group.

FIG. 1A

| Compound | Structural formula | Formula (I) | | | | Formula (II) |
|---|---|---|---|---|---|---|
| | | X | Y¹ | m | Y² | |
| | | N | | 1 | H | — |
| 1 (Working example 1) | | | phenyl | | | |
| 2 (Working example 2) | | | 4-MeO-phenyl | | | — |
| 3 (Working example 3) | | | 4-O₂N-phenyl | | | — |
| 4 (Working example 4) | | | naphthyl | | | — |
| 5 (Working example 5) | | | phenyl | | Me | — |

FIG. 1A-continued

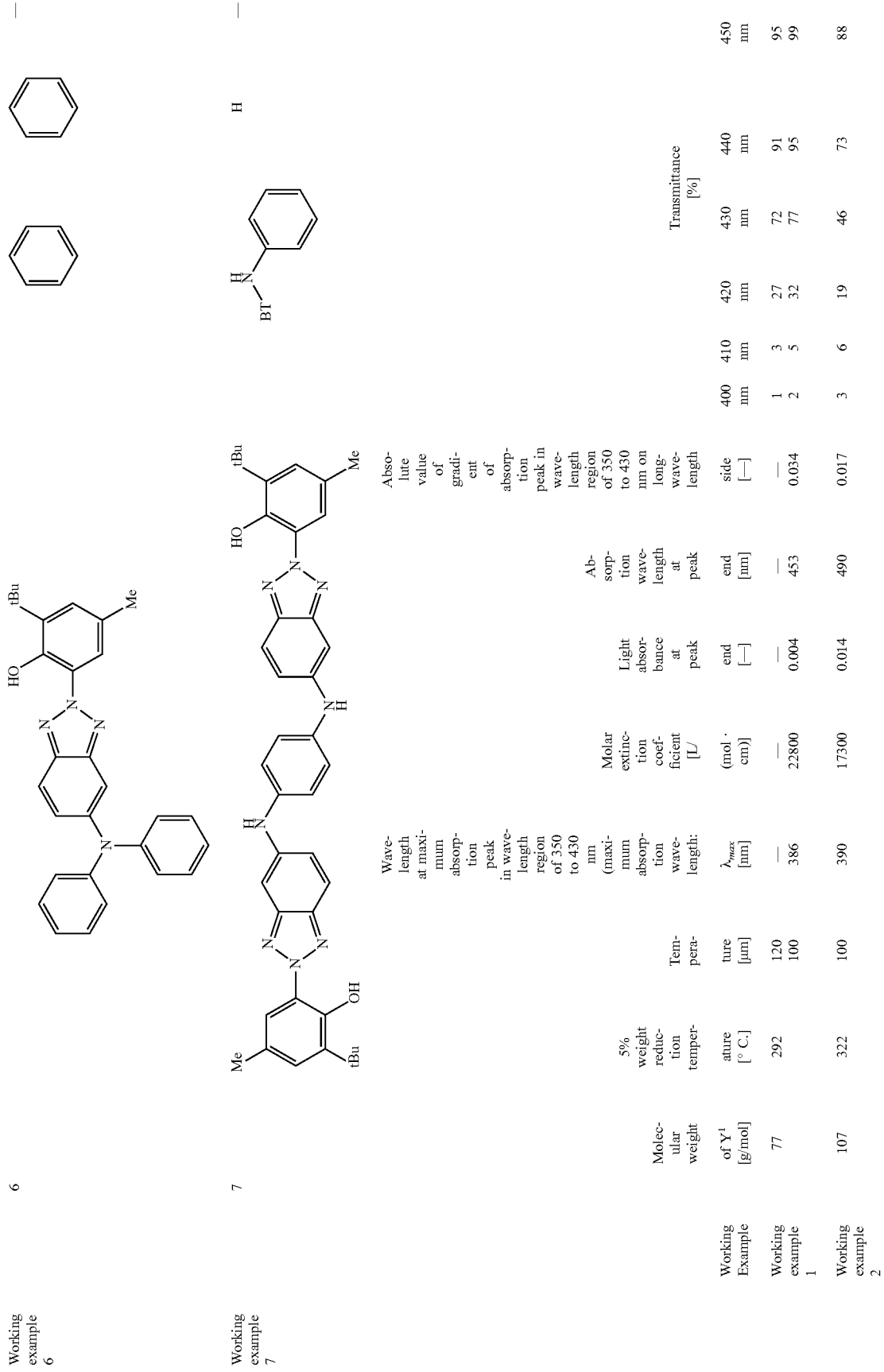

| | | Molecular weight of $Y^1$ [g/mol] | 5% weight reduction temperature [° C.] | Temperature [μm] | Wavelength at maximum absorption peak in wavelength region of 350 to 430 nm (maximum absorption wavelength: $\lambda_{max}$ [nm] | Molar extinction coefficient [L/(mol·cm)] | Light absorbance at peak end [—] | Absorption wavelength at peak end [nm] | Absolute value of gradient of absorption peak in wavelength region of 350 to 430 nm on long-wavelength side [—] | \multicolumn{6}{c}{Transmittance [%]} |
|---|---|---|---|---|---|---|---|---|---|---|---|---|---|---|---|
| | | | | | | | | | | 400 nm | 410 nm | 420 nm | 430 nm | 440 nm | 450 nm |
| Working Example 6 | | | | | | | | | | | | | | | |
| Working example 1 | | 77 | 292 | 120 | — | — | — | — | — | 1 | 3 | 27 | 72 | 91 | 95 |
| Working example 2 | | 107 | 322 | 100 | 386 | 22800 | 0.004 | 453 | 0.034 | 2 | 5 | 32 | 77 | 95 | 99 |
| | | | | 100 | 390 | 17300 | 0.014 | 490 | 0.017 | 3 | 6 | 19 | 46 | 73 | 88 |

FIG. 1A-continued
| | | | | | | | | | | | | | | |
|---|---|---|---|---|---|---|---|---|---|---|---|---|---|---|
| Working example 3 | 122 | 300 | 50 | 396 | 36000 | 0.012 | 472 | 0.024 | 2 | 3 | 10 | 31 | 60 | 81 |
| Working example 4 | 127 | 326 | 100 | 387 | 21600 | 0.034 | 450 | 0.034 | 1 | 6 | 22 | 56 | 85 | 96 |
| Working example 5 | 77 | 264 | 100 | 391 | 22700 | 0.003 | 464 | 0.031 | 1 | 2 | 12 | 45 | 79 | 94 |
| Working example 6 | 77 | 290 | 100 | 406 | 20300 | 0.003 | 485 | 0.026 | 1 | 1 | 2 | 6 | 24 | 39 |
| Working example 7 | 371 | 348 | 50 | 395 | 36800 | 0.016 | 500 | 0.017 | 2 | 3 | 6 | 17 | 37 | 61 |
| | | | 30 | — | — | — | — | — | 8 | 11 | 20 | 35 | 55 | 73 |
BT = 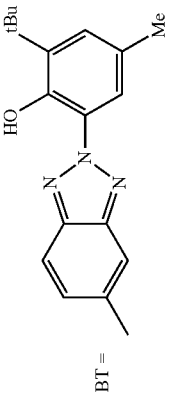

TABLE 1B

| Working example | Compound | Structural formula | Formula (I) | | | | Formula (II) |
|---|---|---|---|---|---|---|---|
| | | | l | X | Y¹ | m Y² | |
| Working example 8 | 8 | [structure: benzotriazole with HO, tBu, Me phenol linked via NH to 2-acetylphenyl] | 1 | N | [acetophenone group] | 1 H | — |
| Working example 9 | 9 | [structure: benzotriazole with HO, tBu, Me phenol linked via NH to 2-benzoylphenyl] | | | [benzophenone group] | | — |
| Working example 10 | 10 | [structure: benzotriazole with HO, tBu, Me phenol linked via NH-phenyl-NH-C(O)-phenyl] | | | [benzanilide group] | | — |
| Working example 11 | 11 | [structure: benzotriazole with HO, tBu, Me phenol linked via NH to anthraquinonyl] | | | [anthraquinone group] | | — |

TABLE 1B-continued

| | | | | | |
|---|---|---|---|---|---|
| Working example 12 | 12 | *[benzotriazole-phenol(OH, tBu, Me)]-NH-C(=O)-phenyl* | C(=O)—NH | phenyl | — |
| Working example 13 | 13 | *[benzotriazole-phenol(OH, tBu, Me)]-N-pyrrole* | — | — | N-pyrrolyl |
| Working example 14 | 14 | *[benzotriazole-phenol(OH, tBu, Me)]-N-carbazole* | — | — | N-carbazolyl |
| Working example 15 | 15 | *[benzotriazole-phenol(OH, tBu, Me)]-N-piperidine* | — | — | N-piperidinyl |

Wavelength at maximum absorption peak in wavelength region of 350

Absolute value of gradient of absorption peak in wave-

TABLE 1B-continued

| Working Example | Molecular weight of Y¹ [g/mol] | 5% weight reduction temperature [° C.] | Temperature [µm] | to 430 nm (maximum absorption wavelength) $\lambda_{max}$ [nm] | Molar extinction coefficient [L/(mol·cm)] | Light absorbance at peak end [—] | Absorption wavelength at peak end [nm] | length region of 350 nm to 430 nm on longwavelength side [—] | Transmittance [%] 400 nm | 410 nm | 420 nm | 430 nm | 440 nm | 450 nm |
|---|---|---|---|---|---|---|---|---|---|---|---|---|---|---|
| Working example 8 | 119 | 280 | 100 40 | 401 — | 25200 — | 0.016 — | 500 — | 0.025 — | 0 9 | 0 10 | 1 18 | 14 45 | 54 77 | 83 91 |
| Working example 9 | 181 | 263 | 100 | 411 | 22500 | 0.017 | 500 | 0.025 | 1 | 1 | 1 | 3 | 13 | 37 |
| Working example 10 | 196 | 374 | 100 | 391 | 21800 | 0.013 | 465 | 0.029 | 1 | 2 | 11 | 40 | 74 | 91 |
| Working example 11 | 207 | 382 | 100 | 380 | 20900 | 0.232 | 425 | 0.095 | 4 | 24 | 56 | 56 | 48 | 38 |
| Working example 12 | 77 | 319 | 100 | 359 | 23300 | 0.019 | 440 | 0.029 | 60 | 88 | 94 | 96 | 96 | 96 |
| Working example 13 | — | 266 | 100 | 362 | 22800 | 0.003 | 460 | 0.022 | 49 | 84 | 95 | 97 | 98 | 99 |
| Working example 14 | — | 329 | 2000 100 | — 376 | — 20500 | — 0.003 | — 436 | — 0.034 | 0 8 | 0 41 | 4 84 | 59 98 | 89 100 | 94 100 |
| Working example 15 | — | 260 | 100 | 375 | 18800 | 0.003 | 460 | 0.025 | 8 | 22 | 45 | 69 | 87 | 96 |

TABLE 1C

| Working example | Compound | Structural formula | Formula (I) | | | | | Formula (II) |
|---|---|---|---|---|---|---|---|---|
| | | | I | X | Y¹ | m | Y² | |
| Working example 16 | 16 | [benzotriazole with tBu/Me/OH phenyl; benzotriazole ring linked via O to phenyl-NH-C(=O)-phenyl] | 1 | O | [phenyl-C(=O)-NH-phenyl] | 0 | — | — |
| Working example 17 | 17 | [benzotriazole with tBu/Me/OH phenyl; linked to phenyl] | 0 | — | [phenyl] | — | — | — |
| Working example 18 | 18 | [benzotriazole with tBu/tBu/OH phenyl; linked to phenyl] | — | — | [phenyl] | — | — | — |
| Working example 19 | 19 | [benzotriazole with tBu/Me/OH phenyl; linked to phenyl-C(=O)-O-CH2-phenyl] | — | — | [phenyl-C(=O)-O-CH2-phenyl] | — | — | — |

TABLE 1C-continued

| | | | | |
|---|---|---|---|---|
| Working example 20 | 20 | (benzotriazole with tBu/Me phenol and phenyl-NHC(O)Ph amide substituent) | (PhC(O)NH-phenyl) | — |
| Working example 21 | 21 | (benzotriazole with tBu/Me phenol and N(p-tolyl)₂ amine substituent) | (p-tolyl) | (p-tolyl) |
| Working example 22 | 22 | (bis-benzotriazole linked via phenyl-S-phenyl-NH, both with tBu/Me phenol) | (BT—S—phenyl) | H |
| Working example 23 | 23 | (benzotriazole with tBu/Me phenol and NH-(4-hydroxyphenyl) substituent) | (4-hydroxyphenyl) | — |
| | | Wavelength at maximum absorption peak | | Absolute value of gradient of |

TABLE 1C-continued

| Working Example | Molecular weight of Y¹ [g/mol] | 5% weight reduction temperature [° C.] | Temperature [μm] | in wavelength region of 350 to 430 nm (maximum absorption wavelength: λ_max [nm] | Molar extinction coefficient [L/(mol·cm)] | Light absorbance at peak end [—] | Absorption wavelength at peak end [nm] | absorption peak in wavelength region of 350 to 430 nm on long-wavelength side [—] | Transmittance [%] 400 nm | 410 nm | 420 nm | 430 nm | 440 nm | 450 nm |
|---|---|---|---|---|---|---|---|---|---|---|---|---|---|---|
| Working example 16 | 191 | 352 | 100 | 355 | 20400 | 0.003 | 424 | 0.026 | 81 | 96 | 99 | 100 | 100 | 100 |
| Working example 17 | 77 | 271 | 100 | 357 | 22600 | 0.011 | 424 | 0.028 | 59 | 88 | 96 | 97 | 97 | 98 |
| Working example 18 | 77 | 277 | 100 | 356 | 23200 | 0.002 | 424 | 0.034 | 67 | 93 | 99 | 100 | 100 | 100 |
| Working example 19 | 211 | 348 | 100 | 361 | 24700 | 0.002 | 434 | 0.034 | 28 | 70 | 94 | 99 | 100 | 100 |
| Working example 20 | 191 | 380 | 100 | 360 | 25000 | 0.002 | 435 | 0.033 | 28 | 71 | 94 | 99 | 100 | 100 |
| Working example 21 | 91 | 324 | 100 | 413 | 17510 | 0.027 | 487 | 0.023 | 3 | 3 | 2 | 4 | 9 | 26 |

TABLE 1C-continued
| Working example 22 | 389 | 356 | 50 | 380 | 41900 | 0.031 | 0.031 | 445 | 3 | 11 | 42 | 76 | 90 | 94 |
| Working example 23 | 93 | 302 | 100 | 389 | 18190 | 0.011 | 0.026 | 459 | 2 | 6 | 19 | 49 | 77 | 92 |
BT = 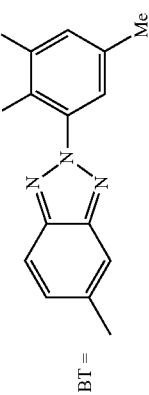

TABLE 1D

| Working example | Compound | Structural formula | Formula (I) | | | | | Formula (II) |
|---|---|---|---|---|---|---|---|---|
| | | | l | X | Y¹ | m | Y² | |
| Working example 24 | 24 | benzotriazole with HO, tBu, Me phenol and NH-phenyl-CH₂CH₂OH | 1 | N | phenethyl alcohol | 1 | H | — |
| Working example 25 | 25 | benzotriazole with HO, tBu, Me phenol and NH-phenyl-O-methacrylate | — | — | phenyl methacrylate ester | — | — | — |
| Working example 26 | 26 | benzotriazole with HO, tBu, Me phenol and NH-phenyl-CH₂CH₂-O-methacrylate | — | — | phenethyl methacrylate ester | — | — | — |
| Working example 27 | 27 | benzotriazole with HO, tBu, Me phenol and N-indolyl | — | — | — | — | — | N-methylindole |
| Comparative example 1 | 29 | benzotriazole with HO, tBu, Me phenol and Cl | — | — | — | — | — | — |

TABLE 1D-continued

| | Y¹ structure | | |
|---|---|---|---|
| Comparative example 2 | 30 | (benzotriazole with HO and Me substituted phenyl) | — |
| Comparative example 3 | 31 | (benzotriazole-N(Et)₂ with HO, tBu, Me substituted phenyl) | — |

| | Molecular weight of Y¹ [g/mol] | 5% weight reduction temperature [°C] | Temperature [μm] | Wavelength at maximum absorption peak in wavelength region of 350 to 430 nm (maximum absorption wavelength) λ_max [nm] | Molar extinction coefficient [L/(mol·cm)] | Light absorbance at peak end [—] | Absorption wavelength at peak end [nm] | Absolute value of gradient of absorption peak in wavelength region of 350 to 420 nm on long-wavelength side [—] | Transmittance [%] 400 nm | 410 nm | 420 nm | 430 nm | 440 nm | 450 nm |
|---|---|---|---|---|---|---|---|---|---|---|---|---|---|---|
| Working example 24 | 121 | 327 | 100 | 388 | 21570 | 0.028 | 451 | 0.034 | 1 | 4 | 22 | 64 | 87 | 94 |

TABLE 1D-continued

| | | | | | | | | | | | | | | |
|---|---|---|---|---|---|---|---|---|---|---|---|---|---|---|
| Working example 25 | 161 | 339 | 100 | 385 | 23040 | 0.012 | 442 | 0.040 | 1 | 5 | 32 | 77 | 96 | 97 |
| Working example 26 | 169 | 336 | 100 | 388 | 22480 | 0.019 | 444 | 0.040 | 1 | 4 | 21 | 65 | 92 | 99 |
| Working example 27 | — | 297 | 100 | 370 | 21630 | 0.037 | 428 | 0.037 | 17 | 62 | 88 | 92 | 93 | 94 |
| Comparative example 1 | — | 230 | 100 | 353 | 15300 | 0.002 | 424 | 0.011 | 74 | 93 | 98 | 100 | 100 | 100 |
| Comparative example 2 | — | 167 | 100 | (341) | 18800 | 0.003 | 400 | 0.032 | 99 | 100 | 100 | 100 | 100 | 100 |
| Comparative example 3 | — | 244 | 100 | 400 | 17100 | 0.003 | 462 | 0.028 | 2 | 3 | 5 | 14 | 51 | 89 |

(4) Transmittance

As shown in Table 1, each of the compounds 1 to 27, 29 to 31 was diluted with chloroform at a given concentration of 30 to 2,000 μM, followed by putting each compound into a 10 mm quartz cell, and then using an ultraviolet-visual-near-infrared spectrophotometer (UH4150V by Hitachi High-Tech Science Corporation) to measure a transmission spectrum thereof from which a transmittance at 400 to 450 nm was then read (Tables 1A to 1D).

The benzotriazole-based compounds 2 (100 LM 400 nm: 3%, 430 nm: 46%, 440 nm: 73%), 3 (50 μM, 400 nm: 2%, 430 nm: 31%, 440 nm: 60%), 7 (30 μM, 400 nm: 8%, 430 nm: 35%, 440 nm: 55%), 8 (40 μM, 400 nm: 9%, 430 nm: 45%, 440 nm: 77%), 10 (100 μM, 400 nm: 1%, 430 nm: 40%, 440 nm: 74%), 15 (100 μM 400 nm: 8%, 430 nm: 69%, 440 nm: 87%) and 23 (100 μM, 400 nm: 2%, 430 nm: 49%, 440 nm: 77%) of the present invention in which the bonding group represented by the formula (I) or (II) had been introduced into benzotriazole exhibited transmittances of not higher than 10% at 400 m, not higher than 75% at 430 nm, and not lower than 53% at 440 nm; these compounds were superior in absorbing lights of wavelengths up to 430 nm, and were superior in transmittivity of lights of wavelengths in the visible light region from 440 nm.

Further, the compounds 1 (120 μM, 400 nm: 1%, 430 nm: 72%, 440 nm: 91%), 4 (100 μM, 400 inn: 1%, 430 nm: 56%, 440 nm: 85%), 5 (100 μM, 400 nm: 1%, 430 nm: 45%, 440 nm: 79%), 14 (2,000 μM 400 nm: 0%, 430 nm: 59%, 440 nm: 89%), 24 (100 μM, 400 nm: 1%, 430 nm: 64%, 440 nm: 87%) and 26 (100 μM, 400 nm: 1%, 430 nm: 65%, 440 nm: 92%) exhibited transmittances of not higher than 1% at 400 mu, not higher than 75% at 430 nm, and not lower than 75% at 440 nm; these compounds were superior in the above optical properties, particularly, the compounds 4, 5, 24 and 26 were feasible at low concentrations.

(5) Compatibility to Resin

Compatibility was confirmed using a thermoplastic resin such as polymethyl methacrylate as a (meth)acryl-based resin, polyethylene terephthalate as an ester-based resin, polystyrene as a styrene-based resin, polycarbonate as a polycarbonate-based resin, an acrylonitrile-butadiene-styrene-copolymer as an acrylonitrile-butadiene-styrene-based copolymer, and a cycloolefin polymer as a cycloolefin-based resin; and a thermosetting resin such as an acrylic melamine resin as an acrylic melamine-based resin, a urea-formaldehyde resin as a urea-formaldehyde-based resin, and a melamine resin as a melamine-based resin.

(5-1) Compatibility to Resin (A)

A compatibility (transparency) of the compound of the present invention to a film and a resin member was confirmed by the following method (Table 2).

(Production of Polymethyl Methacrylate Film)

After uniformly mixing 0.1 g of each of the compounds 17, 18, 0.1 g of polymethyl methacrylate and 4 g of chloroform, the mixture was then delivered onto a glass slide by drops, followed by heating the same in an oven of 45° C. for two hours so as to remove the solvent, thereby obtaining the film.

Further, as a blank sample, 0.1 g of polymethyl methacrylate and 4 g of chloroform were uniformly mixed, followed by carrying out operations similar to those described above, thereby obtaining a polymethyl methacrylate film having a film thickness of 50 to 300 μm.

(Production of Acrylic Melamine Resin Film)

Here, 4.5 mg of each of the compounds 17, 18 was dissolved in 0.1 mL, of THF, and mixed with a bake-drying type topcoating material (ACRYCITE UB-63 CLEAR by Saito Paint Co., Ltd.). The mixture was then applied to a 1.5×1.5 cm glass slide by an amount of 0.2 mL. This glass slide was later put into an oven; after raising the temperature from 25° C. to 150° C. in 30 min, the glass slide was then left to stand still at 150° C. for two hours, thereby obtaining an acrylic maline resin film containing the compound by an amount of 10 wt %.

Further, as a blank sample, 0.1 mL of an acrylic melamine monomer and 0.1 mL of THF were uniformly mixed, followed by carrying out operations similar to those described above, thereby obtaining an acrylic melamine resin film having a film thickness of 100 to 150 min.

The appearances of the films produced were visually observed, and evaluated based on the criteria shown below Evaluation Criteria ○: Same level of transparency exhibited as compared to blank sample Δ: Slightly clouded as compared to blank sample x: Severely clouded as compared to blank sample In terms of an acrylic film, it was confirmed that a film with a favorable transparency and no white turbidity was able to be obtained in each case of the compounds 17 and 18.

Further, in terms of an acrylic melamine film, it was confirmed that a film with a favorable transparency and no white turbidity (favorable compatibility) was able to be obtained in the case of the compound 17 ($Y^1$: Ph-, substituent groups at $R^2$, $R^4$: methyl group, t-butyl group) rather than the compound 18 ($Y^1$: Ph-, substituent groups at $R^1$, $R^4$: t-butyl group, t-butyl group), where while $Y^1$ and X in the compounds 17 and 18 are similar, the substituent groups at $R^1$ to $R^5$ differ therebetween; and that a compound having methyl at $R^1$ to $R^5$ was superior in compatibility.

TABLE 2

| Working example | Compound | Structural formula | Compatitbility to resin | |
|---|---|---|---|---|
| | | | Methyl polymethacrylate | Acrylic melamine resin |
| Working example 28 | Compound 17 | 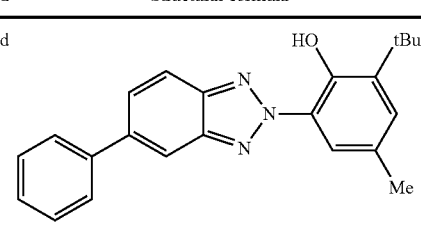 | ○ | ○ |

TABLE 2-continued

| | | | Compatibility to resin | |
|---|---|---|---|---|
| Working example | Compound | Structural formula | Methyl polymethacrylate | Acrylic melamine resin |
| Working example 29 | Compound 18 | (structure: 2-(2H-benzotriazol-2-yl)-4,6-di-tert-butylphenol with phenyl substituent) | ○ | △ |

(5-2) Compatibility to Resin (B)

A compatibility (transparency) of the compound of the present invention to a film and a resin member was confirmed by the following method (Table 3).

(Production of Polymethyl Methacrylate Film)

Here, 0.001 g of the compound 14, 29 or 31, 0.099 g of polymethyl methacrylate and 12 g of chloroform were uniformly mixed, followed by applying about 1 mL of the mixture to a glass substrate via spin coating under a condition(s) of 1,500 rpm, 20 sec, and then removing the solvent by leaving the glass substrate in an oven of 45° C. for two hours, thereby obtaining an acrylic film having a film thickness of 50 to 300 μm and containing the compound 14, 29 or 31 by an amount of 1 wt %.

Further, as a blank sample, 0.1 g of an acrylic resin and 12 g of chloroform were uniformly mixed, followed by carrying out operations similar to those described above, thereby obtaining a poly methyl methacrylate film having a film thickness of 50 to 300 μm.

(Production of Polyethylene Terephthalate Film (PET))

Here, 0.0004 g of the compound 14, 29 or 31 and 0.0396 g of polyethylene terephthalate chips were kneaded at 280° C., followed by applying the kneaded product to a glass slide, and then having it air-cooled, thereby obtaining a polyethylene terephthalate film having a film thickness of 20 to 200 μm and containing the compound 14, 29 or 31 by an amount of 1 wt %.

Further, as a blank sample, 0.045 g of polyethylene terephthalate chips were dissolved, followed by carrying out operations similar to those described above, thereby obtaining a polyethylene terephthalate film having a film thickness of 20 to 200 μm.

(Production of Polystyrene Film (PS))

Here, 0.001 g of the compound 14, 29 or 31, 0.099 g of a polystyrene resin (by Kanto Chemical Co, Inc.) and 4 g of chloroform were uniformly mixed, followed by condensing the chloroform by about 2 to 3 g, and then applying 50 μL of the mixture to a glass slide. Later, the glass slide was left in an oven of 45° C. for two hours to remove the solvent, thereby obtaining a polystyrene film having a film thickness of 10 to 50 μm and containing the compound 14, 29 or 31 by an amount of 1 wt %.

Further, as a blank sample, 0.1 g of the polystyrene resin and 4 g of chloroform were uniformly mixed, followed by carrying out operations similar to those described above, thereby obtaining a polystyrene film having a film thickness of 10 to 50 μm.

(Production of polycarbonate Film (PC))

Here, 0.001 g of the compound 14, 29 or 31, 0.099 g of a polycarbonate resin (by Kanto Chemical Co., Inc.) and 4 g of chloroform were uniformly mixed, followed by condensing the chloroform by about 2 to 3 g, and then applying 25 μL of the mixture to a glass slide. Later, the glass slide was left in an oven of 45° C. for two hours to remove the solvent, thereby obtaining a poly carbonate film having a film thickness of 10 to 50 μm and containing the compound 14, 29 or 31 by an amount of 1 wt %.

Further, as a blank sample, 0.1 g of the polycarbonate resin and 4 g of chloroform were uniformly mixed, followed by carrying out operations similar to those described above, thereby obtaining a polycarbonate film having a film thickness of 10 to 50 μm.

(Production of Acrylonitrile-Butadiene-Styrene Resin Film (ABS))

Here, 0.001 g of the compound 14, 29 or 31, 0.099 g of an ABS resin (TOYOLAC 950-X01 by Toray Industries, Inc.) and 20 g of chloroform were uniformly mixed, followed by condensing the chloroform, and then delivering 25 μL of the mixture onto a glass slide by drops. Later, the glass slide was left in an oven of 45° C. for two hours to remove the solvent, thereby obtaining an ABS film having a film thickness of 10 to 50 pam and containing the compound 14, 29 or 31 by an amount of 1 wt %.

Further, without adding an additive(s), 0.1 g of the ABS resin and 20 g of chloroform were uniformly mixed, followed by carrying out operations similar to those described above, thereby obtaining an ABS film having a film thickness of 10 to 50 μm.

(Production of Urea-Formaldehyde Resin Film)

A monomer solution w % as prepared by dissolving 1 mL of a 37 wt % formaldehyde solution, 0.25 g of urea and 0.16 g of ammonium acetate. Next, 0.007 g of the compound 14, 29 or 31 was dissolved into 20 mL of THF, followed by uniformly mixing 0.2 mL of such THF with 0.1 mL of the monomer solution, and then applying 0.3 mL of the mixture to a 1.5×1.5 cm glass slide. This glass slide was then put into an oven; by performing heating at 150'C for five hours, there was produced a urea-formaldehyde resin film having a film thickness of 40 to 80 μm and containing the compound 14, 29 or 31 by an amount of 1 wt %.

Further, as a blank sample, 0.1 mL of the monomer solution and 0.2 mL of THF were uniformly mixed, followed by carrying out operations similar to those described above, thereby obtaining a urea-formaldehyde resin film having a film thickness of 40 to 80 μm.

(Production of Melamine Resin Film)

Here, 1 g of melamine and 24.60 g of water were added to 5.15 g of a formaldehyde solution whose pH level had been adjusted to 7.5 with sodium hydroxide, followed by allowing them to react under a heated condition so as to obtain a hexamethylol melamine solution. Next, 0.0057 g of the compound of the working example 14, 29 or 31 was dissolved into 0.1 mL of THF, followed by uniformly mixing such THF with 0.2 mL of the hexamethylol melamine solution, and then applying 0.3 mL of the mixture to a 1.5×1.5 cm glass slide. This glass slide was then put into an oven; by performing heating at 150° C. for five hours, there was produced a melamine resin film having a film thickness of 10 to 50 pam and containing the compound 14, 29 or 31 by an amount of 1 wt %.

Further, as a blank sample, 0.2 mL of a monomer solution and 0.1 mL of THF were uniformly mixed, followed by carrying out operations similar to those described above, thereby obtaining a melamine resin film having a film thickness of 10 to 50 m.

(Production of Acrylic Melamine Resin Film)

Here, 0.0045 g of the compound 14, 29 or 31 was dissolved into 1 mL of THF, followed by uniformly mixing 0.1 mL of such TI-IF with 0.1 mL of the bake-drying type topcoating material (bake-drying type topcoat (acrylic melamine): ACRYCITE UB-63 CLEAR by Saito Paint Co., Ltd.), and then applying 0.2 mL of the mixture to a 1.5×1.5 cm glass slide, so that when formed into a film, the concentration of the compound 14, 29 or 31 therein would be 1 wt %. This glass slide was then put into an oven; by performing heating at 150° C. for two hours, there was produced an acrylic melamine resin film having a film thickness of 100 to 150 am and containing the compound 14, 29 or 31 by an amount of 1 wt %.

Further, as a blank sample, 0.1 mL of an acrylic melamine monomer and 0.1 mL of THF were uniformly mixed, followed by carrying out operations similar to those described above, thereby obtaining an acrylic melamine resin film having a film thickness of 100 to 150 μm.

(Production of Cycloolefin Polymer (COP) Resin Film)

Here, 0.001 g of the compound 14, 29 or 31 and 0.099 g of a COP resin were kneaded at 280° C., followed by applying the kneaded product to a glass slide, and then having it air-cooled, thereby obtaining a COP film having a film thickness of 20 to 200 μm and containing the compound 14, 29 or 31 by an amount of 1 wt %.

Further, as a blank sample, 0.045 g of a COP resin was dissolved, followed by carrying out operations similar to those described above, thereby obtaining a COP film having a film thickness of 20 to 200 μm.

The appearances of the films produced were visually observed, and evaluated based on the criteria shown below.

Evaluation Criteria

○: Same level of transparency exhibited as compared to blank sample

Δ: Slightly clouded as compared to blank sample x: Severely clouded as compared to blank sample As for the films containing the compound 14 of the present invention, it was confirmed that in the case of each type of resin, a film with a favorable transparency was able to be obtained in a way such that the film either exhibited the same level of transparency or was slightly clouded as compared to that of the corresponding blank sample. Even among the resins shown in Table 3, a favorable transparency was observed in the cases of the resins employing the thermoplastic resins (polymers, copolymers) such as polyethylene terephthalate, polystyrene, polycarbonate, polymethyl methacrylate, ABS and cycloolefin polymer; and thermosetting resins such as acrylic melamine resin as a polymer. Thus, it was suggested that the 2-phenylbenzotriazole derivative of the present invention had an excellent compatibility especially with thermoplastic resins (polymers, copolymers) and copolymers of thermosetting resins.

Also, as compared to the compound 29 of the comparative example which was the conventional ultraviolet absorber and the compound 31 as the analogous compound, overall, a more excellent compatibility to resins was observed in the case of the compound 14 as the ultraviolet absorber of the present invention where the hetero ring in the formula (II) is bicyclic or more complex, and has two six-membered-ring aromatic hydrocarbon groups (phenyl groups) and a five-membered ring.

TABLE 3

| Working example | Compound | Structural formula | Compatibility to resin | | | | | | | | |
|---|---|---|---|---|---|---|---|---|---|---|---|
| | | | Urea resin | Melamine resin | Acrylic melamine resin | PET | PS | PC | Methyl polymethacrylate | ABS | COP |
| Working example 30 | Compound 14 | (carbazole-substituted benzotriazole with HO, tBu, Me phenyl) | Δ | Δ | ○ | ○ | ○ | ○ | ○ | ○ | ○ |
| Comparative example 4 | Compound 29 | (Cl-substituted benzotriazole with HO, tBu, Me phenyl) | x | x | x | x | ○ | ○ | ○ | ○ | ○ |

TABLE 3-continued

| Working example | Compound | Structural formula | Compatibility to resin | | | | | | | | |
|---|---|---|---|---|---|---|---|---|---|---|---|
| | | | Urea resin | Melamine resin | Acrylic melamine resin | PET | PS | PC | Methyl polymethacrylate | ABS | COP |
| Comparative example 5 | Compound 31 | (structure: HO, tBu, Me, diethylamino-benzotriazole-phenyl) | x | x | x | x | ○ | ○ | ○ | ○ | ○ |

(6) Confirmation of Odor Caused by Thermal Decomposition

A compound with a sulfur-containing group being introduced into the 2-phenylbenzotriazole derivative (2-(2-hydroxy-3'-tert-butyl-5-methylphenyl)-5-octylthiobenzotriazole) and the compounds 1 to 20 with the bonding group represented by the formula (T) or (11) being introduced into the 2-phenylbenzotriazole derivative were each heated at 350° C. for 10 min using a muffle furnace; the presence or non-presence of an odor was then confirmed.

As a result, while an odor occurred at the time of decomposition in the case of the compound with the sulfur-containing group being introduced into the 2-phenylbenzotriazole derivative, no odor occurred in the cases of the compounds 1 to 20 with the bonding group represented by the formula (I) or (II) being introduced into the 2-phenylbenzotriazole derivative; it was indicated that the compounds 1 to 20 were able to be applied even to resins requiring higher molding and processing temperatures, and reduce odors at the time of processing.

(7) Evaluation on Light Resistance

The compounds 7, 8, 9, 10, 11, 13, 14, 15, 17, 18, 19, 20, 22, 27 and 31 were each added to a 2.5 wt % acrylic resin chloroform solution in a manner such that the compounds 8, 13, 14, 17, 18 and 27 were each added at a weight ratio (resin:compound) of 1:1, the compounds 9, 15, 19 and 31 were each added at a weight ratio (resin:compound) of 2:1, the compound 11 was added at a weight ratio (resin:compound) of 3:1, the compound 20 was added at a weight ratio (resin:compound) of 4:1, and the compounds 7, 10 and 22 were each added at a weight ratio (resin:conpound) of 6:1, followed by using a spin coater (MS-B150 by MIKASA CO., LTD) to form a thin film under a condition of rev. 1,500 rpm, 15 see, and then distilling away the organic solvent so as to complete producing the thin film. The ultraviolet-visual-near-infrared spectrophotometer (UH4150V by Hitachi High-Tech Science Corporation) was then used to measure a UV-Vis transmission spectrum of such thin film, and an initial (pre-irradiation) UV transmittance (%): A at 370 to 430 nm was read. Later, an ultraviolet irradiation device (weatherometer Ci3000+w by ATLAS) was used to perform ultraviolet irradiation under a condition(s) of wavelength 300 to 400 nm, irradiance 42 W/m$^2$, black panel temperature 63° C.; after performing irradiation for 100 hours, the UV-Vis transmission spectrum was measured, a transmittance (%): B at 370 to 430 nm was read, and a difference in transmittance before and after the irradiation ΔT: B-A (%) was calculated (Table 4).

TABLE 4

| Working example | Compound | Difference in transmittance ΔT [%] 100 [h] | | | | | | |
|---|---|---|---|---|---|---|---|---|
| | | 370 [nm] | 380 [nm] | 390 [nm] | 400 [nm] | 410 [nm] | 420 [nm] | 430 [nm] |
| Working example 31 | 7 | 23 | 33 | 41 | 45 | 46 | 42 | 35 |
| Working example 32 | 8 | 18 | 19 | 19 | 20 | 22 | 27 | 36 |
| Working example 33 | 9 | 11 | 15 | 19 | 23 | 26 | 27 | 26 |
| Working example 34 | 10 | 20 | 28 | 34 | 37 | 35 | 30 | 20 |
| Working example 35 | 11 | 8 | 9 | 10 | 10 | 10 | 4 | 2 |
| Working example 36 | 13 | 6 | 9 | 14 | 8 | 0 | 0 | 0 |
| Working example 37 | 14 | 2 | 2 | 3 | 4 | 4 | 0 | 0 |
| Working example 38 | 15 | 54 | 62 | 65 | 59 | 45 | 29 | 15 |
| Working example 39 | 17 | 1 | 1 | 3 | 3 | 1 | 0 | 2 |
| Working example 40 | 18 | 5 | 6 | 5 | 4 | 2 | 2 | 2 |
| Working example 41 | 19 | 3 | 3 | 4 | 3 | 2 | 3 | 3 |

TABLE 4-continued

| Working example | Compound | 370 [nm] | 380 [nm] | 390 [nm] | Difference in transmittance $\Delta$T [%] 400 [nm] 100 [h] | 410 [nm] | 420 [nm] | 430 [nm] |
|---|---|---|---|---|---|---|---|---|
| Working example 42 | 20 | 1 | 1 | 3 | 3 | 1 | 1 | 2 |
| Working example 43 | 22 | 34 | 39 | 42 | 40 | 33 | 22 | 11 |
| Working example 44 | 27 | 2 | 2 | 3 | 6 | 2 | 0 | 2 |
| Comparative example 6 | 31 | 45 | 60 | 70 | 76 | 75 | 70 | 57 |

As compared to the compound 31 of the comparative example in which a substituent group(s) are present at $R^6$ to $R^9$ of the benzotriazole represented by the formula (A), X is a nitrogen atom, and $Y^1$ is an aliphatic hydrocarbon group and does not form a hetero ring, smaller differences in transmittance before and after the irradiation at 370 to 430 nm were observed in the cases of the compounds 7 to 11, 13 to 15, 17 to 20, 22 and 27; these compounds were superior in light resistance. Particularly, the compounds 8, 9, 10, 11, 13, 14, 17, 18, 19, 20, 22 and 27 were superior in heat resistance as the compounds 8, 10 and 22 each exhibited a difference in transmittance of not larger than 45%, the compound 9 exhibited a difference in transmittance of not larger than 30%, the compound 13 exhibited a difference in transmittance of not larger than 15%, the compounds 11, 18 and 27 each exhibited a difference in transmittance of not larger than 10%, and the compounds 14, 17, 19 and 20 each exhibited a difference in transmittance of not larger than 5%.

Further, the compound 11 where, in the formula (I), l=1, X is a nitrogen atom and $Y^1$ is a tricyclic or more complex condensed ring, was superior in light resistance by exhibiting a difference in transmittance before and after the irradiation of not larger than 10%.

Further, the compounds 11, 22 ((benzo)triazole skeleton as condensed ring) where, in the formula (I), when Y is a condensed ring, the condense ring contains at least one six-membered ring (aromatic hydrocarbon), were superior in light resistance by exhibiting differences in transmittance of not larger than 45%; particularly, the compound 11 having an oxygen-containing group in the six-membered ring of $Y^1$ was superior in light resistance by exhibiting a difference in transmittance of not larger than 10%.

Meanwhile, it was confirmed that as compared to the compound 15 having no unsaturated bonds in the hetero ring in the formula (II), the compounds 13 (not larger than 15%), 14 (not larger than 5%) and 27 (not larger than 10%) having an unsaturated bond(s) in the hetero ring exhibited smaller differences in transmittance. Further, as compared to the compound 13 (not larger than 15%) having one hetero ring, the compounds 14 (not larger than 5%) and 27 (not larger than 10%) where the hetero ring is bicyclic or more complex were superior in light resistance; particularly, the compound 14 (not larger than 5%) having two six-membered rings (aromatic hydrocarbon groups) in the hetero ring exhibited a light resistance more excellent than that of the compound 27 (not larger than 10%) having one six-membered ring (aromatic hydrocarbon group) in the hetero ring. Moreover, the compounds 13 (not larger than 15%), 14 (not larger than 5%) and 27 (10%) having a five-membered ring(s) in the hetero ring exhibited a light resistance more excellent than that of the compound 15 having no five-membered ring in the hetero ring.

The compounds 17 (not larger than 5%), 18 (not larger than 10%), 19 (not larger than 5%) and 20 (not larger than 5%) where, in the formula (I), l=0, and $Y^1$ is an aromatic hydrocarbon group (phenyl group), exhibited differences in transmittance of not larger than 10%; particularly, it was confirmed that the compounds 19 (not larger than 5 wt %), 20 (not larger than 5 wt %) where the aromatic hydrocarbon group represented by Y contains an oxygen-containing group and nitrogen-containing group, were more excellent in light resistance by exhibiting differences in transmittance of not larger than 5%. Further, the compounds 17 (not larger than 5%), 19 (not larger than 5%) and 20 (not larger than 5%) where $R^2$ represents a butyl group, and $R^4$ represents a methyl group in the formula (A), exhibited a light resistance more excellent than that of the compound 18 (not larger than 10%) where each of $R^2$ and $R^4$ represents a butyl group.

The compound 22 where, in the formula (I), l=1, X is a nitrogen atom, and $Y^1$ is an aromatic hydrocarbon group (phenyl group) having a sulfur-containing group, exhibited a difference in transmittance of not larger than 45%; the compound 22 was superior to the compound 31 in light resistance.

(8) Evaluation on Reactivity

A reactivity test was performed on compounds having reactive functional groups with regard to an isocyanate compound.

The compound 23 (200 mg, 0.52 mmol) or 24 (290 mg, 0.70 mmol), hexamethylene diisocyanate (1.0 g, 5.9 mmol) and tetrahydrofuran (15 g) were mixed together, followed by adding thereto dibutyltin dilaurate (0.3 mg, 0.48 µmol) as a catalyst, and then stirring them under a heated condition at 60° C. for 24 hours so as to allow a polymerization reaction to take place.

As a result, with regard to each polymer obtained, since a —C(=O)— stretching vibration derived from a urea bond was newly observed via infrared spectroscopy, the reactivities of the compounds 23 and 24 of the present invention were favorable.

Further, a reactivity test was performed with regard to a (meth)acryl-based compound. The compound 26 (73 mg, 0.15 mmol) methyl methacrylate (0.5 g, 5.0 mmol) and toluene (1.0 g) were mixed together, followed by adding thereto 2,2'-azobis(isobutyronitrile) (2.5 mg, 0.015 mmol) as a polymerization initiator, and then stirring them under a heated condition at 90° C. for six hours so as to allow a polymerization reaction to take place.

As a result, with regard to a polymer obtained, it was confirmed via $^1$H-NMR measurement that a hydrogen atom peak attributed to a carbon-carbon double bond of a monomer had disappeared, and that the reaction had thus progressed; the reactivity of the compound 26 of the present invention was favorable.

It was confirmed that a compound having a reactive substituent group(s) in the formula (A) was capable of bonding to an organic material, thus being superior in, for example, preventing bleed-out or the like and ensuring the strength of the organic material.

The invention claimed is:

1. An ultraviolet absorber comprising a 2-phenylbenzotriazole derivative having a bonding group represented by the following formula (I):

[Chemical formula 1]

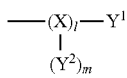

(I)

wherein X represents a nitrogen atom; l is 1; $Y^1$ represents a substituted or unsubstituted aromatic hydrocarbon group; m is 1; $Y^2$ represents a hydrogen atom, a substituted or unsubstituted aliphatic hydrocarbon group, or a substituted or unsubstituted aromatic hydrocarbon group, wherein $Y^1$ and $Y^2$ satisfy any one of the following i) to vi):
i) $Y^1$ is such that the aromatic hydrocarbon group is a bicyclic or more complex condensed ring, or that a substituent group(s) is present in the aromatic hydrocarbon group, and the substituent group(s) and the aromatic hydrocarbon group together form a ring(s),
ii) $Y^2$ is a hydrogen atom, and an oxygen-containing group or nitrogen-containing group is present in $Y^1$,
iii) $Y^2$ is a substituted or unsubstituted aliphatic hydrocarbon group, or a substituted or unsubstituted aromatic hydrocarbon group,
iv) $Y^1$ contains a bicyclic or more complex condensed ring directly bonded to the nitrogen atom represented by X,
v) $Y^1$ contains a bicyclic or more complex condensed ring bonded to a sulfur-containing group, or
vi) $Y^1$ has a reactive substituent group(s) in the aromatic hydrocarbon group, and wherein the 2-phenylbenzotriazole derivative is represented by the following formula (A):

[Chemical formula 3]

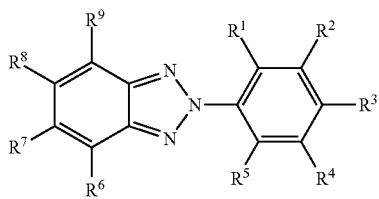

(A)

wherein $R^1$, $R^2$, $R^3$, $R^4$ and $R^5$ are each selected from a hydrogen atom, a methyl group, a t-butyl group and a hydroxy group and contain one or no t-butyl group, and at least one of the $R^1$, $R^2$, $R^3$, $R^4$ and $R^5$ is a methyl group, and each of $R^6$ to $R^9$ independently represents a monovalent or divalent group selected from the bonding group represented by the formula (I), a hydrogen atom, a hydrocarbon group, an unsaturated group, a nitrogen-containing group, a sulfur-containing group, an oxygen-containing group, a phosphorus-containing group and a halogen atom; at least one of $R^6$ to $R^9$ is the bonding group represented by the formula (I).

2. An organic resin composition comprising:
an ultraviolet absorber comprising a 2-phenylbenzotriazole derivative having a bonding group represented by the following formula (I-2):

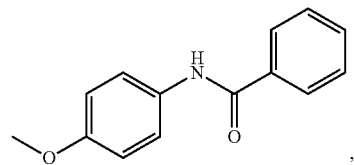

(I-2)

and wherein the 2-phenylbenzotriazole derivative is represented by the following formula (A):

[Chemical formula 3]

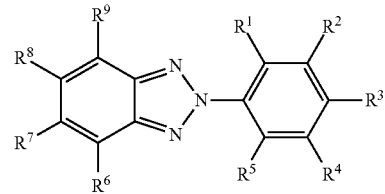

(A)

wherein $R^1$ is a hydroxy group, $R^2$ is a t-butyl group, $R^4$ is a methyl group, and $R^3$ and $R^5$ are hydrogen atoms, and each of $R^6$ to $R^9$ independently represents the bonding group represented by the formula (I-2), or a hydrogen atom; one of $R^6$ to $R^9$ is the bonding group represented by the formula (I-1) or (I-2); and an organic resin.

3. An organic resin composition comprising:
an ultraviolet absorber comprising a 2-phenylbenzotriazole derivative having a bonding group represented by the following formula (I-4) or (I-5):

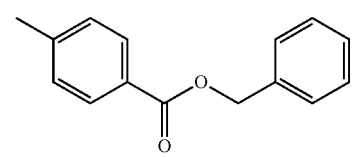

(I-4)

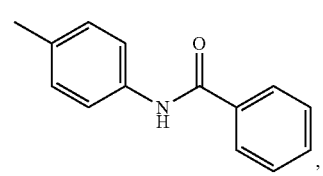

(I-5)

and wherein the 2-phenylbenzotriazole derivative is represented by the following formula (A):

[Chemical formula 3]

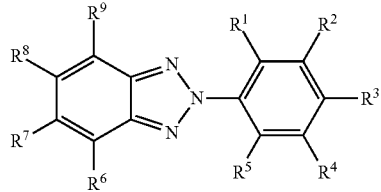

(A)

wherein R¹ is a hydroxy group, R² is a t-butyl group, R⁴ is a methyl group, and R³ and R⁵ are hydrogen atoms, and each of R⁶ to R⁹ independently represents the bonding group represented by the formula (I-4) or (I-5), or a hydrogen atom; at least one of R⁶ to R⁹ is the bonding group represented by the formula (I-4) or (I-5); and an organic resin.

4. An ultraviolet absorber comprising a 2-phenylbenzotriazole derivative having a bonding group represented by the following formula (II):

[Chemical formula 2]

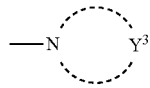

(II)

wherein Y³ forms an unsubstituted hetero ring together with a nitrogen atom N, the hetero ring being such that the hetero atom is a nitrogen atom, and wherein the 2-phenylbenzotriazole derivative is represented by the following formula (A):

[Chemical formula 3]

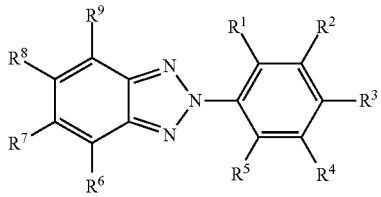

(A)

wherein R¹, R², R³, R⁴ and R⁵ are each selected from a hydrogen atom, a methyl group, a t-butyl group and a hydroxy group and contain one or no t-butyl group, and at least one of the R¹, R², R³, R⁴ and R⁵ is a methyl group, and each of R⁶ to R⁹ independently represents the bonding group represented by the formula (II) or a hydrogen atom; any one of R⁶ to R⁹ is the bonding group represented by the formula (II).

5. The ultraviolet absorber according to claim 4, wherein the bonding group is represented by the formula (II); in the formula (II), the hetero ring has at least one five-membered ring.

6. The ultraviolet absorber according to claim 5, wherein the hetero ring is bicyclic or more complex.

7. The ultraviolet absorber according to claim 4, wherein the bonding group is represented by the formula (II); in the formula (II), the hetero ring is polycyclic.

8. The ultraviolet absorber according to claim 4, wherein the bonding group is represented by the formula (II); in the formula (II), the hetero ring has at least one six-membered ring.

9. The ultraviolet absorber according to claim 8, wherein the six-membered ring is a phenyl ring.

* * * * *